US008399615B2

(12) United States Patent
Tanoury et al.

(10) Patent No.: US 8,399,615 B2
(45) Date of Patent: *Mar. 19, 2013

(54) PROCESSES AND INTERMEDIATES

(75) Inventors: Gerald J. Tanoury, Hudson, MA (US);
Minzhang Chen, Acton, MA (US);
John E. Cochran, Marshfield, MA (US);
Adam Looker, Cambridge, MA (US);
Valdas Jurkauskas, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 773 days.

This patent is subject to a terminal disclaimer.

(21) Appl. No.: 12/430,207

(22) Filed: Apr. 27, 2009

(65) Prior Publication Data
US 2010/0063252 A1 Mar. 11, 2010

Related U.S. Application Data

(63) Continuation-in-part of application No. 11/506,550, filed on Aug. 18, 2006, now Pat. No. 7,776,887.

(60) Provisional application No. 60/709,964, filed on Aug. 19, 2005, provisional application No. 60/810,042, filed on Jun. 1, 2006.

(51) Int. Cl.
A61K 38/00 (2006.01)
(52) U.S. Cl. ..................................... 530/333
(58) Field of Classification Search ........................ None
See application file for complete search history.

(56) References Cited

U.S. PATENT DOCUMENTS

| | | | | |
|---|---|---|---|---|
| 5,298,660 A * | 3/1994 | Yoneyoshi et al. | | 564/302 |
| 5,468,858 A | 11/1995 | Berlin et al. | | |
| 5,852,209 A * | 12/1998 | Nohira et al. | | 562/401 |
| 5,866,684 A | 2/1999 | Attwood et al. | | |
| 6,018,020 A | 1/2000 | Attwood et al. | | |
| 6,054,594 A * | 4/2000 | Potter et al. | | 548/953 |
| 6,143,715 A | 11/2000 | Llinas-Brunet et al. | | |
| 6,265,380 B1 | 7/2001 | Tung et al. | | |
| 6,608,027 B1 | 8/2003 | Tsantrizos et al. | | |
| 6,767,991 B1 | 7/2004 | Llinas-Brunet et al. | | |
| 2002/0016294 A1 | 2/2002 | Venkatraman et al. | | |
| 2002/0016442 A1 | 2/2002 | Llinas-Brunet et al. | | |
| 2002/0032175 A1 | 3/2002 | Tung et al. | | |
| 2002/0037998 A1 | 3/2002 | Llinas-Brunet et al. | | |
| 2002/0045729 A1 | 4/2002 | Kerres et al. | | |
| 2002/0065248 A1 | 5/2002 | Zhang et al. | | |
| 2002/0102235 A1 | 8/2002 | Arasappan et al. | | |
| 2002/0107181 A1 | 8/2002 | Chen et al. | | |
| 2002/0160962 A1 | 10/2002 | Saksena et al. | | |
| 2002/0177725 A1 | 11/2002 | Priestley | | |
| 2003/0008828 A1 | 1/2003 | Priestley et al. | | |
| 2003/0036501 A1 | 2/2003 | Saksena et al. | | |
| 2003/0064962 A1 | 4/2003 | Glunz et al. | | |
| 2003/0100768 A1 | 5/2003 | Han et al. | | |
| 2003/0119752 A1 | 6/2003 | Farmer et al. | | |
| 2003/0216325 A1 | 11/2003 | Saksena et al. | | |
| 2003/0236242 A1 | 12/2003 | Perni et al. | | |
| 2004/0077600 A1 | 4/2004 | Tung et al. | | |
| 2004/0142876 A1 | 7/2004 | Colarusso et al. | | |
| 2004/0180815 A1 | 9/2004 | Nakajima et al. | | |
| 2005/0080017 A1 | 4/2005 | Cottrell et al. | | |
| 2005/0119168 A1 * | 6/2005 | Venkatraman et al. | ........... | 514/9 |
| 2005/0197299 A1 | 9/2005 | Babine et al. | | |
| 2005/0197301 A1 | 9/2005 | Njoroge et al. | | |

FOREIGN PATENT DOCUMENTS

| | | |
|---|---|---|
| CN | 1451014 | 10/2003 |
| DE | 3211676 | 10/1983 |
| EP | 90362 | 10/1983 |
| EP | 1934179 | 4/2010 |
| JP | A-58-177967 | 10/1983 |
| JP | A-9-067344 | 3/1997 |
| JP | A-2005-526002 | 9/2005 |
| WO | WO 97/43310 | 11/1997 |
| WO | WO 98/22496 | 5/1998 |
| WO | WO 98/46630 | 10/1998 |
| WO | WO 99/38888 | 8/1999 |
| WO | WO/00/31129 | 6/2000 |
| WO | WO 02/18369 | 3/2002 |
| WO | WO 02/060926 | 8/2002 |
| WO | WO 03035060 | 5/2003 |
| WO | WO2005087730 | 9/2005 |
| WO | WO 2007022459 | 11/2010 |

OTHER PUBLICATIONS

Jao, et al "[3+2] Cycloaddition of trimethylenemethane (TMM) to α,β-unsaturated γ-lactam. Preparation of 5,5-fused proline surrogates" Tetrahedron 55 (2003) 5033-5035.*

Beak, Peter, et al., "Complex Inducted Proximity Effects . . . " Journal American Chemical Society, vol. 116, pp. 3231-3239 (1994).

Bergmeier, S."Synthesis of Bicyclic Proline Anal. Using a Formal [3+2] Intramolecular Aziridine-Allylsilane . . . ", Tetrahedron, Elsevier Scie. Publ., 55, 26(1999), pp. 8025-8038.

Chen, S.H., "Synthesis and Eval. of Tripeptidyl [alpha]-Ketoamides as Human Rhinovirus 3C Protease Inhibitors", Bioorg. & Med. Chem. Letters, vol. 13, 20 (2003), pp. 3531-3536.

Esch, P.M., "Reductive Cyclization of Carbon-Centered Glycine Radicals", Tetrahedron, Elsevier Science Publishers, vol. 48, No. 22 (1992), pp. 4659-4676.

Gallagher, Donald, et al., "Complex Induced Prodimity Effects . . . " Journal of Organic Chemistry, vol. 60, pp. 7092-7093 (1995).

Gallagher, Donald, et al., "Chiral Organolithium Complexes: The Effect of Ligand Structure . . . ", Journal of Organic Chem., vol. 60, pp. 8148-8154 (1995).

(Continued)

Primary Examiner — Thomas Heard

(74) Attorney, Agent, or Firm — Honigman Miller Schwartz and Cohn LLP; Heidi M. Berven; Jonathan P. O'Brien

(57) ABSTRACT

The invention relates to compounds and processes useful for the preparation of protease inhibitors, particularly serine protease inhibitors. The protease inhibitors are useful for treatment of HCV infections.

40 Claims, No Drawings

OTHER PUBLICATIONS

Garrison, G. "Novel 3, 7-Diheterabicyclo(3.3.1) nonanes that Possess Predominant Class III Antiarrhythmic Activity in 1-4 day Post . . . " J. Med. Chem. 39, 13 (1996)pp. 2559-2570.

Kerrick, Shawn T., et al, "Asymmetric Deprotonotations: Enantioselective Syntheses . . . ", Journal of American Chemical Society, vol. 113, pp. 9708-9710 (1995).

Lamar, J., "Novel P4 Truncated Tripeptidyl Alpha-Ketoamides as HCV Protease Inhibitors", Bio. & Med. Chem. Let., vol. 14, No. 1 (2004), pp. 263-266.

Monn, J.A., "A Concise, Stereocontrolled Thiazolium Ylide Approach to Kainic Acid", J. of Organic Chem., vol. 59, No. 10 (1994), pp. 2773-2778.

Pippel, Daniel J., et al, "Complex Induced Proximity Effects: Stereoselective Carbon-Carbob Bond Formation . . . " Journal of Organic Chem., vol. 63, pp. 2-3 (1998).

Toom, L., "Microwave-Assisted Raney Nickel Reduction of Bispidinone Thioketals to N, N'-Dialkylbispidines", Synthesis, 12 (2006), pp. 2064-2068.

Yip, Y., "Discovery of a Novel Bicycloproline P2 Bearing Peptidyl .alpha.-Ketoamide LY514962 as HCV Protease Inhibitor", Bio. & Med. Chem. Let., 14(1) (2004), pp. 251-256.

Yip, Y., "P4 and P1' Optimization of Bicycloproline P2 Bearing Tetrapeptidyl Alpha-Ketoamides as HCV Protease Inhibitors", Bio. & Med. Chem. Let.,14, 9 (2004), pp. 5007-5011.

International Search Report mailed on Dec. 27, 2007 from the PCT concerning PCT/US2006/032481.

PCT/US2010/032556—International Search Report, mailed Jul. 16, 2010.

* cited by examiner

PROCESSES AND INTERMEDIATES

CROSS-REFERENCE

This application is a continuation-in-part of U.S. Ser. No. 11/506,550, filed Aug. 18, 2006, now U.S. Pat. No. 7,776,887 which claims priority under 35 U.S.C. 119(e) to U.S. Ser. Nos. 60/709,964, filed Aug. 19, 2005, and 60/810,042, filed Jun. 1, 2006, each of which is incorporated herein in its entirety.

FIELD OF THE INVENTION

This invention relates to processes and intermediates for the preparation of protease inhibitors, in particular, serine protease inhibitors.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally (A. Alberti et al., "Natural History of Hepatitis C," *J. Hepatology,* 31 (Suppl. 1), pp. 17-24 (1999)). Nearly four million individuals may be infected in the United States alone. (M. J. Alter et al., "The Epidemiology of Viral Hepatitis in the United States," *Gastroenterol. Clin. North Am.,* 23, pp. 437-455 (1994); M. J. Alter "Hepatitis C Virus Infection in the United States," *J. Hepatology,* 31 (Suppl. 1), pp. 88-91 (1999)).

Upon first exposure to HCV, only about 20% of infected individuals develop acute clinical hepatitis while others appear to resolve the infection spontaneously. In almost 70% of instances, however, the virus establishes a chronic infection that may persist for decades. (S. Iwarson, "The Natural Course of Chronic Hepatitis," *FEMS Microbiology Reviews,* 14, pp. 201-204 (1994); D. Lavanchy, "Global Surveillance and Control of Hepatitis C," *J. Viral Hepatitis,* 6, pp. 35-47 (1999)). Prolonged chronic infection can result in recurrent and progressively worsening liver inflammation, which often leads to more severe disease states such as cirrhosis and hepatocellular carcinoma. (M. C. Kew, "Hepatitis C and Hepatocellular Carcinoma", *FEMS Microbiology Reviews,* 14, pp. 211-220 (1994); I. Saito et. al., "Hepatitis C Virus Infection is Associated with the Development of Hepatocellular Carcinoma," *Proc. Natl. Acad. Sci. USA,* 87, pp. 6547-6549 (1990)). Unfortunately, there are no broadly effective treatments for the debilitating progression of chronic HCV.

Compounds described as protease inhibitors, and in particular serine protease inhibitors, useful in the treatment of HCV infections are disclosed in WO 02/18369. Also disclosed therein in this publication are processes and intermediates for the preparation of these compounds, which lead to racemization of certain steric carbon centers. See, e.g., pages 223-22. There remains however, a need for economical processes for the preparation of these compounds.

SUMMARY OF THE INVENTION

In one aspect, the invention provides processes and intermediates for producing a bicyclic pyrrolidine derivative of Formula 1, which is useful in producing protease inhibitors.

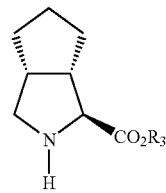

In Formula 1, $R_3$ is an acid protecting group which can be removed under acidic, basic, or hydrogenation conditions. Under acidic conditions, $R_3$ is, for example, t-butyl; under basic conditions, $R_3$ is, for example, methyl or ethyl; under hydrogenation conditions, $R_3$ is, for example, benzyl.

Another aspect of the invention includes processes and intermediates for the preparation of a compound of Formula 2, which is also useful in producing protease

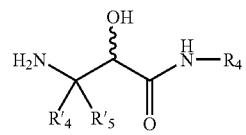

In Formula 2, $R_4$ is H, an optionally substituted aliphatic, an optionally substituted cycloaliphatic, an optionally substituted aryl, an optionally substituted aralkyl, or an optionally substituted heteroaralkyl;

$R'_4$ is H, an optionally substituted aliphatic, an optionally substituted aryl, an optionally substituted aralkyl or an optionally substituted heteroaralkyl; and $R'_5$ is an optionally substituted aliphatic, an optionally substituted cycloaliphatic, an optionally substituted aryl, an optionally substituted aralkyl, or an optionally substituted heteroaralkyl; or $R'_4$ and $R'_5$ together with the atom to which they are attached may form a 3- to 7-membered optionally substituted cycloaliphatic ring.

The processes and intermediates described herein are also useful for a process for preparing a protease-inhibiting compound of Formula 3 shown below.

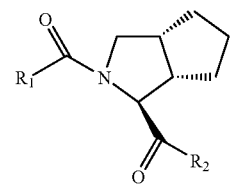

Referring to Formula 3, $R_1$ is RW—, $P_2$—, $P_3$-$L_2$-$P_2$—, or $P_4$-$L_3$-$P_3$-$L_2$-$P_2$—;

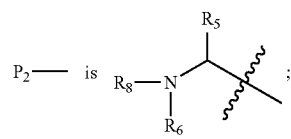

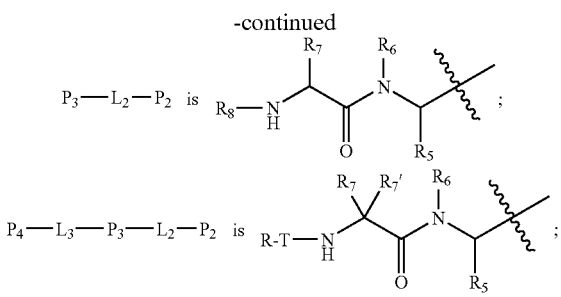

W is a bond, —CO—, —O—CO—, —NR$^X$—, —NR$^X$—CO—, —O—, or —S—;

T is —C(O)—, —O—C(O)—, —NHC(O)—, —C(O)C(O)—, or —SO$_2$—;

R is H, an optionally substituted aliphatic, an optionally substituted cycloaliphatic, optionally substituted heterocycloaliphatic, an optionally substituted aryl, or an optionally substituted heteroaryl;

R$_5$ is H, an aliphatic, a cycloaliphatic, a heterocycloaliphatic, an aryl, or a heteroaryl; each of which, except for H, is optionally substituted with one or more substituents each independently selected from Group J, wherein Group J includes halo, cycloaliphatic, aryl, heteroaryl, alkoxy, aroyl, heteroaroyl, acyl, nitro, cyano, amido, amino, sulfonyl, sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, and hydroxy;

R$_6$ is an optionally substituted aliphatic, an optionally substituted heteroalkyl, an optionally substituted heteroaryl, an optionally substituted phenyl; or R$_5$ and R$_6$, together with the atoms to which they are attached, may form a 5- to 7-membered, optionally substituted monocyclic heterocycle, or a 6- to 12-membered, optionally substituted bicyclic heterocycle, in which each heterocycle ring optionally contains an additional heteroatom selected from —O—, —S—, or —NR$^X$—;

Each of R$_7$ and R$_7$' is independently H, an optionally substituted aliphatic, an optionally substituted heteroalkyl, an optionally substituted heteroaryl, or an optionally substituted phenyl; or R$_7$ and R$_7$', together with the atom to which they are attached, may form a 3- to 7-membered cycloaliphatic or heterocycloaliphatic ring; or R$_7$ and R$_6$, together with the atoms to which they are attached, may form a 5- to 7-membered optionally substituted monocyclic heterocycle, a 5- to 7-membered optionally substituted monocyclic aryl, a 6- to 12-membered optionally substituted bicyclic heterocycle, or a 6- to 12-membered optionally substituted bicyclic aryl, in which each heterocycle or aryl ring optionally contains an additional heteroatom selected from —O—, —S—, or —NR$^X$—; or When R$_5$ and R$_6$ together with the atoms to which they are attached form a ring, R$_7$ and the ring system formed by R$_5$ and R$_6$ may form an 8- to 14-membered optionally substituted bicyclic fused ring system, wherein the bicyclic fused ring system may further fuse with an optionally substituted phenyl to form an optionally substituted 10- to 16-membered tricyclic fused ring system;

R$_8$ is H or a protecting group;

R$^X$ is H, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (aliphatic)carbonyl, (heterocycloaliphatic)carbonyl, ((heterocycloaliphatic)aliphatic)carbonyl, (heteroaryl)carbonyl, or (heteroaralphatic)carbonyl;

R$_2$ is —(NH—CR$_4$'R$_5$'—C(O)—C(O))—NHR$_4$ or —(NH—CR$_4$'R$_5$'—CH(OH)—C(O))—NHR$_4$;

R$_4$ is H, an optionally substituted aliphatic, an optionally substituted cycloaliphatic, an optionally substituted heterocycloaliphatic, an optionally substituted aryl, an optionally substituted aralkyl or an optionally substituted heteroaralkyl; and Each of R'$_4$ and R'$_5$ is independently H, an optionally substituted aliphatic, an optionally substituted cycloaliphatic, an optionally substituted heterocycloaliphatic, an optionally substituted aryl, an optionally substituted aralkyl, an optionally substituted heteroaralkyl, or an optionally substituted heteroaralkyl; or R$_4$' and R$_5$', together with the atom to which they are attached, may form a 3- to 7-membered optionally substituted cycloaliphatic ring.

In some embodiments, the process for preparing compounds of Formula 3 includes the step of carboxylation of an azabicyclooctane of Formula 6,

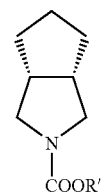

wherein R' is a C$_{1-5}$ alkyl, to give a racemic mixture of cis- and trans-octahydrocyclopenta[c]pyrrole-1-carboxylic acids of Formula 7

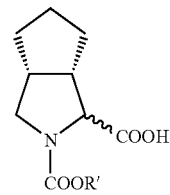

In some embodiments, each of P$_2$, P$_3$ and P$_4$ is independently a bond, H, an optionally substituted aliphatic, an optionally substituted aryl, an optionally substituted heteroaryl, an optionally substituted alkoxy, an optionally substituted alkylsufanyl, an optionally substituted aralkoxy, an optionally substituted aralkylsulfanyl, an optionally substituted mono- or dialkylamino, an optionally substituted mono- or diarylamino, or an optionally substituted mono- or diheteroarylamino.

In some embodiments, each of L$_2$ and L$_3$ is independently a bond, —C(O)—, or —SO$_2$—.

In some embodiments, R$_5$ is a C$_{1-6}$ alkyl, C$_{3-10}$ cycloalkyl, C$_{3-10}$ cycloalkyl-C$_{1-12}$ alkyl, C$_{6-10}$ aryl, C$_{6-10}$ aryl-C$_{1-6}$ alkyl, C$_{3-10}$ heterocyclyl, C$_{6-10}$ heterocyclyl-C$_{1-6}$ alkyl, C$_{5-10}$ heteroaryl, or C$_{5-10}$ heteroaryl-C$_{1-6}$ alkyl; each of which is optionally substituted with one to three substituents each independently selected from Group J; and up to three aliphatic carbon atoms in R$_5$ may be independently replaced by a heteroatom or group selected from O, NH, S, SO, or SO$_2$, in a chemically stable arrangement.

In some further embodiments, $R_5$ is

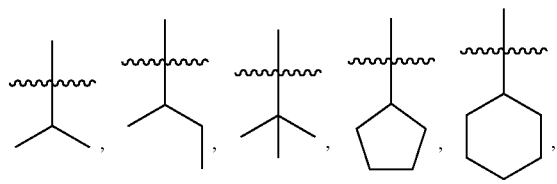

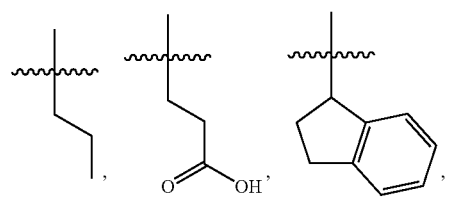

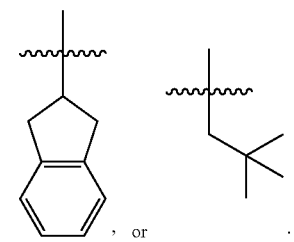

, or

In some embodiments, $R_7'$ is H; $R_7$ is a $C_{1-6}$ alkyl, $C_{3-10}$ cycloalkyl, $C_{3-10}$ cycloalkyl-$C_{1-12}$ alkyl, $C_{6-10}$ aryl, $C_{6-10}$ aryl-$C_{1-6}$ alkyl, $C_{3-10}$ heterocyclyl, $C_{6-10}$ heterocyclyl-$C_{1-6}$ alkyl, $C_{5-10}$ heteroaryl, or $C_{5-10}$ heteroaryl-$C_{1-6}$ alkyl; and $R_1$ is optionally substituted with one to three substituents each independently selected from Group J; and up to three aliphatic carbon atoms in $R_1$ may be replaced by a heteroatom or group selected from O, NH, S, SO, or $SO_2$ in a chemically stable arrangement.

In some further embodiments, $R_7$ is

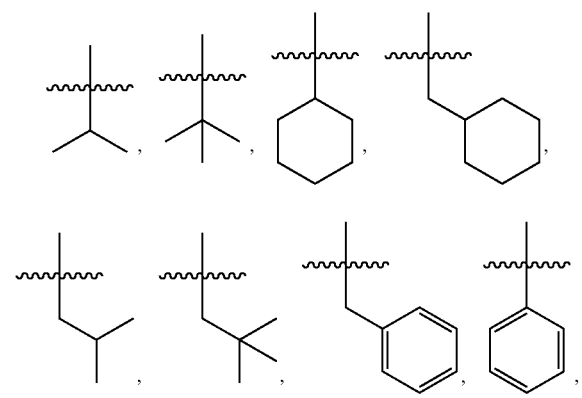

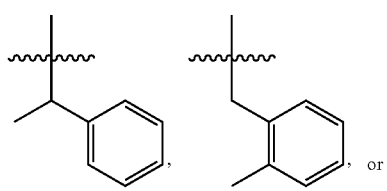

, or

-continued

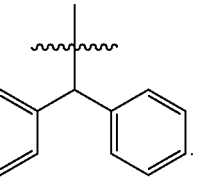

In still some further embodiments, $R_7$ and $R_7'$, together with the atom to which they are attached, form

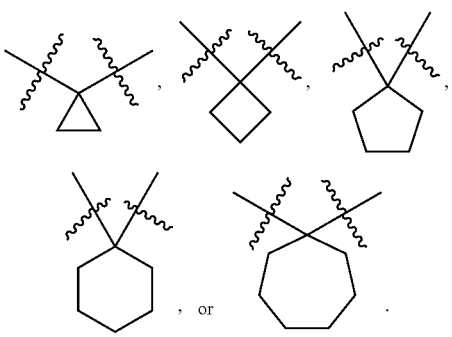

, or

In some embodiments, R is a $C_{6-10}$ aryl, $C_{6-10}$ aryl-$C_{1-12}$ aliphatic, $C_{1-10}$ cycloalkyl, $C_{3-10}$ cycloalkenyl, $C_{3-10}$ cycloalkyl-$C_{1-12}$ aliphatic, $C_{3-10}$ cycloalkenyl-$C_{1-12}$ aliphatic, $C_{3-10}$ heterocyclyl, $C_{3-10}$ heterocyclyl-$C_{1-12}$ aliphatic, $C_{5-10}$ heteroaryl, or $C_{5-10}$ heteroaryl-$C_{1-12}$ aliphatic; each of which is optionally substituted with one to three substituents each independently selected from Group J.

In some further embodiments, R is

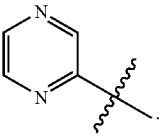

In still some further embodiments, R is

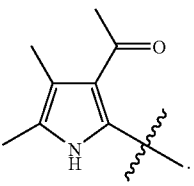 [SMILES: *c1[nH]c(C)c(C)c1C(C)=O]

In yet still some further embodiments, R is

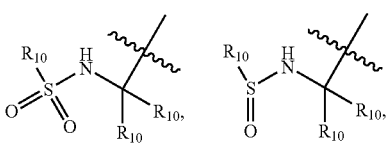

-continued
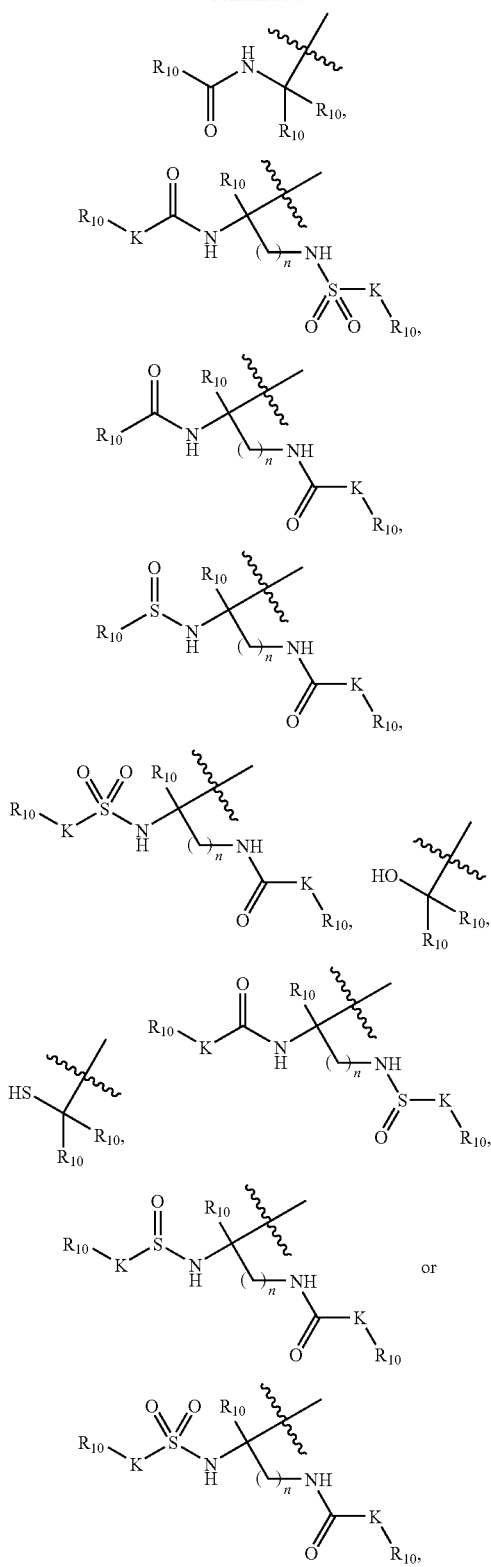
and $R_{10}$ is H, $C_{1-12}$ aliphatic, $C_{6-10}$ aryl, $C_{6-10}$ aryl-$C_{1-12}$ aliphatic, $C_{3-10}$ cycloalkyl, $C_{3-10}$ cycloalkenyl, $C_{3-10}$ cycloalkyl-$C_{1-12}$ aliphatic, $C_{3-10}$ cycloalkenyl-$C_{1-12}$ aliphatic, $C_{3-10}$ heterocyclyl, $C_{3-10}$ heterocyclyl-$C_{1-12}$ aliphatic, $C_{5-10}$ heteroaryl, or $C_{5-10}$ heteroaryl-$C_{1-12}$ aliphatic.
In still some further embodiments, R is
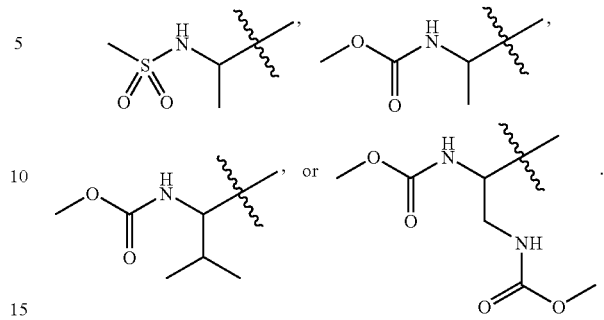
In yet still some further embodiments, R is
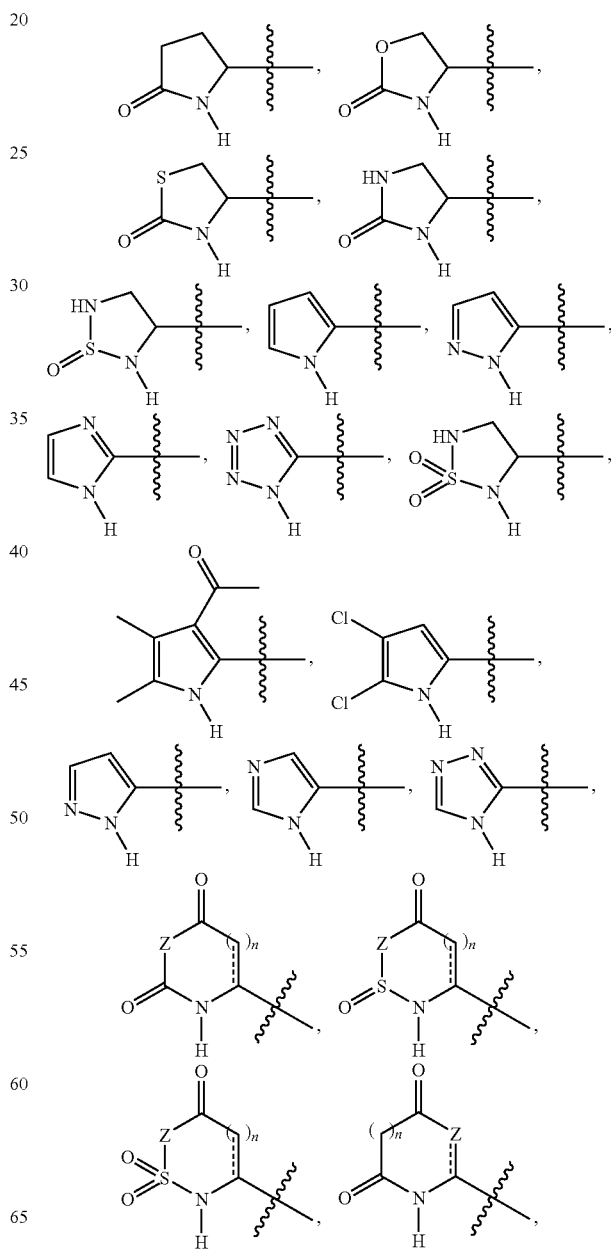

-continued
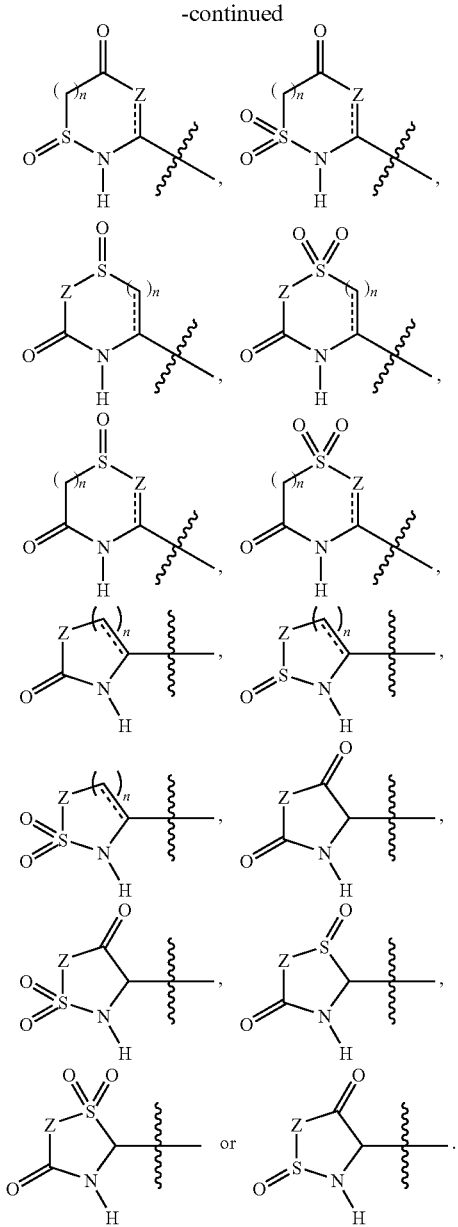
In some further embodiments, R is
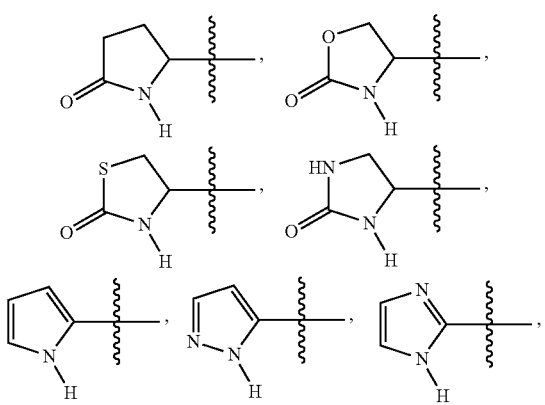
-continued
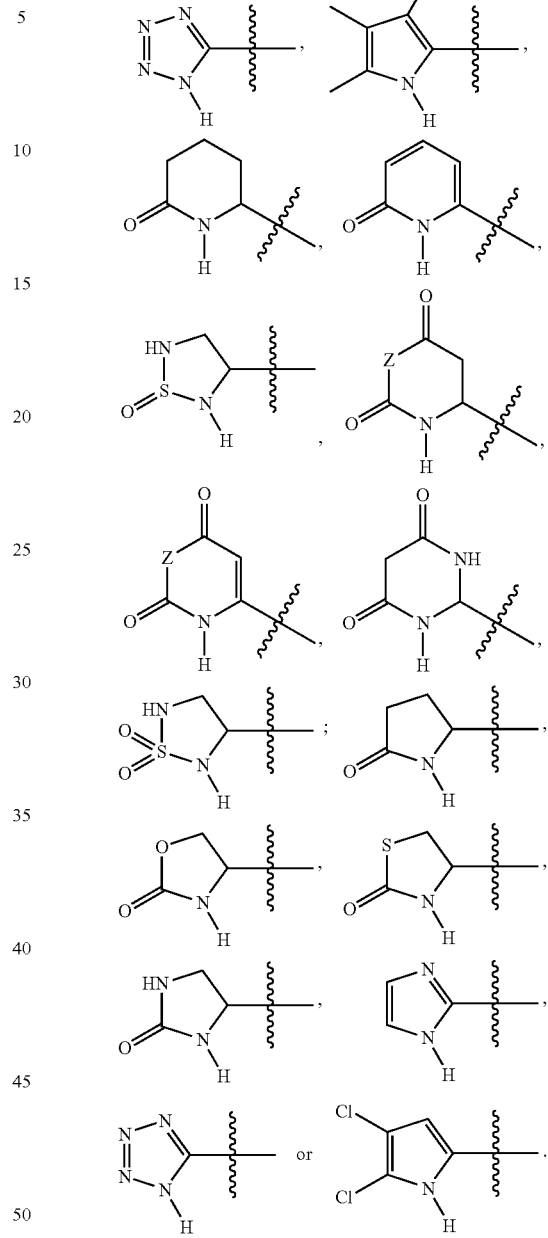
In some embodiments, the carboxylation step in the process for preparing compounds of Formula 3 includes forming a 2-anion of the compound of Formula 6
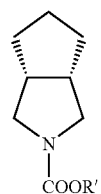
6 in the presence of a complexing agent, and then treating the 2-anion with carbon dioxide to produce a racemic mixture of trans-/cis-octahydrocyclopenta[c]pyrrole-1-carboxylic acids of Formula 7

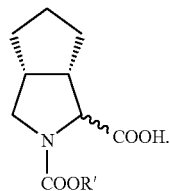

In some further embodiments, the 2-anion of the compound of Formula 6 is prepared by treating the compound of Formula 6 with a strong lithium base in the presence of a complexing agent and an aprotic solvent.

In still some further embodiments, the base used in preparing the 2-anion is sec-butyl lithium.

In still some further embodiments, the complexing agent used in preparing the 2-anion is tetramethylethylenediamine, tetraethylethylenediamine, tetramethyl-1,2-cyclohexyldiamine, sparteine, or a 3,7-di($C_{1-6}$ alkyl)-3,7-diazabicyclo[3.3.1]nonane such as, for example, 3,7-di(n-propyl)-3,7-diazabicyclo[3.3.1]nonane.

In still some further embodiments, the complexing agent is tetramethylethylenediamine, tetraethylethylenediamine, tetramethyl-1,2-cyclohexyldiamine, or 3,7-di($C_{1-6}$ alkyl)-3,7-diazabicyclo[3.3.1]nonane.

In still some further embodiments, the complexing agent is D-sparteine.

In some embodiments, the trans-/cis-ratio in the racemic mixture of compounds of Formula 7 is 1 to 2.

In some embodiments, the trans-/cis-ratio in the racemic mixture of compounds of Formula 7 is 40 to 60.

In still some further embodiments, the trans-/cis-ratio in the racemic mixture of compounds of Formula 7 is 1 to 1.

In still some further embodiments, the trans-/cis-ratio is 60 to 40.

In still some further embodiments, the trans-/cis-ratio is 80 to 20.

In still some further embodiments, the trans-/cis-ratio is 90 to 10.

In still some further embodiments, the trans-/cis-ratio is greater than 98 to 2.

In some other embodiments, the process for preparing compounds of Formula 3 further includes equilibrating a trans-/cis-mixture of the compounds of Formula 7

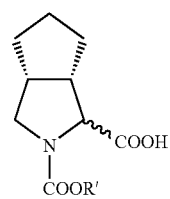

in the presence of a suitable base to produce a predominantly trans-cis racemic acid of Formula 8

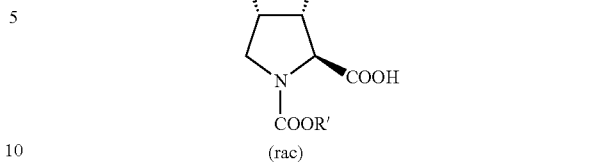

wherein the trans-/cis-ratio is greater than 80 to 20.

In some other embodiments, the process for preparing compounds of Formula 3 further includes equilibrating a trans-/cis-mixture of the compounds of Formula 7 in the presence of a suitable base to produce a predominantly trans-cis racemic acid of Formula 8 wherein the trans-/cis-ratio is greater than 90 to 10.

In some other embodiments, the process for preparing compounds of Formula 3 further includes equilibrating a trans/cis-mixture of Formula 7 in the presence of a suitable base to produce a predominantly trans-cis racemic acid of Formula 8 wherein the trans-/cis-ratio is greater than 98 to 2.

In some further embodiments, the base used in equilibrating the trans/cis-mixture of Formula 7 is lithium hexamethyldisilazide, lithium di-isopropylamide, or lithium 2,2,6,6-tetramethylpiperidide.

In some further embodiments, the base is lithium hexamethyldisilazide.

In some further embodiments, the base is sec-butyl lithium and the complexing agent is 3,7-dipropyl-3,7-diazabicyclo[3.3.1]nonane to give a mixture of racemic trans-/cis-N-alkoxycarbonyl-octahydrocyclopenta[c]pyrrole-1-carboxylic acids of Formula 7, in which the trans/cis-ratio is greater than 90 to 10.

In some further embodiments, the trans-N-alkoxycarbonyl-octahydrocyclopenta[c]pyrrole-1-carboxylic acid is trans-N-t-butoxycarbonyl-octahydrocyclopenta[c]pyrrole-1-carboxylic acid.

In some other embodiments, the process for preparing compounds of Formula 3 further includes resolving racemic trans-N-alkoxycarbonyl-octahydrocyclopenta[c]pyrrole-1-carboxylic acid to produce a (1S,2S,3R) trans-N-alkoxycarbonyl-octahydrocyclopenta[c]pyrrole-1-carboxylic acid.

In some further embodiments, the resolution of a racemic mixture of compounds includes the steps of 1) forming a salt with an optically active base; and ii) crystallizing the salt formed by step i) to provide an optically active salt of Formula 9.

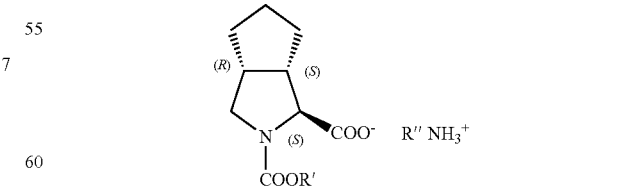

In some further embodiments, the optically active base used in resolving a racemic mixture of compounds is (R) α-aminoethylbenzene.

In some further embodiments, the optically active base is (S) 1,2,3,4-tetrahydro-1-naphthylamine.

In some further embodiments, the process for preparing compounds of Formula 3 further includes the steps of esterifying the carboxylic acid of Formula 9 with a compound containing the $R_3$ group; and removing the —COOR' protecting group to produce a compound of Formula 1,

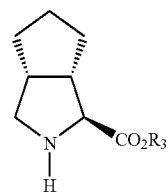

1 wherein $R_3$ is an optionally substituted alkyl or aralkyl.

In still some further embodiments, $R_3$ is t-butyl.

In some embodiments, the process for preparing compounds of Formula 3 further includes reacting the aminoester of Formula 1 with $R_1$COOH in the presence of a coupling reagent to produce a compound of Formula 1a.

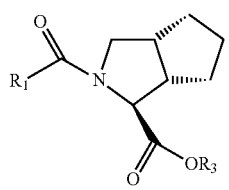

1a

In some embodiments, the reaction between the aminoester of Formula 1 and $R_1$COOH can be carried out further in the presence of histamine, glycine, or lysine, in addition to a coupling agent.

In some further embodiments, $R_1$ is $P_2$—.

In some further embodiments, $R_1$ is $P_3$-$L_2$-$P_2$—.

In some further embodiments, $R_1$ is $P_4$-$L_3$-$P_3$-$L_2$-$P_2$—.

In some further embodiments, $R_1$ is RW—.

In some embodiments, the process for preparing compounds of Formula 3 further includes the steps of hydrolyzing the ester of a compound of Formula 1a; to provide a carboxylic acid and reacting the carboxylic acid thus obtained with a compound containing the $R_2$ group, wherein $R_2$ is —(NH—$CR_4'R_5'$—CH(OH)C(O))—$NHR_4$, in the presence of a coupling reagent to produce the compound of Formula 3.

In some further embodiments, $R_4$ is H, an optionally substituted aliphatic, optionally substituted cycloaliphatic, an optionally substituted aryl, an optionally substituted heteroaryl, an optionally substituted aralkyl, or an optionally substituted heteroaralkyl;

$R_4'$ is H, an optionally substituted aliphatic, an optionally substituted aryl, an optionally substituted aralkyl, or an optionally substituted heteroaralkyl; and $R_5'$ is H, an optionally substituted aliphatic, an optionally substituted cycloaliphatic, an optionally substituted aryl, an optionally substituted aralkyl, or an optionally substituted heteroaralkyl; or $R_4'$ and $R_5'$, together with the atom to which they are attached, form a 3- to 7-membered optionally substituted cycloaliphatic ring.

In some further embodiments, $R_2$ is

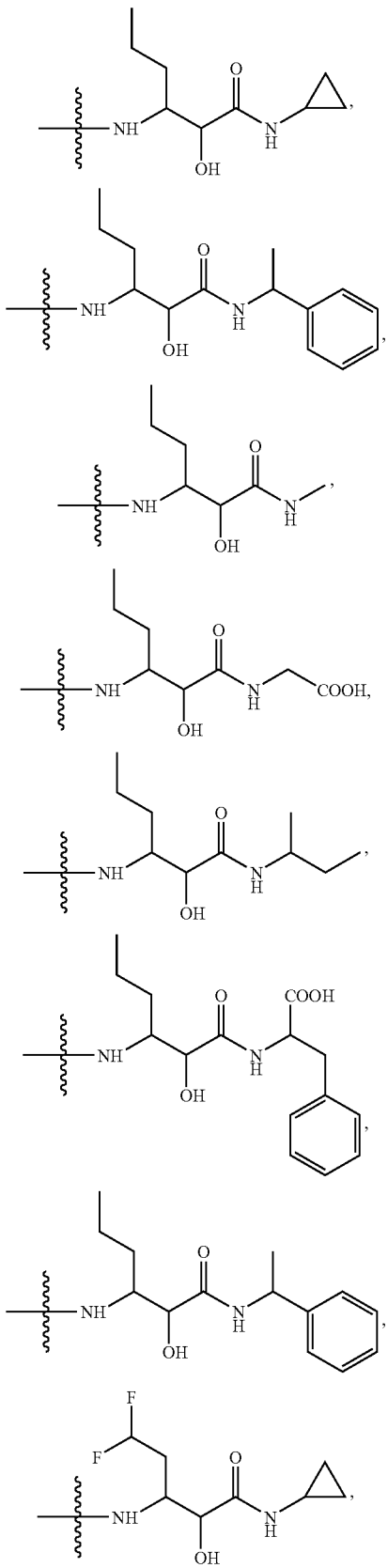

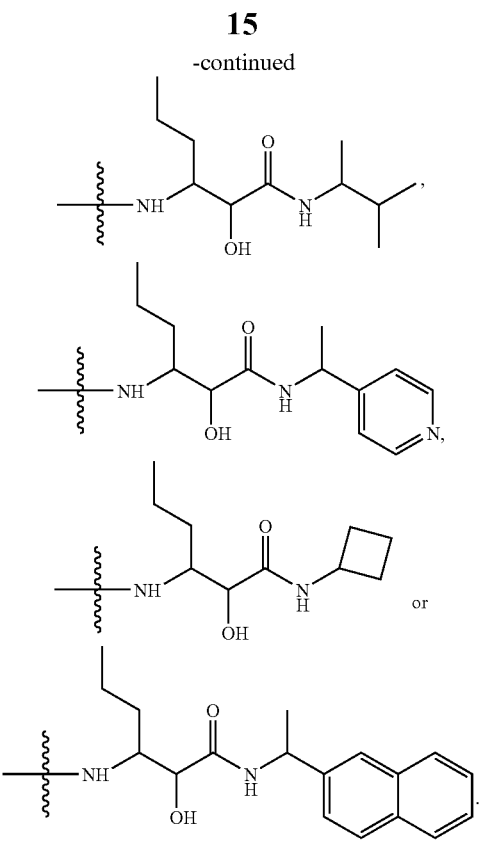

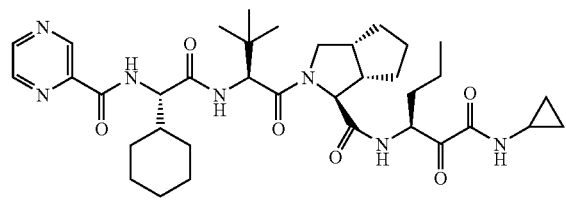

The invention further relates to a process for preparing a compound of Formula 4

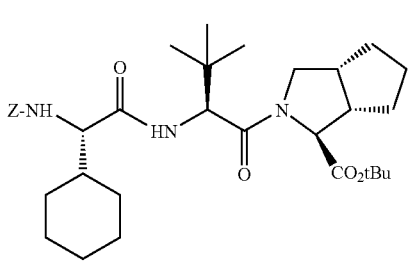

In some embodiments, the process for preparing compounds of Formula 4 includes the steps of:

i) providing an N-alkoxycarbonyl-3-azabicyclo[3.3.0]octane;

ii) forming a 2-anion of the N-alkoxycarbonyl-3-azabicyclo[3.3.0]octane in the presence of a chelating agent;

iii) treating the anion of step ii) with carbon dioxide to produce a cis-/trans-mixture of N-alkoxycarbonyl-octahydrocyclopenta[c]pyrrole-1-carboxylic acids;

iv) treating the mixture of step iii) with a strong base to produce an essentially pure trans-N-alkoxycarbonyl-octahydrocyclopenta[c]pyrrole-1-carboxylic acid;

v) forming a salt of the carboxylic acid with an optically active amine;

vi) crystallizing the salt; vii) esterifying the salt provided in step vi);

viii) removing the N-alkoxycarbonyl group to produce (1S,3aR,6aS)-1-butyl-octahydrocyclopenta[c]pyrrole-1-carboxylate, t-butyl ester;

ix) reacting the bicyclic of step viii) with a protected amino acid of Formula 26,

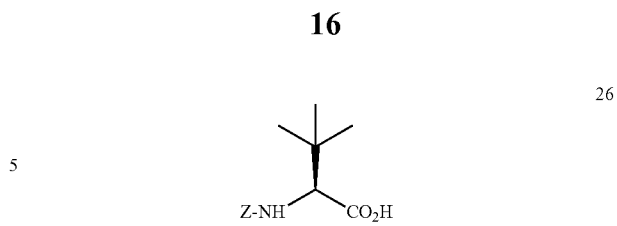

wherein Z is an amine protecting group, in the presence of a coupling reagent, to produce an amide-ester of Formula 27;

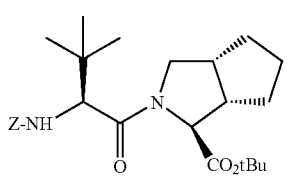

x) removing the protecting group Z from the amide-ester of step ix) to produce the amino compound of Formula 28;

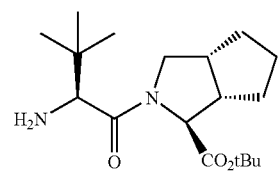

xi) reacting the amino compound of Formula 28 with a protected amino acid of Formula 29

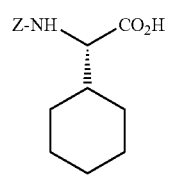

in the presence of a coupling reagent to produce a tripeptide of Formula 30;

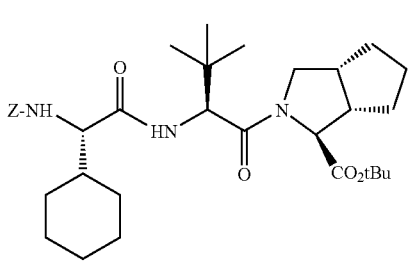

xii) removing the protecting group Z in the tripeptide of Formula 30 to produce a free amino-tripeptide of Formula 31;

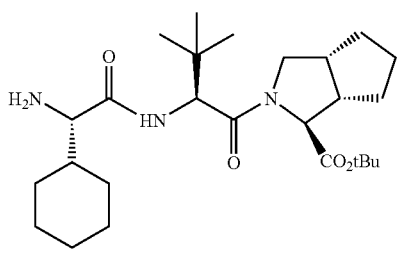

31 xiii) reacting the amino-tripeptide of Formula 31 with pyrazine-2-carboxylic acid in the presence of a coupling reagent to produce an amide-tripeptide ester of Formula 33;

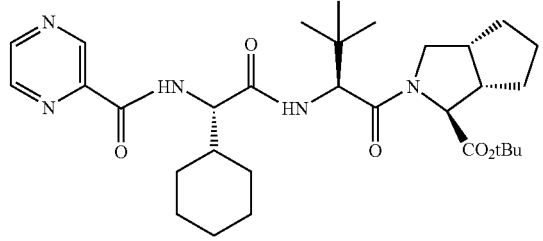

33 xiv) hydrolyzing the ester of the amide-tripeptide ester of Formula 33 to produce an amide-tripeptide acid of Formula 34;

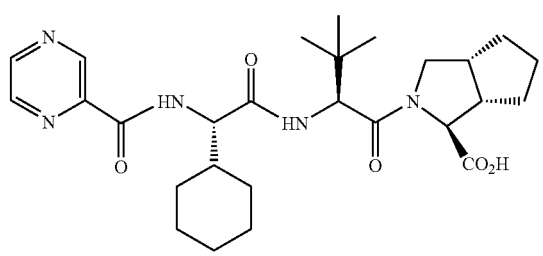

34 xv) reacting the amide-tripeptide acid of Formula 34 with an aminohydroxy-amide of Formula 18

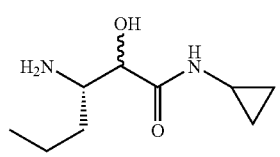

18 in the presence of a coupling reagent to produce a hydroxy-tetrapeptide of Formula 35; and

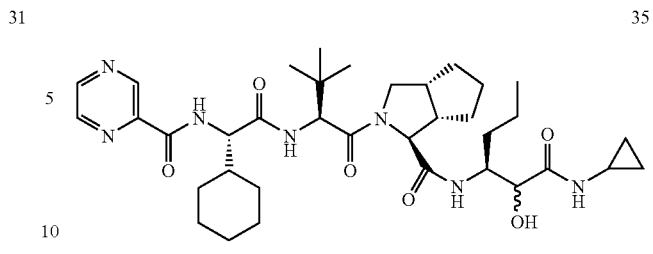

35 xvi) oxidizing the hydroxy group of Formula 35 to produce the compound of Formula 4.

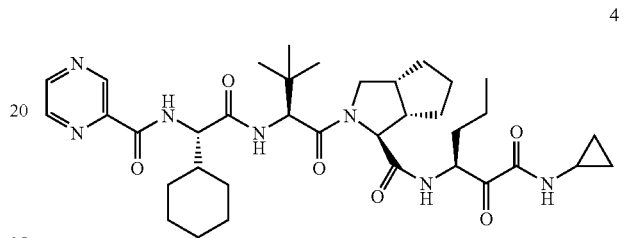

4

In some embodiments, the oxidizing reagent used in step xvi) described above is sodium hypochlorite, and the oxidation is carried out in the presence of 2,2,6,6-tetramethylpiperidinyloxy free radical (TEMPO).

In some other embodiments, the oxidizing reagent used in step xvi) described above is 1,1-dihydro-1,1,1-triacetoxy-1,2-benzoiodooxol-3(1H)-one, In some further embodiments, the process further includes dissolving the compound of Formula 4 in an organic solvent to obtain its solution, and then adding an acid to the solution. A suitable organic solvent can be any solvent in which the compound of Formula 4 dissolves, e.g., methylene chloride. The acid can be any acid, inorganic or organic, e.g., acetic acid or propionic acid.

In still some further embodiments, the process further includes concentrating the solution of the compound of Formula 4 to obtain the compound in a solid form. Such a concentrating process can be, e.g., distillation of the solvent under reduced pressure (e.g., vacuum) by natural evaporation of the solvent. The solid form in which the compound of Formula 4 is obtained can be, e.g., crystalline or semicrystalline, and can be of higher purity than that before being dissolved into an organic solvent and then concentrated in acid condition.

As such, the invention also relates to a process of purifying the compound of Formula 4.

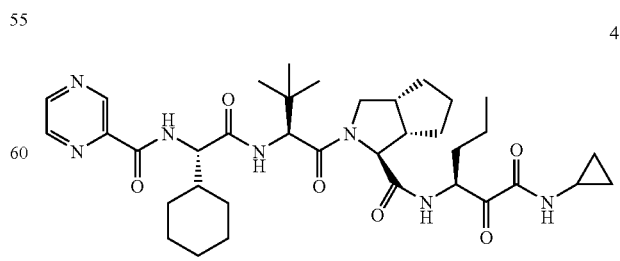

4

In some embodiments, the process includes first dissolving the compound of Formula 4 in an organic solvent to obtain its solution, adding an acid to the solution of the compound of Formula 4, and then concentrating the solution of the compound of Formula 4 to obtain the compound in a solid form. Examples of suitable organic solvents, acids, and solid forms have been provided above.

The invention further features compounds of Formula 1a,

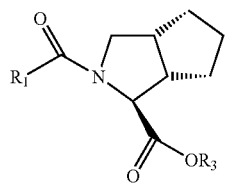

1a

Wherein $R_1$ is $P_2$—;

$P_2$— is

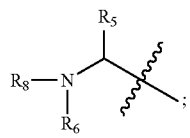

$R_5$ is H, an aliphatic, a cycloaliphatic, a heterocycloaliphatic, an aryl, or a heteroaryl; each of which, except for H, is optionally substituted with one or more substituents each independently selected from Group J consisting of halo, cycloaliphatic, aryl, heteroaryl, alkoxy, aroyl, heteroaroyl, acyl, nitro, cyano, amido, amino, sulfonyl, sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, and hydroxy;

$R_6$ is an optionally substituted aliphatic, an optionally substituted heteroalkyl, an optionally substituted heteroaryl, an optionally substituted phenyl; or $R_5$ and $R_6$, together with the atoms to which they are attached, may form a 5- to 7-membered, optionally substituted monocyclic heterocycle, or a 6- to 12-membered, optionally substituted bicyclic heterocycle, in which each heterocycle ring optionally contains an additional heteroatom selected from —O—, —S—, or —$NR^X$—;

$R^X$ is H, aliphatic, cycloaliphatic, (cycloaliphatic)aliphatic, aryl, aralphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (aralphatic)carbonyl, (heterocycloaliphatic)carbonyl, ((heterocycloaliphatic)aliphatic)carbonyl, (heteroaryl)carbonyl, or (heteroaralphatic)carbonyl;

$R_8$ is H or a protecting group; and $R_3$ is an optionally substituted alkyl.

In some embodiments, $R_3$ is t-butyl.

In some other embodiments, $P_2$— is

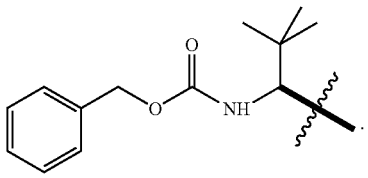 [SMILES: *[C@@H](NC(=O)OCc1ccccc1)C(C)(C)C]

In some further embodiments, $P_2$— is

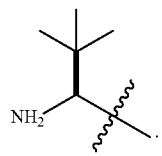

The invention further relates to compounds of Formula 1a show above, in which $R_1$ is $P_3$-$L_2$-$P_2$—;

$P_3$-$L_2$-$P_2$— is

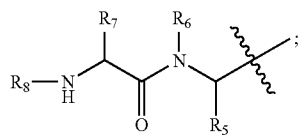

$R_5$ is H, an aliphatic, a cycloaliphatic, a heterocycloaliphatic, an aryl, or a heteroaryl; each of which, except for H, is optionally substituted with one or more substituents each independently selected from Group J consisting of halo, cycloaliphatic, aryl, heteroaryl, alkoxy, aroyl, heteroaroyl, acyl, nitro, cyano, amido, amino, sulfonyl, sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, and hydroxy;

$R_6$ is an optionally substituted aliphatic, an optionally substituted heteroalkyl, an optionally substituted heteroaryl, an optionally substituted phenyl; or $R_5$ and $R_6$, together with the atoms to which they are attached, may form a 5- to 7-membered, optionally substituted monocyclic heterocycle, or a 6- to 12-membered, optionally substituted bicyclic heterocycle, in which each heterocycle ring optionally contains an additional heteroatom selected from —O—, —S—, or —$NR^X$—;

$R_7$ is H, an optionally substituted aliphatic, an optionally substituted heteroalkyl, an optionally substituted heteroaryl, or an optionally substituted phenyl; or $R_7$ and $R_6$, together with the atoms to which they are attached, may form a 5- to 7-membered optionally substituted monocyclic heterocycle, a 5- to 7-membered optionally substituted monocyclic aryl, a 6- to 12-membered optionally substituted bicyclic heterocycle, or a 6- to 12-membered optionally substituted bicyclic aryl, in which each heterocycle or aryl ring optionally contains an additional heteroatom selected from —O—, —S—, or —$NR^X$—; or When $R_5$ and $R_6$ together with the atoms to which they are attached form a ring, $R_7$ and the ring system formed by $R_5$ and $R_6$ may form an 8- to 14-membered optionally substituted bicyclic fused ring system, wherein the bicyclic fused ring system may further fuse with an optionally substituted phenyl to form an optionally substituted 10- to 16-membered tricyclic fused ring system;

$R^x$ is H, aliphatic, cycloaliphatic, (cycloaliphatic)aliphatic, aryl, araliphatic, heterocycloaliphatic, (heterocycloaliphatic) aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic) carbonyl, (heterocycloaliphatic)carbonyl, ((heterocycloaliphatic)aliphatic)carbonyl, (heteroaryl)carbonyl, or (heteroaraliphatic)carbonyl;

$R_8$ is H or a protecting group; and $R_3$ is an optionally substituted alkyl.

In some embodiments, $R_3$ is t-butyl.

In some embodiments, $P_3$-$L_2$-$P_2$— is

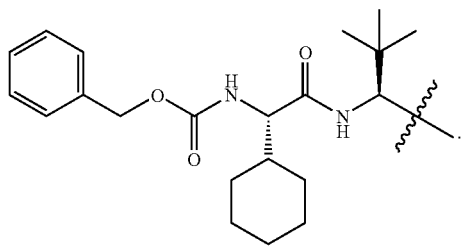 [SMILES: *[C@@H](NC(=O)[C@@H](NC(=O)OCc1ccccc1)C1CCCCC1)C(C)(C)C]

In some embodiments, $P_3$-$L_2$-$P_2$— is

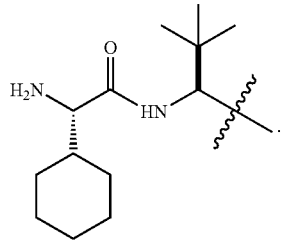 [SMILES: *[C@@H](NC(=O)[C@@H](N)C1CCCCC1)C(C)(C)C]

Also within the scope of the present invention are the compounds of 3,7-dipropyl-3,7-diazabicyclo[3.3.1]nonane, and 3,7-dipropyl-3,7-diazabicyclo[3.3.1]nonan-9-one.

In one aspect, the invention includes a process for preparing a racemic mixture of cis and trans-octahydrocyclopenta[c]pyrrole-1-carboxylic acids of Formula 7

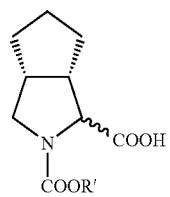

comprising the step of carboxylation of an azabicyclooctane of Formula 6,

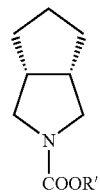

wherein R' is $C_{1-5}$ alkyl.

In one embodiment, the carboxylation step includes forming a 2-anion of the compound of Formula 6

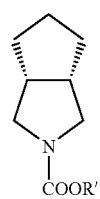

in the presence of a complexing agent, and treating the 2-anion with carbon dioxide to produce a racemic mixture of trans-/cis-octahydrocyclopenta[c]pyrrole-1-carboxylic acids of Formula 7.

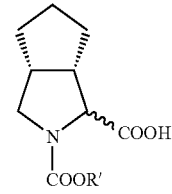

In another embodiment, the 2-anion is prepared by treating the compound of Formula 6 with a strong lithium base in the presence of a complexing agent and an aprotic solvent.

In a further embodiment, the base is sec-butyl lithium.

In a further embodiment, the complexing agent is tetramethylethylenediamine, tetraethylethylenediamine, tetramethyl-1,2-cyclohexyldiamine, sparteine, or 3,7-dipropyl-3,7-diazabicyclo[3.3.1]nonane.

In one embodiment, the complexing agent is tetramethylethylenediamine, tetraethylethylenediamine, tetramethyl-1, 2-cyclohexyldiamine, or 3,7-dipropyl-3,7-diazabicyclo [3.3.1]nonane.

In one embodiment, the trans-/cis-ratio is 1 to 1.

In another embodiment, the trans-/cis-ratio is 60 to 40.

In another embodiment, the trans-/cis-ratio is 80 to 20.

In another embodiment, the trans-/cis-ratio is 90 to 10.

In yet another embodiment, the trans-/cis-ratio is greater than 98 to 2.

In one embodiment, the complexing agent is D-sparteine,

In one embodiment, the lithium base is sec-butyl lithium and the complexing agent is 3,7-dipropyl-3,7-diazabicyclo[3, 3,1]nonane to give a mixture of racemic trans-/cis-N-alkoxycarbonyl-octahydrocyclopenta[c]pyrrole-1-carboxylic acids of Formula 7, in which the trans-/cis-ratio is greater than 90 to 10.

In a further embodiment, the trans-N-alkoxycarbonyl-octahydrocyclopenta[c]pyrrole-1-carboxylic acid is trans-N-t-butoxycarbonyl-octahydrocyclopenta[c]pyrrole-1-carboxylic acid.

In one aspect, the invention includes a process for preparing a compound of Formula 4

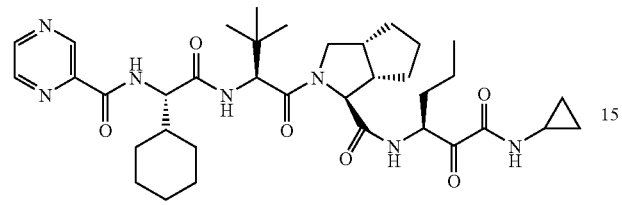

4 comprising the steps of:

i) providing an N-alkoxycarbonyl-3-azabicyclo[33.0]octane;

ii) forming a 2-anion of the N-alkoxycarbonyl-3-azabicyclo[3.3.0]octane in the presence of a chelating agent;

iii) treating the anion of step ii) with carbon dioxide to produce a cis-/trans-mixture of N-alkoxycarbonyl-octahydrocyclopenta[c]pyrrole-1-carboxylic acids;

iv) treating the mixture of step iii) with a strong base to produce an essentially pure trans-N-alkoxycarbonyl-octahydrocyclopenta[c]pyrrole-1-carboxylic acid;

v) forming a salt with an optically active amine;

vi) crystallizing the salt;

vii) esterifying the acid provided in step vi);

viii) removing the N-alkoxycarbonyl group to produce (1S, 3aR,6aS)-t-butyl-octahydrocyclopenta[c]pyrrole-1-carboxylate, t-butyl ester;

ix) reacting the bicyclic aminoester of step viii) with a protected amino acid of Formula 26,

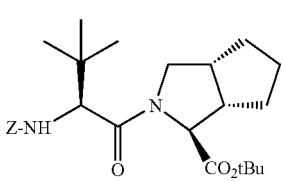

26 wherein Z is an amine protecting group, in the presence of a coupling reagent, to produce an amide-ester of Formula 27;

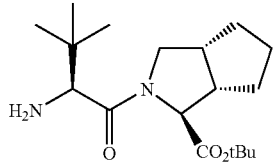

27 x) removing the protecting group Z from the amide-ester of step ix) to produce the amino compound of Formula 28;

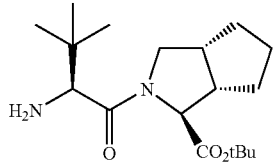

28 xi) reacting the amino compound of Formula 28 with a protected amino acid of Formula 29

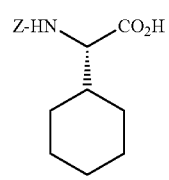

29 in the presence of a coupling reagent to produce a tripeptide of Formula 30;

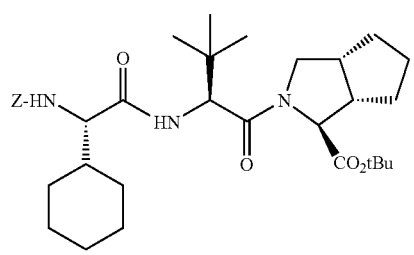

30 xii) removing the protecting group Z in the tripeptide of Formula 30 to produce a free amino-tripeptide of Formula 31;

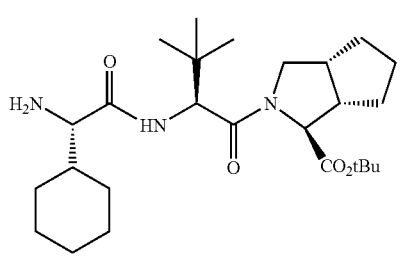

31 xiii) reacting the amino-tripeptide of Formula 31 with pyrazine-2-carboxylic acid in the presence of a coupling reagent to produce an amide-tripeptide ester of Formula 33;

33

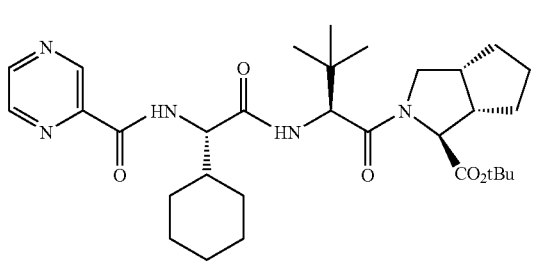

xiv) hydrolyzing the ester of the amide-tripeptide ester of Formula 33 to produce an amide-tripeptide acid of Formula 34;

34

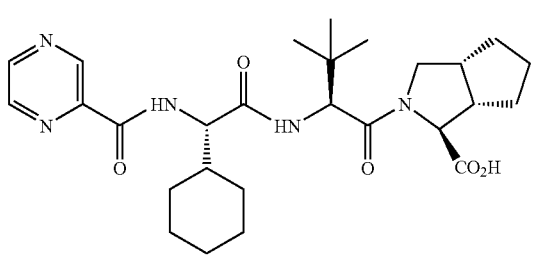

xv) reacting the amide-tripeptide acid of Formula 34 with an aminohydroxy-amide of Formula 18

18

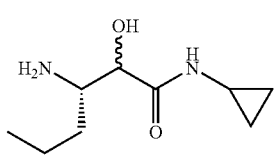

in the presence of a coupling reagent to produce a hydroxy-tetrapeptide of Formula 35; and

35

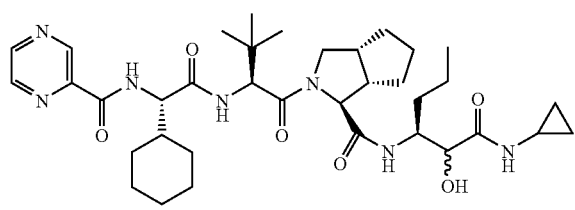

xvi) oxidizing the hydroxy group of Formula 35 to produce the compound of Formula 4.

4

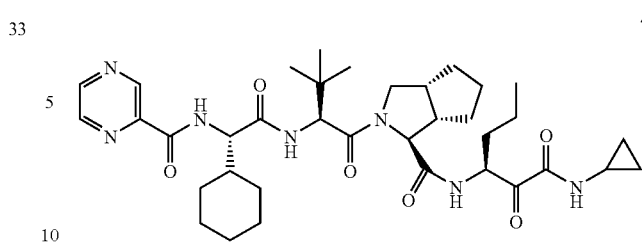

In one embodiment, the oxidizing reagent used in step xvi) is sodium hypochlorite and the oxidation is carried out in the presence of 2,2,6,6-tetramethylpiperidinyloxy free radical (TEMPO).

In another embodiment, the oxidizing reagent used in step xvi) is 1,1-dihydro-1,1,1-triacetoxy-1,2-benzoiodooxol-3(1H)-one.

In one embodiment, the process further comprises dissolving the compound of Formula 4 in an organic solvent to obtain a solution of the compound of Formula 4, and then adding an acid to the solution.

In a further embodiment, the organic solvent is methylene chloride, and the acid is acetic acid.

In another embodiment, the process further comprises concentrating the solution of the compound of Formula 4 to obtain the compound in a solid form.

In one aspect, the invention includes a process of purifying the compound of Formula 4, comprising:

4

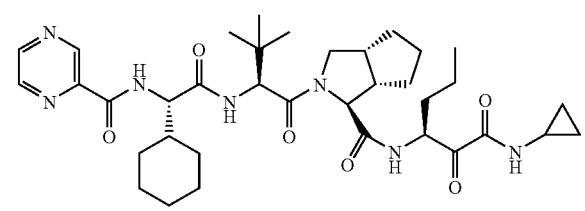

i) dissolving the compound of Formula 4 in an organic solvent to obtain a solution of the compound of Formula 4, ii) adding an acid to the solution of the compound of Formula 4, and iii) concentrating the solution of the compound of Formula 4 to obtain the compound in a solid form.

In one embodiment, the organic solvent is methylene chloride, and the acid is acetic acid.

In one aspect, the invention includes a process of preparing a compound of Formula 8

8

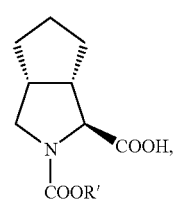

(rac)

comprising carboxylating an azabicyclooctane of Formula 6

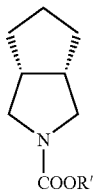

6 to give a racemic mixture of cis and trans octahyclocyclopenta[c]pyrrol-1-carboxylic acids of Formula 7

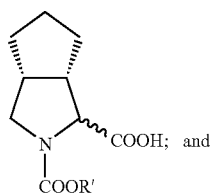

7 equilibrating a trans-/cis-mixture of the compounds of Formula 7 in the presence of a suitable base to produce a predominantly trans-cis racemic acid of Formula 8, wherein the trans-/cis-ratio in the compound of Formula 8 is greater than 80 to 20 and R' is $C_{1-5}$ alkyl.

In one embodiment, the process further comprises equilibrating trans-/cis-mixture of the compounds of Formula 7 in the presence of a suitable base to produce a predominantly trans-cis racemic acid of Formula 8 wherein the trans-/cis-ratio is greater than 90 to 10.

In another embodiment, the process further comprises equilibrating trans-/cis-mixture of Formula 7 in the presence of a suitable base to produce a predominantly trans-cis racemic acid of Formula 8 wherein the trans-/cis-ratio is greater than 98 to 2.

In one embodiment, the base is lithium hexamethyldisilazide, lithium di-isopropylamide, or lithium 2,2,6,6-tetramethylpiperidide.

In a further embodiment, wherein the base is lithium hexamethyldisilazide.

In one aspect, the invention includes a process of preparing a (1S,2S,3R) trans-N-alkoxycarbonyl-octahydrocyclopenta[c]pyrrole-1-carboxylic acid comprising carboxylating an azabicyclooctane of Formula 6

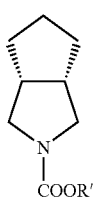

6 to give a racemic mixture of cis and trans octahydrocyclopenta[c]pyrrol-1-carboxylic acids of Formula 7

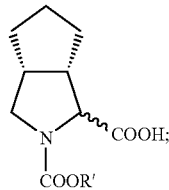

7 equilibrating a trans-/cis-mixture of the compounds of Formula 7 in the presence of a suitable base to produce a predominantly trans-cis racemic acid of Formula 8

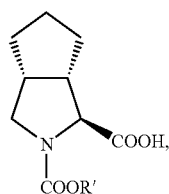

8 wherein the trans-/cis-ratio in the compound of Formula 8 is greater than 80 to 20; and resolving the racemic trans-N-alkoxycarbonyl-octahydrocyclopenta[c]pyrrole-1-carboxylic acid mixture, wherein R' is $C_{1-5}$ alkyl.

In one embodiment, the resolution comprises the steps of:
i) forming a salt with an optically active base; and
ii) crystallizing the salt formed by step i) to provide an optically active salt of Formula 9.

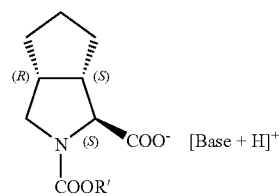

9

In a further embodiment, the optically active base is (R) α-aminoethylbenzene.

In a further embodiment, the optically active base is (S) 1,2,3,4-tetrahydro-1-naphthylamine.

In one aspect, the invention includes a process preparing a compound of Formula 1 comprising carboxylating an azabicyclooctane of Formula 6

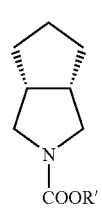

6 to give a racemic mixture of cis and trans octahydrocyclopenta[c]pyrrol-1-carboxylic acids of Formula 7

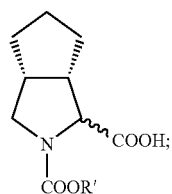

7 equilibrating a trans-/cis-mixture of the compounds of Formula 7 in the presence of a suitable base to produce a predominantly trans-cis racemic acid of Formula 8

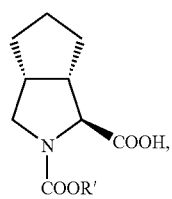

8 wherein the trans-/cis-ratio in the compound of Formula 8 is greater than 80 to 20; forming a salt with an optically active base; crystallizing the salt formed by the previous step to provide an optically active salt of Formula 9

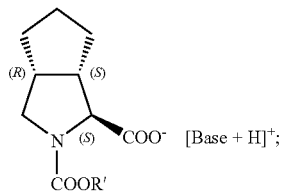

9 esterifying the carboxylic acid of Formula 9 with a compound containing the $R_3$ group; and removing the —COOR' protecting group to produce a compound of Formula 1

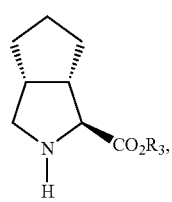

1 wherein R' is $C_{1-5}$ alkyl and $R_3$ is an optionally substituted alkyl or aralkyl.

In one embodiment, $R_3$ is t-butyl.

In one aspect, the invention includes a process for preparing a compound of Formula 4

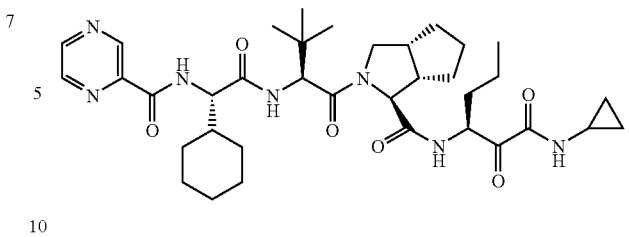

comprising the steps of:

i) providing a compound of Formula 7 which was made by the process described in claim 30;

ii) forming a salt with an optically active amine;

iii) crystallizing the salt;

iv) esterifying the acid provided in step iii);

v) removing the N-alkoxycarbonyl group to produce (1S, 3aR,6aS)-t-butyl-octahydrocyclopenta[c]pyrrole-1-carboxylate, t-butyl ester;

vi) reacting the bicyclic aminoester of step v) with a protected amino acid of Formula 26,

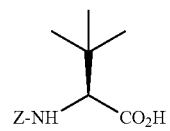

26 wherein Z is an amine protecting group, in the presence of a coupling reagent, to produce an amide-ester of Formula 27.

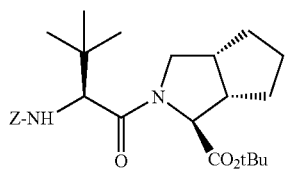

27 vii) removing the protecting group Z from the amide-ester of step vi) to produce the amino compound of Formula 28;

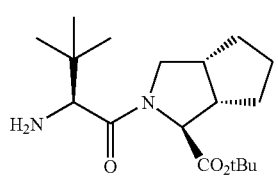

28 viii) reacting the amino compound of Formula 28 with a protected amino acid of Formula 29

29 in the presence of a coupling reagent to produce a tripeptide of Formula 30;

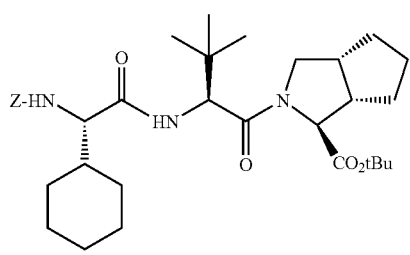

30 ix) removing the protecting group Z in the tripeptide of Formula 30 to produce a free amino-tripeptide of Formula 31;

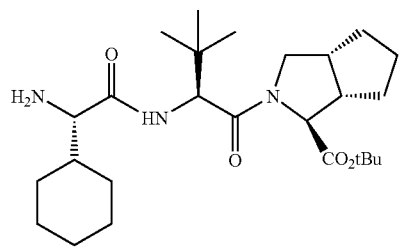

31 x) reacting the amino-tripeptide of Formula 31 with pyrazine-2-carboxylic acid in the presence of a coupling reagent to produce an amide-tripeptide ester of Formula 33;

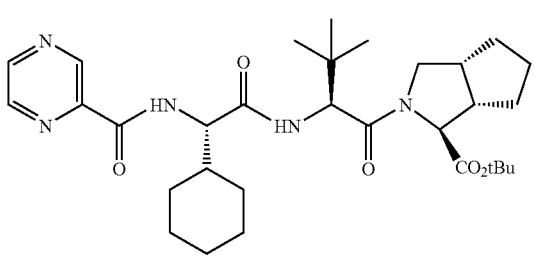

33 xi) hydrolyzing the ester of the amide-tripeptide ester of Formula 33 to produce an amide-tripeptide acid of Formula 34;

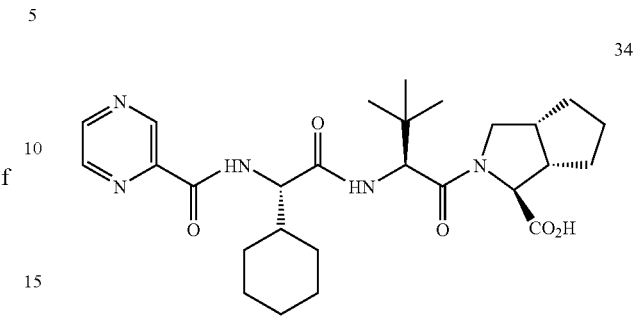

34 xii) reacting the amide-tripeptide acid of Formula 34 with an aminohydroxy-amide of Formula 18

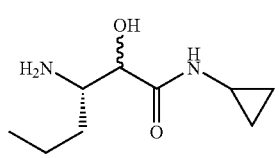

18 in the presence of a coupling reagent to produce a hydroxy-tetrapeptide of Formula 35; and

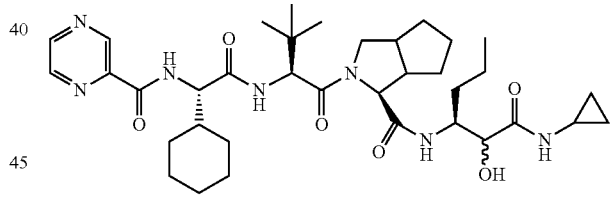

35 xiii) oxidizing the hydroxy group of Formula 35 to produce the compound of Formula 4.

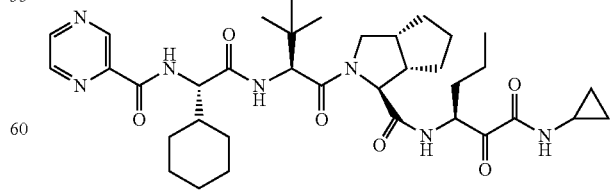

4

In one aspect, the invention includes a process or preparing a compound of Formula 4

4

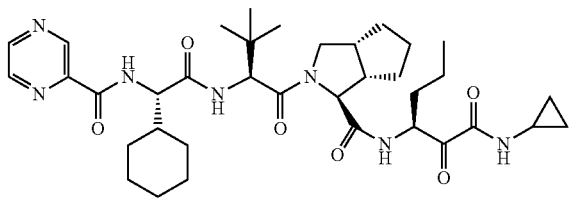

comprising the steps of:
 i) providing an N-alkoxycarbonyl-3-azabicyclo[3.3.0]octane;
 ii) forming a 2-anion of the N-alkoxycarbonyl-3-azabicyclo[3.3.0]octane in the presence of a chelating agent;
 iii) treating the anion of step with carbon dioxide to produce a cis-/trans-mixture of N-alkoxycarbonyl-octahydrocyclopenta[c]pyrrole-1-carboxylic acids;
 iv) treating the mixture of step iii) with a strong base to produce an essentially pure trans-N-alkoxycarbonyl-octahydrocyclopenta[c]pyrrole-1-carboxylic acid;
 v) forming a salt with an optically active amine;
 vi) crystallizing the salt;
 vii) esterifying the acid provided in step vi);
 viii) removing the N-alkoxycarbonyl group to produce (1S,3aR,6aS)-t-butyl-octahydrocyclopenta[c]pyrrole-1-carboxylate, t-butyl ester;
 ix) reacting the bicyclic aminoester of step viii) with a protected amino acid of Formula 26, 26
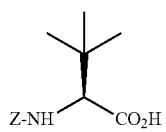

wherein Z is an amine protecting group, in the presence of a coupling reagent, to produce an amide-ester of Formula 27;

27
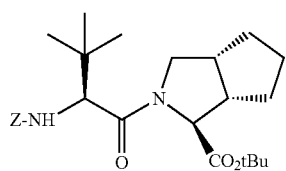

x) removing the protecting group Z from the amide-ester of step ix) to produce the amino compound of Formula 28;

28
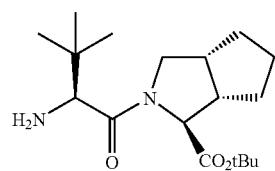

xi) reacting the amino compound of Formula 28 with a protected amino acid of Formula 29

29
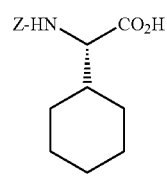

in the presence of a coupling reagent to produce a tripeptide of Formula 30;

30
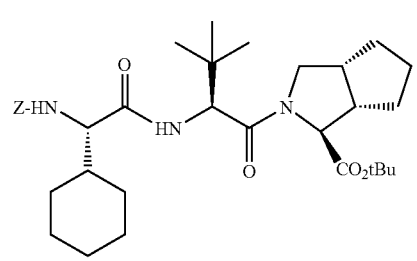

xii) removing the protecting group Z in the tripeptide of Formula 30 to produce a free amino-tripeptide of Formula 31;

31
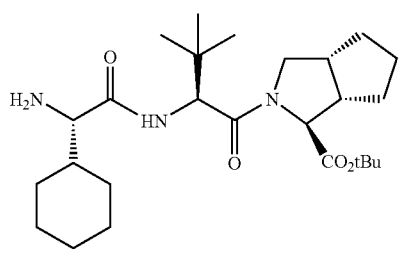

xiii) reacting the amino-tripeptide of Formula 31 with pyrazine-2-carboxylic acid in the presence of a coupling reagent to produce an amide-tripeptide ester of Formula 33;

33
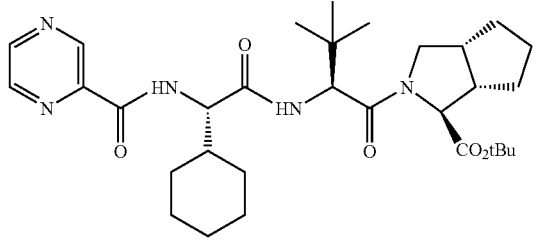

xiv) hydrolyzing the ester of the amide-tripeptide ester of Formula 33 to produce an amide-tripeptide acid of Formula 34;

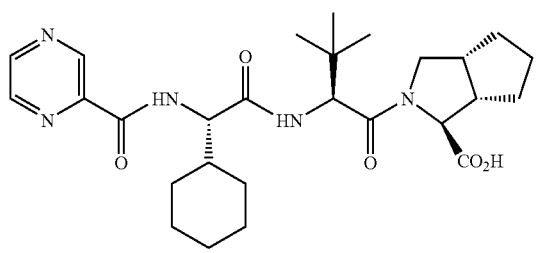

34 xv) reacting the amide-tripeptide acid of Formula 34 with an aminohydroxy-amide of Formula 43

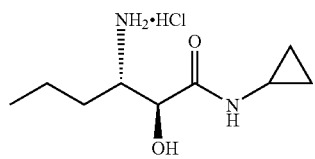

43 in the presence of a coupling reagent to produce a hydroxy-tetrapeptide of Formula 36; and

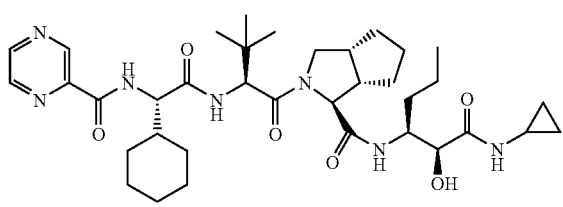

36 xvi) oxidizing the hydroxy group of Formula 36 to produce the compound of Formula 4.

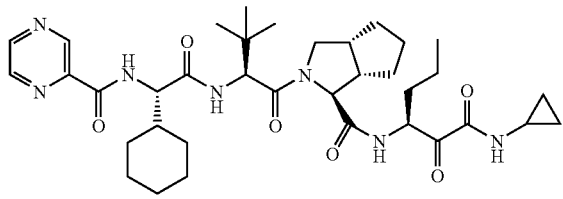

4

In one aspect, the invention includes a process for preparing a compound of Formula 4

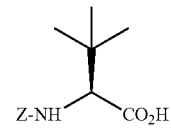

4 comprising the steps of:

i) providing an N-alkoxycarbonyl-3-azabicyclo[3.3.0]octane;

ii) forming a 2-anion of the N-alkoxycarbonyl-3-azabicyclo[3.3.0]octane in the presence of a chelating agent;

iii) treating the anion of step ii) with carbon dioxide to produce a cis-/trans-mixture of N-alkoxycarbonyl-octahydrocyclopenta[c]pyrrole-1-carboxylic acids;

iv) treating the mixture of step iii) with a strong base to produce an essentially pure trans-N-alkoxycarbonyl-octahydrocyclopenta[c]pyrrole-1-carboxylic acid;

v) forming a salt with an optically active amine;

vi) crystallizing the salt;

vii) esterifying the acid provided in step vi);

viii) removing the N-alkoxycarbonyl group to produce (1S,3aR,6aS)-t-butyl-octahydrocyclopenta[c]pyrrole-1-carboxylate, t-butyl ester;

ix) reacting the bicyclic aminoester of step viii) with a protected amino acid of Formula 26,

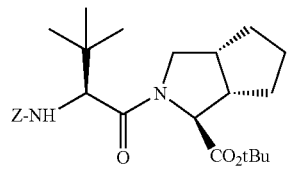

26 wherein Z is an amine protecting group, in the presence of a coupling reagent, to produce an amide-ester of Formula 27;

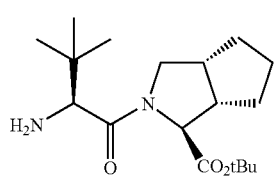

27 x) removing the protecting group Z from the amide-ester of step ix) to produce the amino compound of Formula 28;

28 xi) reacting the amino compound of Formula 28 with a protected amino acid of Formula 29

in the presence of a coupling reagent to produce a tripeptide of Formula 30;

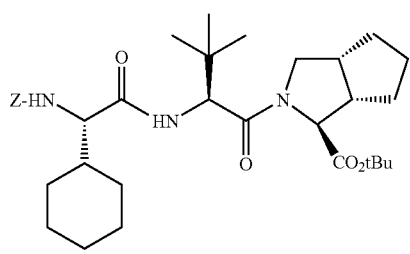

xii) removing the protecting group Z in the tripeptide of Formula 30 to produce a free amino-tripeptide of Formula 31;

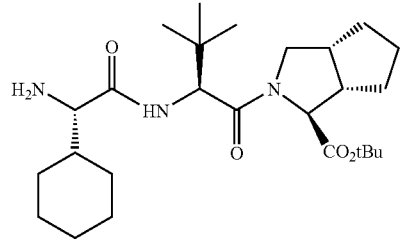

xiii) reacting the amino-tripeptide of Formula 31 with pyrazine-2-carboxylic acid in the presence of a coupling reagent to produce an amide-tripeptide ester of Formula 33;

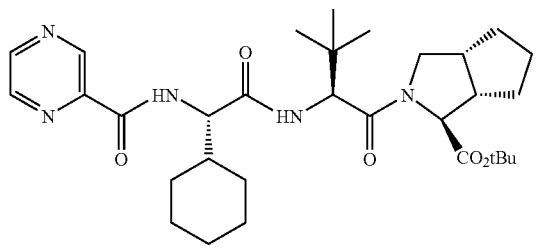

xiv) hydrolyzing the ester of the amide-tripeptide ester of Formula 33 to produce an amide-tripeptide acid of Formula 34;

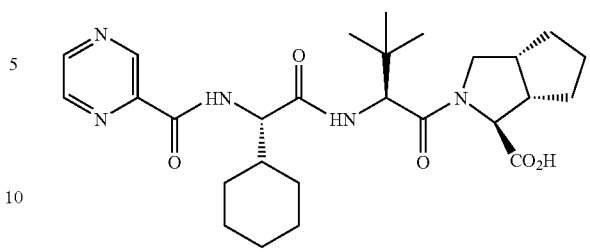

xv) reacting the amide-tripeptide acid of Formula 34 with an aminohydroxy-amide of Formula 44

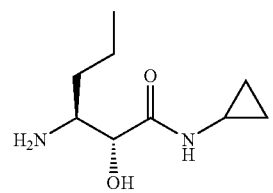

in the presence of a coupling reagent to produce a hydroxy-tetrapeptide of Formula 45; and

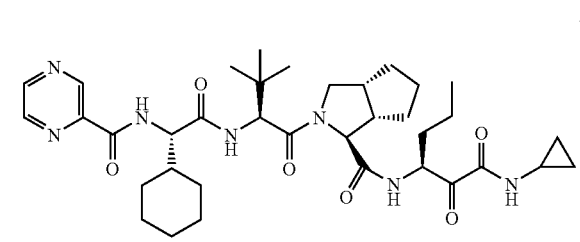 [SMILES: CCC[C@H](NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1]

xvi) oxidizing the hydroxy group of Formula 45 to produce the compound of Formula 4.

In one embodiment, the oxidizing reagent used in step xvi) is sodium hypochlorite and the oxidation is carried out in the presence of 2,2,6,6-tetramethylpiperidinyloxy free radical (TEMPO).

In another embodiment, the oxidizing reagent used in step xvi) is 1,1-dihydro-1,1,1-triacetoxy-1,2-benzoiodooxol-3(1H)-one.

In one embodiment, the process further comprises dissolving the compound of Formula 4 in an organic solvent to obtain a solution of the compound of Formula 4, and then adding an acid to the solution.

In a further embodiment, the organic solvent is methylene chloride, and the acid is acetic acid.

In one embodiment, the process further comprises concentrating the solution of the compound of Formula 4 to obtain the compound in a solid form.

In one aspect, the invention includes a compound of Formula 4 made by the any of the processes described herein.

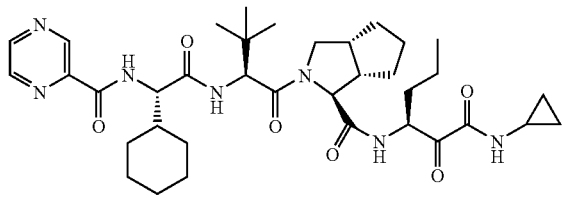

4

In one aspect, the invention includes a compound of Formula 7 made by the process of preparing a racemic mixture of cis- and trans-octahydrocyclopenta[c]pyrrole-1-carboxylic acids of Formula 7 described herein.

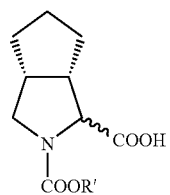

7

In one aspect, the invention includes a compound of Formula 8 made by the process of preparing a compound of Formula 8 described herein.

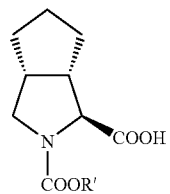

8

In one aspect, the invention includes a compound of Formula 9 made by the process of resolving the racemic trans-N-alkoxycarbonyl-octahydrocyclopenta[c]pyrrole-1-carboxylic acid mixture as described herein.

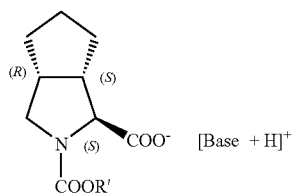

9

In one aspect, the invention includes a compound of Formula 1 made by the process of preparing a compound of Formula 1 by carboxylating an azabicyclooctane of Formula 6 as described herein.

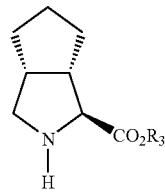

1

DESCRIPTION OF THE INVENTION

I. Definitions

For purposes of this invention, the chemical elements are identified in accordance with the Periodic Table of the Elements, CAS version, Handbook of Chemistry and Physics, 75$^{th}$ Ed. Additionally, general principles of organic chemistry are described by Thomas Sorrell in Organic Chemistry, University Science Books, Sausalito (1999), and by M. B. Smith and J. March in Advanced Organic Chemistry, 5$^{th}$ Ed., John Wiley & Sons, New York (2001), the entire contents of which are hereby incorporated by reference.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, and alkynyl, each of which is optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents selected from the group J ("Group J") which consists of halo, cycloaliphatic (e.g., cycloalkyl or cycloalkenyl), heterocycloaliphatic (e.g., heterocycloalkyl or heterocycloalkenyl), aryl, heteroaryl, alkoxy, aroyl, heteroaroyl, acyl (e.g., (aliphatic)carbonyl, (cycloaliphatic)carbonyl, or (heterocycloaliphatic)carbonyl), nitro, cyano, amido (e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl), amino (e.g., aliphaticamino, cycloaliphaticamino, or heterocycloaliphaticamino), sulfonyl (e.g., aliphatic-SO$_2$—), sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, and hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents selected from Group J such as halo, cycloaliphatic (e.g., cycloalkyl or cycloalkenyl), heterocycloaliphatic (e.g., heterocycloalkyl or heterocycloalkenyl), aryl, heteroaryl, alkoxy, aroyl, heteroaroyl, acyl (e.g., (aliphatic)carbonyl, (cycloaliphatic)carbonyl, or (heterocycloaliphatic)carbonyl), nitro, cyano, amido (e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl), amino (e.g., aliphaticamino, cycloaliphaticamino, heterocycloaliphaticamino, or aliphaticsulfonylamino), sulfonyl (e.g., alkyl-$SO_2$—, cycloaliphatic-$SO_2$—, or aryl-$SO_2$—), sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents selected from Group J such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl (e.g., aliphaticsulfanyl or cycloaliphaticsulfanyl), sulfinyl (e.g., aliphaticsulfinyl or cycloaliphaticsulfinyl), sulfonyl (e.g., aliphatic-$SO_2$—, aliphaticamino-$SO_2$—, or cycloaliphatic-$SO_2$—), amido (e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl), urea, thiourea, sulfamoyl, sulfamide, alkoxycarbonyl, alkylcarbonyloxy, cycloaliphatic, heterocycloaliphatic, aryl, heteroaryl, acyl (e.g., (cycloaliphatic) carbonyl or (heterocycloaliphatic)carbonyl), amino (e.g., aliphaticamino), sulfoxy, oxo, carboxy, carbamoyl, (cycloaliphatic)oxy, (heterocycloaliphatic)oxy, or (heteroaryl) alkoxy.

As used herein, an "amido" encompasses both "aminocarbonyl" and "carbonylamino." These terms, when used alone or in connection with another group, refer to an amido group such as —N($R^X$)—C(O)—$R^Y$ or —C(O)—N($R^X$)$_2$, when used terminally; and they refer to an amide group such as —C(O)—N($R^X$)— or —N($R^X$)—C(O)— when used internally, wherein $R^X$ and $R^Y$ are defined below. Examples of amido groups include alkylamido (such as alkylcarbonylamino or alkylaminocarbonyl), (heterocycloaliphatic) amido, (heteroaralky)amido, (heteroaryl)amido, (heterocycloalkyl)alkylamido, arylamido, aralkylamido, (cycloalkyl) alkylamido, or cycloalkylamido.

As used herein, an "amino" group refers to —$NR^XR^Y$, wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic) aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2- to 3-membered carbocyclic rings. For example, a benzofused group includes phenyl fused with two or more $C_{4-8}$ carbocyclic moieties. An aryl is optionally substituted with one or more substituents such as aliphatic (e.g., alkyl, alkenyl, or alkynyl); cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl (e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic) aliphatic)carbonyl; or (heteroaraliphatic)carbonyl); sulfonyl (e.g., aliphatic-$SO_2$— or amino-$SO_2$—); sulfinyl (e.g., aliphatic-S(O)— or cycloaliphatic-S(O)—); sulfanyl (e.g., aliphatic-S—); cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl mono-, di-(such as p,m-dihaloaryl), or (trihalo)aryl); (carboxy)aryl (e.g., (alkoxycarbonyl)aryl, ((aralkyl)carbonyloxy)aryl, or (alkoxycarbonyl)aryl); (amido)aryl (e.g., (aminocarbonyl)aryl, (((alkylamino)alkyl)aminocarbonyl)aryl, (alkylcarbonyl)aminoaryl, (arylaminocarbonyl)aryl, or (((heteroaryl)amino)carbonyl)aryl); aminoaryl (e.g., ((alkylsulfonyl)amino)aryl or ((dialkyl)amino)aryl); (cyanoalkyl) aryl; (alkoxy)aryl; (sulfamoyl)aryl (e.g., (aminosulfonyl) aryl); (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl) aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl)) aryl.

As used herein, an "araliphatic" group, such as "aralkyl," refers to an aliphatic group (e.g., a $C_{1-4}$ alkyl group) that is substituted with an aryl group. "Aliphatic," "alkyl," and "aryl" are defined herein. An example of araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic (e.g., substituted or unsubstituted alkyl, alkenyl, or alkynyl, including carboxyalkyl, hydroxyalkyl, or haloalkyl such as trifluoromethyl), cycloaliphatic (e.g., substituted or unsubstituted cycloalkyl or cycloalkenyl), (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido (e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino), cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8- to 12- (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2] octyl, bicyclo[3.3.1]nonyl, bicyclo[3.3.2.]decyl, bicyclo [2.2.2]octyl, adamantyl, azacycloalkyl, or ((aminocarbonyl) cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents selected from Group J such as aliphatic (e.g., alkyl, alkenyl, or alkynyl), cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic) oxy, aryloxy, heteroaryloxy, (araliphatic)oxy, (heteroaraliphatic)oxy, aroyl, heteroaroyl, amino, amido (e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or ((heteroaraliphatic)carbonylamino), nitro, carboxy (e.g., HOOC—, alkoxycarbonyl, or alkylcarbonyloxy), acyl ((e.g., (cycloaliphatic)carbonyl, (cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl), cyano, halo, hydroxy, mercapto, sulfonyl (e.g., alkyl-SO$_2$— and aryl-SO$_2$—), sulfinyl ((e.g., alkyl-S(O)—), sulfanyl (e.g., alkyl-S—), sulfoxy, urea, thiourea, sulfamoyl, sulfamide, oxo, or carbamoyl.

As used herein, "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b] thiopheneyl, 2-oxa-bicyclo[2.2.2]octyl, 1-aza-bicyclo[2.2.2] octyl, 3-aza-bicyclo[3.2.1]octyl, and 2,6-dioxa-tricyclo [3.3.1.0$^{3,7}$]nonyl. A monocyclic heterocycloalkyl group can be fused with a phenyl moiety such as tetrahydroisoquinoline. A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclohetreoaliphatics are numbered according to standard chemical nomenclature.

A heterocycloalkyl or heterocycloalkenyl group can be optionally substituted with one or more substituents selected from Group J such as aliphatic (e.g., alkyl, alkenyl, or alkynyl), cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido (e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino), nitro, carboxy (e.g., HOOC—, alkoxycarbonyl, or alkylcarbonyloxy), acyl ((e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl), nitro, cyano, halo, hydroxy, mercapto, sulfonyl (e.g., alkylsulfonyl or arylsulfonyl), sulfinyl (e.g., alkylsulfinyl), sulfanyl (e.g., alkylsulfanyl), sulfoxy, urea, thiourea, sulfamoyl, sulfamide, oxo, or carbamoyl)).

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b] thiophenyl, indazolyl, benzimidazolyl, benzthiazolyl, puryl, cinnolyl, quinolyl, quinazolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic (e.g., alkyl, alkenyl, or alkynyl); cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl (e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl); sulfonyl (e.g., aliphaticsulfonyl or aminosulfonyl); sulfinyl (e.g., aliphaticsulfinyl); sulfanyl (e.g., aliphaticsulfanyl); nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl (e.g., mono- and di-(halo)heteroaryl); (carboxy)heteroaryl (e.g., (alkoxycarbonyl)heteroaryl); cyanoheteroaryl; aminoheteroaryl (e.g., ((alkylsulfonyl)amino)heteroaryl and ((dialkyl)amino)heteroaryl); (amido)heteroaryl (e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, or ((alkylcarbonyl)amino) heteroaryl); (cyanoalkyl)heteroaryl; (alkoxy)heteroaryl; (sulfamoyl)heteroaryl (e.g., (aminosulfonyl)heteroaryl); (sulfonyl)heteroaryl ((e.g., (alkylsulfonyl)heteroaryl); (hydroxyalkyl)heteroaryl; (alkoxyalkyl)heteroaryl; (hydroxy) heteroaryl; ((carboxy)alkyl)heteroaryl; (((dialkyl)amino) alkyl)heteroaryl; (heterocycloaliphatic)heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl (e.g., (alkylcarbonyl)heteroaryl); (alkyl)heteroaryl; and (haloalkyl) heteroaryl (e.g., trihaloalkylheteroaryl).

A "heteroaraliphatic" (such as a heteroalkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") wherein $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group wherein "alkyl" has been defined previously.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, OC(O)R$^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —N'R$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$—S(O)$_2$—R$_Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyl include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, ((cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—$R^X$ or —SO—O—$R^X$, when used terminally and —O—S(O)— or —S(O)—O— when used internally, wherein $R^X$ has been defined above.

As used herein, a "halogen" or "halo" group refers to fluorine, chlorine, bromine, or iodine.

As used herein, an "alkoxycarbonyl" group, which is encompassed by "carboxy," used alone or in combination with another group, refers to a group such as alkyl-O—C(O)—.

As used herein, an "alkoxyalkyl" group refers to an alkyl group such as alkyl-O-alkyl-, wherein alkyl has been defined above.

As used herein, a "carbonyl" group refer to —C(O)—.

As used herein, an "oxo" group refers to =O.

As used herein, an "aminoalkyl" group refers to the structure $(R^X)_2$N-alkyl-.

As used herein, a "cyanoalkyl" group refers to the structure (NC)-alkyl-.

As used herein, a "urea" group refers to the structure —$NR^X$—CO—$NR^Y R^Z$ and a "thiourea" group refers to the structure —$NR^X$—CS—$NR^Y R_Z$ when used terminally and —$NR^X$—CO—$NR^Y$— or —$NR^X$—CS—$NR^Y$— when used internally, wherein $R^X$, $R^Y$, and $R^Z$ have been defined above.

As used herein, a "guanidine" group refers to the structure —N=C(N($R^X R^Y$))N($R^X R^Y$) or —$NR^X$—C(=$NR^X$)$NR^X R^Y$, wherein $R^X$ and $R^Y$ have been defined above.

As used herein, an "amidino" group refers to the structure —C=($NR^X$)N($R^X R^Y$), wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)—O— or alkyl-O—C(O)—) and alkylcarboxyaryl (e.g., alkyl-C(O)—O-aryl- or alkyl-O—C(O)-aryl-) are examples of carboxy groups used internally.

As used herein, a "cyclic" group includes a mono-, bi-, and tri-cyclic ring system, such as cycloaliphatic, heterocycloaliphatic, aryl, or heteroaryl, each of which has been defined above.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —(CH$_2$)$_v$—, where v is 1-6. A branched aliphatic chain is a straight aliphatic chain that is substituted with one or more aliphatic groups. A branched aliphatic chain has the structure —(CHQ)$_v$-, where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, and $R_3$, as well as other variables, encompass specific groups, such as alkyl and aryl. Unless otherwise noted, each of the specific groups for the variables $R_1$, $R_2$, and $R_3$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. Combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C-$ or $^{14}C$-enriched carbon are within the scope of this invention. Such compounds are useful, for example, as analytical tools or probes in biological assays.

As used herein, EDC is 1-(3-dimethylaminopropyl)-3-ethylcarbodiimide, HOBt is 1-hydroxybenzotriazole, HOSuc is N-hydroxysuccinimide, THF is tetrahydrofuran, TFA is trifluoroacetic acid, DCM is dichloromethane, DMAP is 4-dimethylaminopyridine, DIPEA is diisopropylethylamine, DMF is dimethylformamide, TFA is trifluoroacetic acid, and CBZ is benzyloxycarbonyl, and TEMPO is 2,2,6,6-tetramethylpiperidinyloxy.

As used herein, $^1H$ NMR stands for proton nuclear magnetic resonance, and TLC stands for thin layer chromatography.

II. Processes and Intermediates

In one embodiment, the invention provides a process and intermediates for preparing a compound of Formula 1 as outlined in Scheme I.

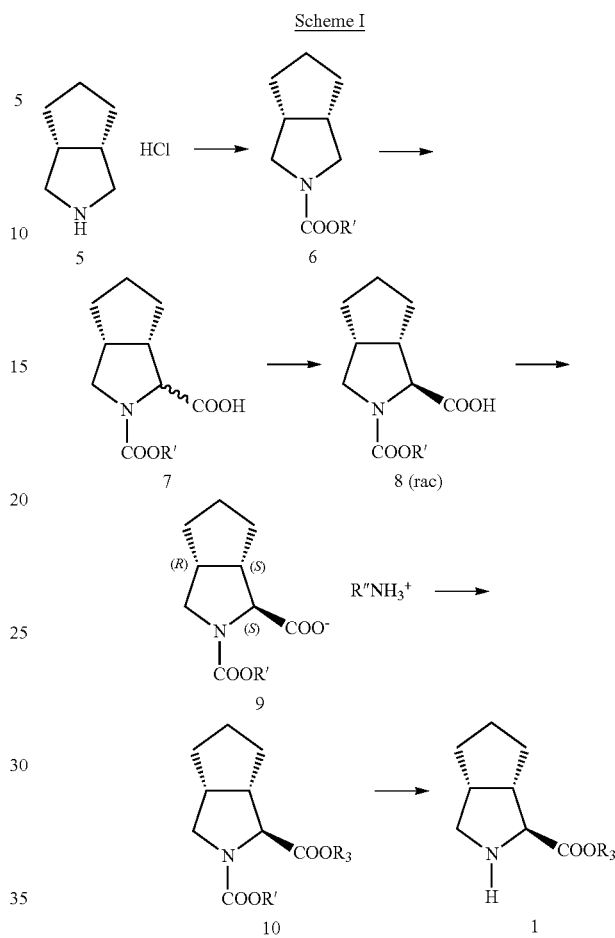

Scheme I

Referring to Scheme I, 3-azabicyclo[3.3.0]octane of Formula 5 (R. Griot, *Helv. Chim, Acta.*, 42, 67, (1959) is converted to a suitable alkyl carbamate of Formula 6 wherein R' is, e.g., t-butyl or isobutyl, using known methods. See, e.g., T. W. Greene and P. G. M. Wuts, Protective Groups in Organic Synthesis, 3$^{rd}$ edition, John Wiley and Sons, Inc. (1999).

Carboxylation of the N-alkoxycarbonyl-3-azabicyclo [3.3.0]octane of Formula 6 is achieved by first forming a 2-anion of Formula 6 in the presence of a chelating agent (for formation of similar anions. See, e.g., Daniel. J. Pippel, et. al., *J. Org. Chem.*, 1998, 63, 2; Donald J. Gallagher et al., *J. Org. Chem.*, 1995, 60(22), 7092-7093; Shawn T. Kerrick et al., *J. Am. Chem. Soc.*, 1991, 113(25), 9708-9710; Donald J. Gallagher et al., *J. Org. Chem.*, 1995, 60(25), 8148-8154; and Peter Beak et al., *J. Am, Chem. Soc.*, 1994, 116(8), 3231-3239. The 2-anion of the alkyl carbamate of Formula 6 (not shown in Scheme 1) is prepared by treatment of compound of Formula 6 with a strong lithium base (e.g., t-butyl lithium or sec-butyl lithium) in the presence of a complexing agent (e.g., tetramethylethylenediamine, tetraethylethylenediamine, tetramethyl-1,2-cyclohexyldiamine, or 3,7-dipropyl-3,7-diazabicyclo[3.3.1]nonane) in a suitable aprotic solvent. Suitable aprotic solvents include, e.g., t-butylmethyl ether, tetrahydrofuran, and dimethoxyethane. Subsequently, the 2-anion of Formula 6 can be treated with carbon dioxide to give a racemic mixture of trans-/cis-2-carboxylic acids of Formula 7 wherein the trans-leis-ratio is 30 to 70, 40 to 60, 50 to 50, 60 to 40, 80 to 20, 90 to 10, 95 to 5, or greater than 98 to 2.

In some embodiments, the complexing agent may be optically active, such as, for example, an optical isomer of sparteine. An optically active complexing agent can induce asymmetric carboxylation to give a product having an enantiomeric excess (e.e.) of from about 10% to about 95% (see, e.g., Beak et. al., *J. Org. Chem.*, 1995, 60, 8148-8154). The trans-/cis-mixture is equilibrated to give a predominantly trans acid of Formula 8 wherein the trans-/cis-ratio is 80 to 20, 90 to 10, 95 to 5, or greater than 98 to 2, in the presence of a suitable base. Suitable bases include, e.g., lithium hexamethyldisilazide, lithium di-isopropylamide, or lithium 2,2,6,6-tetramethylpiperidine.

In another embodiment, the use of 3,7-dipropyl-3,7-diazabicyclo[3.3.1]nonane as the complexing diamine provides the carboxylic acid of Formula 8 with a trans-/cis-ratio of isomers of 90 to 10, 95 to 5, or greater than 98 to 2 directly and obviates the equilibration step.

The racemic mixture of the compound of Formula 8 may be resolved to provide a single enantiomer of Formula 9. Known methods of resolving racemic amino acids may be used and include, but are not limited to, crystallization of an optically active amine salt, preparing a 2-carboxylate ester with an optically active alcohol followed by crystallization or chromatographic separation, and preparing an optically active N-alkoxycarbonyl derivative followed by crystallization or chromatography. In one embodiment, the (R) α-aminoethylbenzene or (S) 1-amino-1,2,3,4-tetrahydronaphthalene salt of compound of Formula 8 is crystallized to produce the amine salt of Formula 9.

The free acid of the salt of Formula 9, obtained by extraction of, for example, an aqueous sodium bisulfate solution is esterified with, for example, di-t-butyl-dicarbonate ($Boc_2O$) to give the ester of Formula 10. Removal of the —COOR' protecting group under known conditions, for example, methane sulfonic acid in an organic solvent such as, for example, t-butylmethyl ether or tetrahydrofuran, provides the compounds of Formula 1.

In another embodiment, bicyclic pyrrolidinyl compounds of Formula 3 (as exemplified by compounds 17 shown below) may be prepared as outlined in Scheme II.

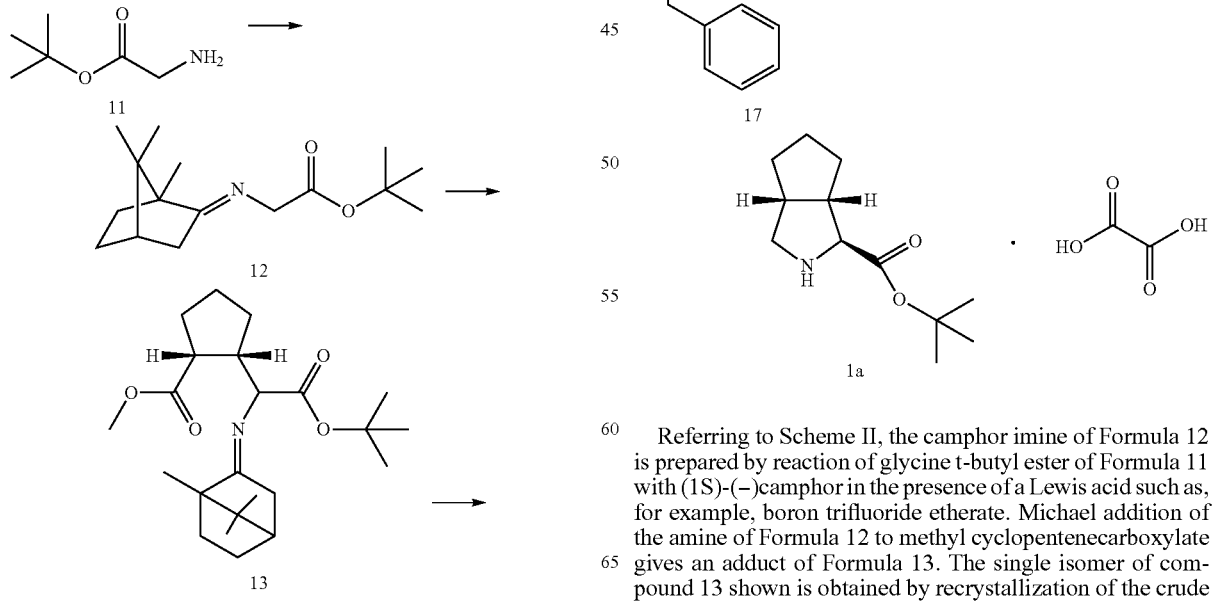

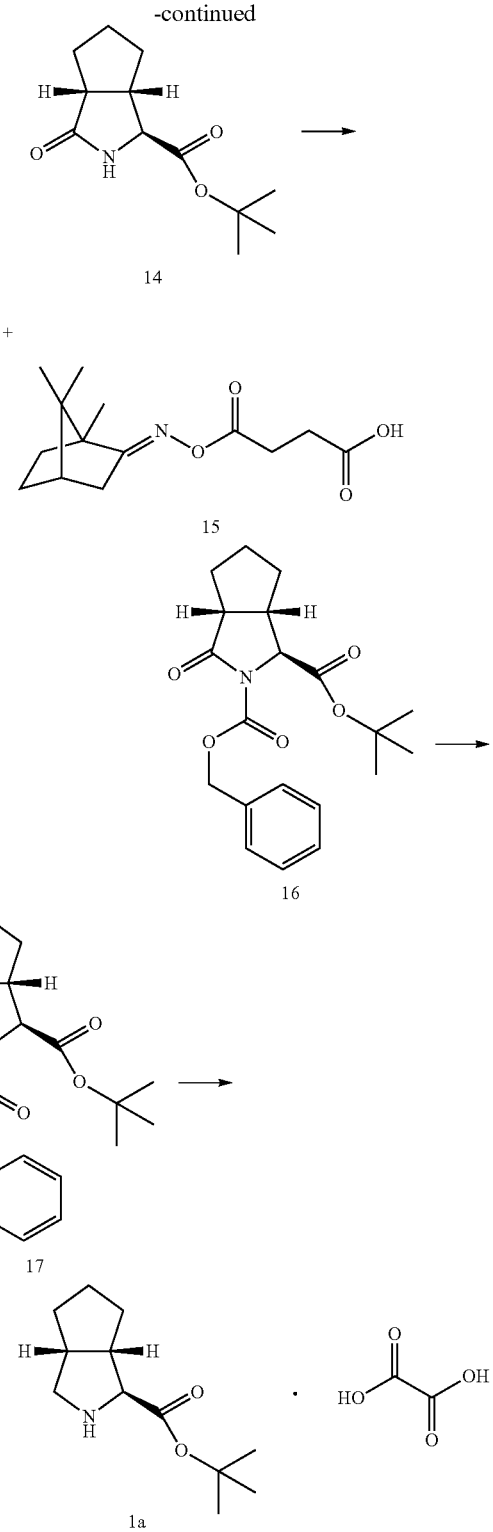

Referring to Scheme II, the camphor imine of Formula 12 is prepared by reaction of glycine t-butyl ester of Formula 11 with (1S)-(−)camphor in the presence of a Lewis acid such as, for example, boron trifluoride etherate. Michael addition of the amine of Formula 12 to methyl cyclopentenecarboxylate gives an adduct of Formula 13. The single isomer of compound 13 shown is obtained by recrystallization of the crude product from a mixture of isopropanol and water. Removal of the camphor imine with hydroxylamine in the presence of sodium acetate and subsequent cyclization yields the lactam ester of Formula 14. Optionally, the reaction mixture may be treated with succinic anhydride to facilitate recovery of the desired product of Formula 14 and the camphor derivative of Formula 15. The lactam of Formula 14 is converted to its benzyloxycarbonyl derivative of Formula 16 by treatment with a base such as, e.g., sodium hydride, followed by benzyl chloroformate. Reduction of the lactam of Formula 16 with a hydride reducing agent such as, e.g., borane-dimethylsulfide-piperidine provides the carbamate ester of Formula 17. Removal of the benzyloxycarbonyl protecting group may be achieved under reducing conditions such as, e.g., hydrogen in the presence of a palladium catalyst such as, e.g., palladium hydroxide, to give the desired bicyclic pyrrolidine ester of Formula 17. Isolation of the ester of Formula 17 is optionally achieved through formation of a salt such as, e.g., an oxalate salt of Formula 1a.

The invention further provides processes for the preparation of compounds of Formula 2. One specific example of a compound of Formula 2, wherein $R'_4$ is H, $R'_5$ is n-propyl, and $R_4$ is cyclopropyl, is shown below in Formula 18.

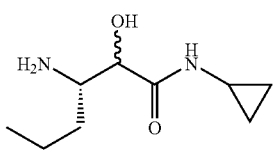

In one aspect, compound 18 can be prepared as outlined in Scheme III.

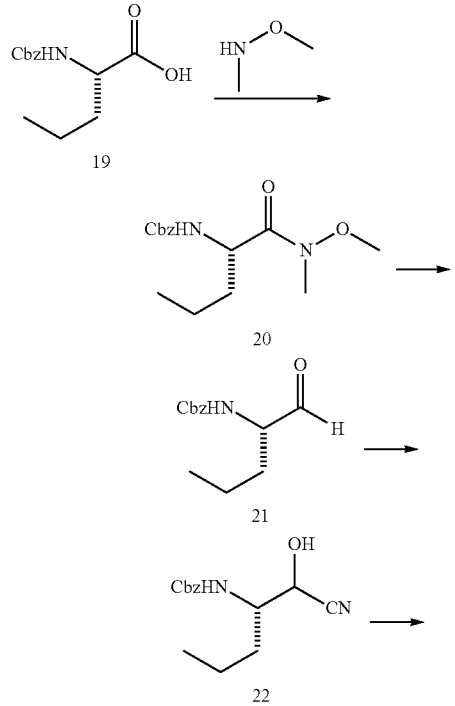

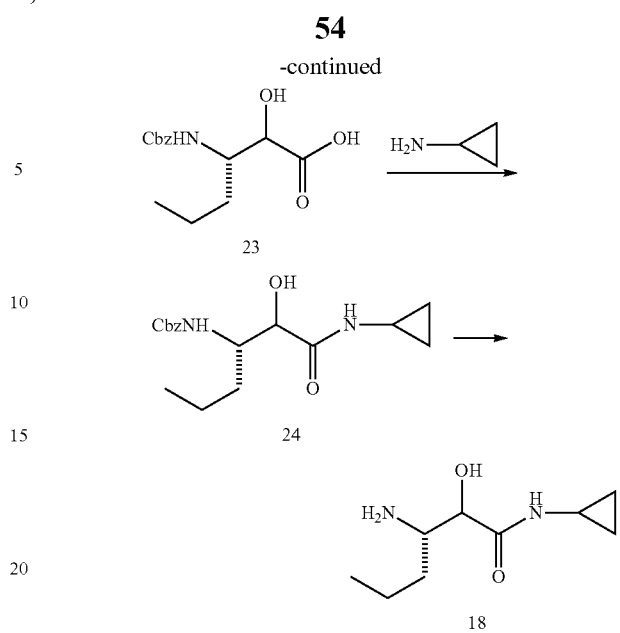

In Scheme III, the methoxymethylamide of Cbz-norvaline of Formula 20 is prepared by reaction of Cbz-norvaline of Formula 19 with methoxymethylamine in the presence of a coupling reagent such as, e.g., EDC. Reduction of compound of Formula 20 with a hydride reagent such as, e.g., lithium aluminum hydride or diisobutylaluminum hydride at a temperature between −20° C. and 10° C. provides a norvalinal compound of Formula 21. Preparation of the corresponding cyanohydrin of Formula 22 is achieved by reacting compound of Formula 21 with an alkali metal cyanide such as, e.g., potassium cyanide, in the presence of an alkali metal thiosulfite such as, e.g., sodium thiosulfite. Hydrolysis of compound of Formula 22 in the presence of HCl in a suitable solvent such as, e.g., dioxane, and at an elevated temperatures of from about 50° C. to 110° C. leads to the corresponding 3-amino-2-hydroxyhexanoic acid (not shown) which is converted to the Cbz derivative of Formula 23 by reaction with Cbz-hydroxysuccinimide. The cyclopropyl amide of Formula 24 is prepared from compound 23 by reaction with cyclopropylamine in the presence of a coupling reagent such as, e.g., EDC. Removal of the Cbz group to give a compound of Formula 18 is achieved under known reducing conditions such as, e.g., hydrogen in the presence of a palladium catalyst.

In another embodiment, as illustrated in Scheme IV below, a cyclopropylamide of Formula 18 is prepared using the Passerini reaction (see, e.g., A. Doemling et al., *Angew. Chem.*, 2000, 112, 3300-3344).

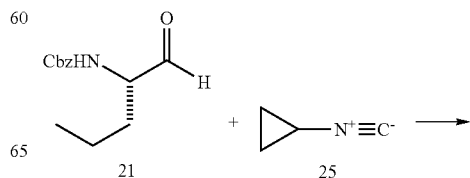

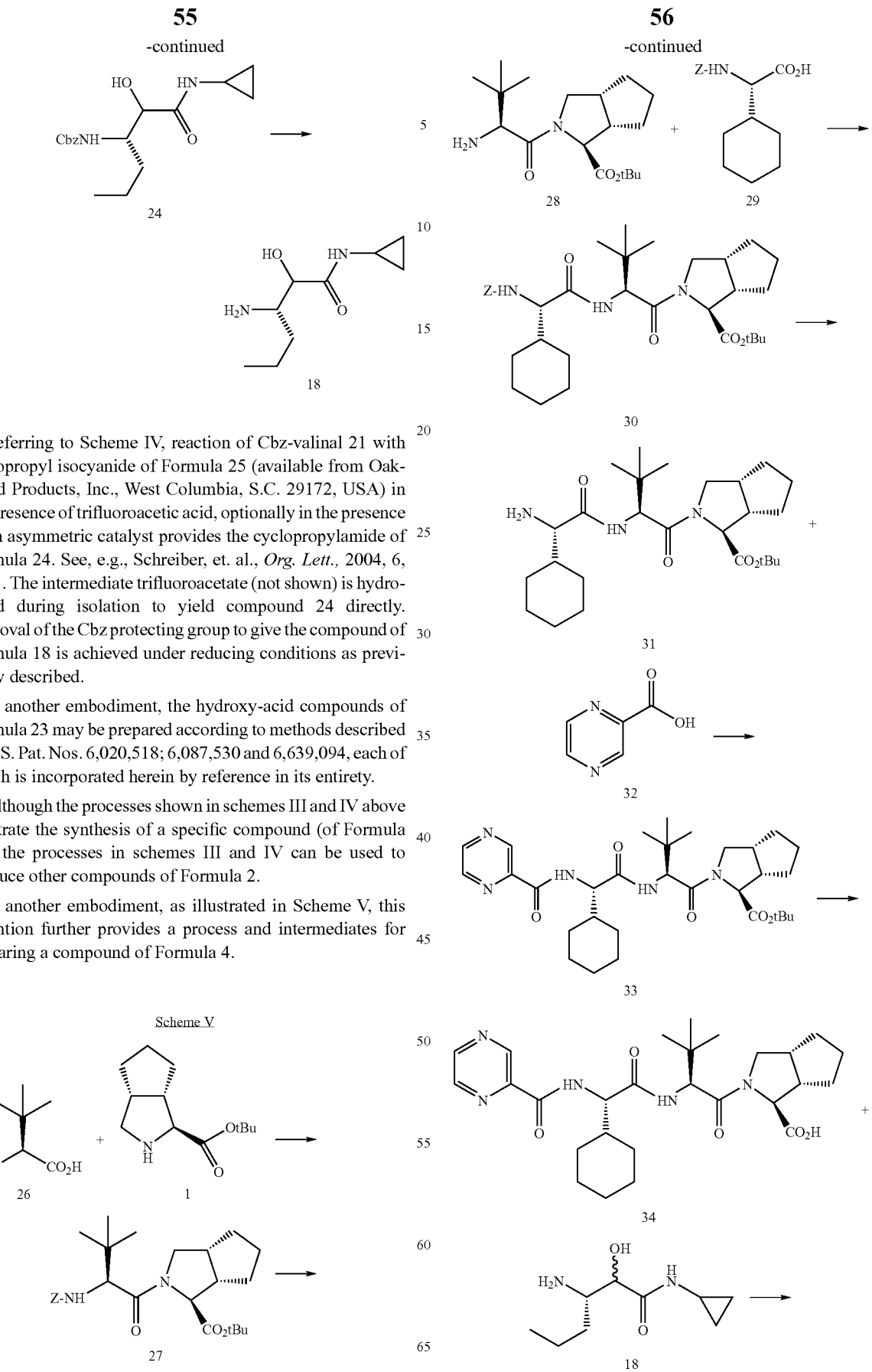

Referring to Scheme IV, reaction of Cbz-valinal 21 with cyclopropyl isocyanide of Formula 25 (available from Oakwood Products, Inc., West Columbia, S.C. 29172, USA) in the presence of trifluoroacetic acid, optionally in the presence of an asymmetric catalyst provides the cyclopropylamide of Formula 24. See, e.g., Schreiber, et. al., *Org. Lett.,* 2004, 6, 4231. The intermediate trifluoroacetate (not shown) is hydrolyzed during isolation to yield compound 24 directly. Removal of the Cbz protecting group to give the compound of Formula 18 is achieved under reducing conditions as previously described.

In another embodiment, the hydroxy-acid compounds of Formula 23 may be prepared according to methods described in U.S. Pat. Nos. 6,020,518; 6,087,530 and 6,639,094, each of which is incorporated herein by reference in its entirety.

Although the processes shown in schemes III and IV above illustrate the synthesis of a specific compound (of Formula 18), the processes in schemes III and IV can be used to produce other compounds of Formula 2.

In another embodiment, as illustrated in Scheme V, this invention further provides a process and intermediates for preparing a compound of Formula 4.

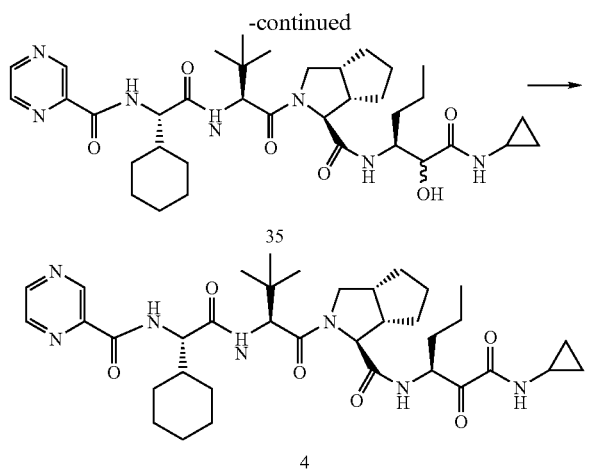

Referring to Scheme V, a bicyclic aminoester of Formula 1, wherein $R_3$ is t-butyl, is reacted with a protected amino acid of Formula 26 (wherein Z is an amine protecting group and can be removed under acidic, basic or hydrogenating conditions different from those used for removing an $R_3$ protecting group) in the presence of a coupling reagent, to give an amide-ester of Formula 27. The protecting group Z is removed from the amide-ester of Formula 27 to give the amine-ester compound of Formula 28.

Reaction of the amino-containing compound of Formula 28 with the protected amino acid 29 in the presence of a coupling reagent gives a tripeptide of Formula 30.

Removing the protecting group Z in the tripeptide of Formula 30 provides a free amino-tripeptide of Formula 31.

Reaction of the amino-tripeptide of Formula 31 with pyrazine-2-carboxylic acid, of Formula 32, in the presence of a coupling reagent yields the amide-tripeptide ester of Formula 33.

Hydrolysis of the ester of the amide-tripeptide ester of Formula 33 provides the amido-tripeptide acid of Formula 34;

Reacting the amido-tripeptide acid of Formula 34 with the amino-hydroxy amide of Formula 18 in the presence of a coupling reagent gives the hydroxy-peptide of Formula 35.

In the final step, oxidation of the hydroxy group of the compound of Formula 35 provides the compound of Formula 4.

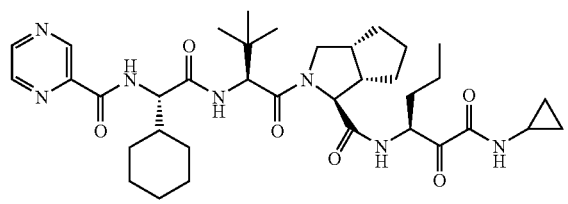

Oxidation of compound 35 may be achieved with a variety of known oxidizing reagents, such as, for example: chromic acid in acetone; Dess-Martin periodinane (1,1-dihydro-1,1,1-triacetoxy-1,2-benzoiodooxol-3(1H)-one); sodium hypochlorite in the presence of TEMPO and, optionally, an alkali metal halide such as sodium bromide.

In some embodiments, the configuration of the hydroxy group of 35 is a mixture of R and S isomers in the ratio of from about 90 to 10 to about 10 to 90, typically in a ratio of about 60 to 40 to about 40 to 60.

In another embodiment, the hydroxy group of compound 35 has the R configuration with an enantiomeric excess of about 90% ee.

In a further embodiment, the hydroxy group of compound 35 has the S configuration with an enantiomeric excess of about 90% ee.

Any of the intermediates obtained as described herein, may be used with or without isolation from the reaction mixture. The desired protease inhibitor may be derived by attaching the appropriate RW—, $P_2$—, $P_3$-$L_2$-$P_2$, or $P_4$-$L_3$-$P_3$-$L_2$-$P_2$— moiety. A coupling of an amine with such a moiety may be carried out using the corresponding carboxylic acid, or reactive equivalent thereof, under standard amide bond-forming or coupling conditions. A typical coupling reaction includes a suitable solvent, the amine in a concentration ranging from about 0.01 to 10M, preferably about 0.1 to about 4.0M, the requisite carboxylic acid, a base and a peptide coupling reagent.

If an amine is used without isolation, the coupling may be carried out in situ in the solvent of the reaction mixture used in the preparation of the amine, or in a different solvent. To this reaction mixture, the requisite carboxylic acid may be added and the reaction maintained at a temperature in the range of about 0° C. to 100° C., preferably between about 20° C. to about 40° C. The base and peptide coupling reagent are then added to the mixture, which is maintained at a temperature in the range of about 0° C. to about 60° C., preferably between about 20° C. to about 40° C. The base is typically a tertiary amine base, such as triethylamine, di-iso-propylethylamine, N-methylmorpholine, DBU, DBN, N-methylimidazole, preferably triethylamine or diisopropylethylamine. The amount of base used is generally up to about 20 equivalents per equivalent of the amine, preferably at least about 3 equivalents of base. Examples of peptide coupling reagents include DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl)-3-ethyl-carbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP—Cl (bis(2-oxo-3-oxazolidinyl)phosphinic chloride), PyBOP ((1-H-1,2,3-benzotriazol-1-yloxy)-tris(pyrrolidino) phosphonium tetrafluorophosphate), BrOP (bromotris(dimethylamino)phosphonium hexafluorophosphate), DEPBT (3-(diethoxyphosphoryloxy)-1,2,3-benzotriazin-4(3H)-one), or PyBrOP (bromotris(pyrrolidino)phosphonium hexafluorophosphate). EDC, HOAT, BOP—Cl and PyBrOP are preferred peptide coupling reagents. The amount of peptide coupling reagent is in the range of about 1.0 to about 10.0 equivalents. Optional reagents that may be used in the amide bond-forming reaction include DMAP (4-dimethylaminopyridine) or active ester reagents, such as HOBT (1-hydroxybenzotriazole), HOAT (hydroxyazabenzotriazole), HOSu (hydroxysuccinimide), HONB (endo-N-hydroxy-5-nor-bornene-2,3-dicarboxamide), in amounts ranging from about 1.0 to about 10.0 equivalents.

Alternatively, one may treat an amine with a reactive equivalent of the $R_1$ carboxylic acid, such as RW—C(═O)$X^1$, $P_2$—C(═O)$X^1$, $P_3$-$L_2$-$P_2$—C(═O)$X^1$, or $P_4$-$L_3$-$P_3$-$L_2$-$P_2$—C(═O)$X^1$, wherein C(═O)$X^1$ is a group that is more reactive than COOH in the coupling reaction. Examples of —C(═O)$X^1$ groups include groups where $X^1$ is Cl, F, OC(═O)R(R is, e.g., aliphatic or aryl), —SH, —SR, —SAr, or —SeAr.

Acid and amine protecting groups as used herein are known in the art (see, e.g., T. W. Greene & P. G. M Wutz, "Protective Groups in Organic Synthesis," $3^{rd}$ Edition, John Wiley & Sons, Inc. (1999), and the earlier editions of this book. Examples of suitable protecting groups for acids include t-butoxy, benzyloxy, allyloxy and methoxymethoxy. Examples of suitable protecting groups for amines include 9-fluorenylmethyl carbamate, t-butyl carbamate, benzyl carbamate, trifluoroacetamide and p-toluenesulfonamide. A number of chemical groups are known that may be used as the RW—, $P_2$—, $P_3$-$L_2$-$P_2$, or $P_4$-$L_3$-$P_3$-$L_2$-$P_2$— portion of the protease inhibitor. Examples of such groups are reported in the following publications: WO 97/43310, US 20020016294, WO 01/81325, WO 02/08198, WO 01/77113, WO 02/08187, WO 02/08256, WO 02/08244, WO 03/006490, WO 01/74768, WO 99/50230, WO 98/17679, WO 02/48157, US 20020177725, WO 02/060926, US 20030008828, WO 02/48116, WO 01/64678, WO 01/07407, WO 98/46630, WO 00/59929, WO 99/07733, WO 00/09588, US 20020016442, WO 00/09543, WO 99/07734, U.S. Pat. No. 6,018,020, U.S. Pat. No. 6,265,380, U.S. Pat. No. 6,608,027, US 20020032175, US 20050080017, WO 98/22496, U.S. Pat. No. 5,866,684, WO 02/079234, WO 00/31129, WO 99/38888, WO 99/64442, WO 2004072243, and WO 02/18369, which are incorporated herein by reference in their entireties.

Although in Scheme V only a single stereoisomer is illustrated for the compound of Formula 4, the present invention is, however, intended to include all stereoisomers of Formula 4 which are depicted in Table I. All these stereoisomers can be prepared in the same method by using reagent(s) containing carbon atom(s) of a different steric configuration, e.g.,

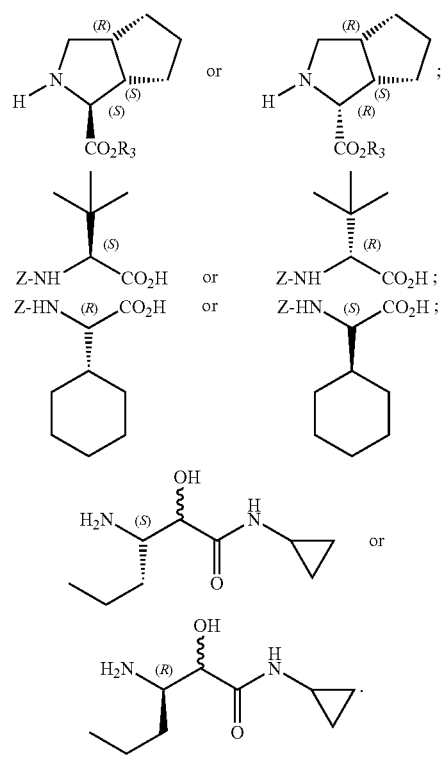

TABLE 1

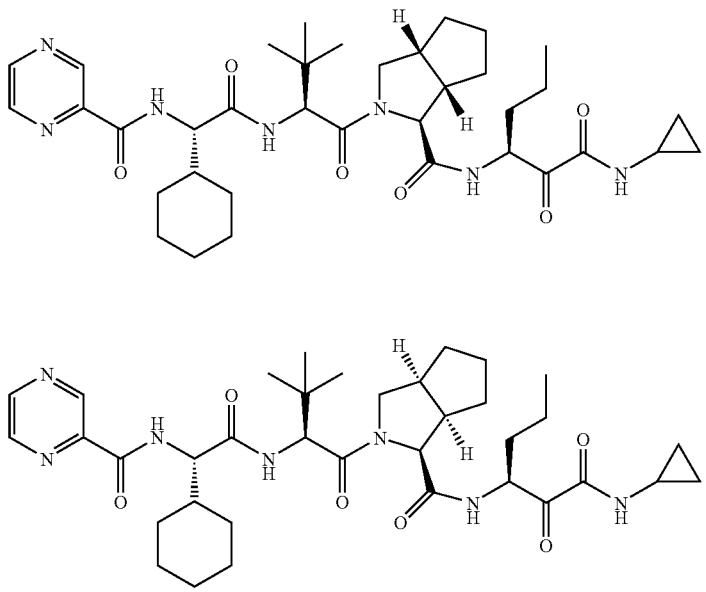

TABLE 1-continued
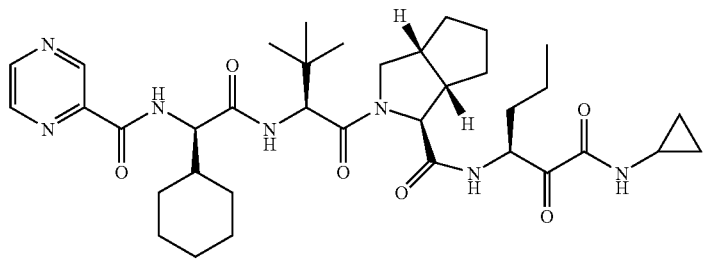 [SMILES: CCC[C@H](NC(=O)[C@@H]1[C@H]2CCC[C@H]2CN1C(=O)[C@@H](NC(=O)[C@H](NC(=O)c1cnccn1)C1CCCCC1)C(C)(C)C)C(=O)C(=O)NC1CC1]
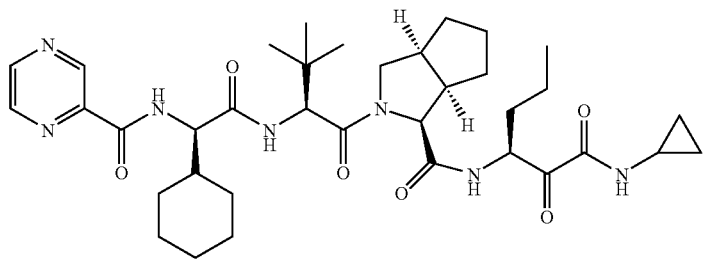 [SMILES: CCC[C@H](NC(=O)[C@@H]1[C@@H]2CCC[C@@H]2CN1C(=O)[C@@H](NC(=O)[C@H](NC(=O)c1cnccn1)C1CCCCC1)C(C)(C)C)C(=O)C(=O)NC1CC1]
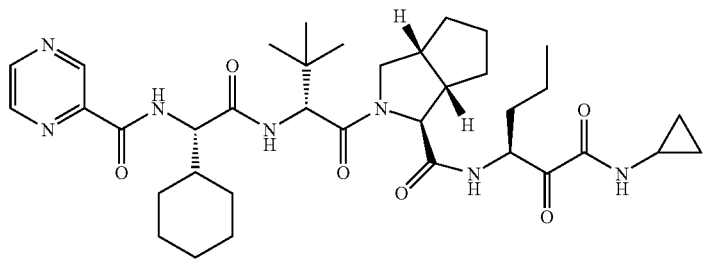 [SMILES: CCC[C@H](NC(=O)[C@@H]1[C@H]2CCC[C@H]2CN1C(=O)[C@H](NC(=O)[C@@H](NC(=O)c1cnccn1)C1CCCCC1)C(C)(C)C)C(=O)C(=O)NC1CC1]
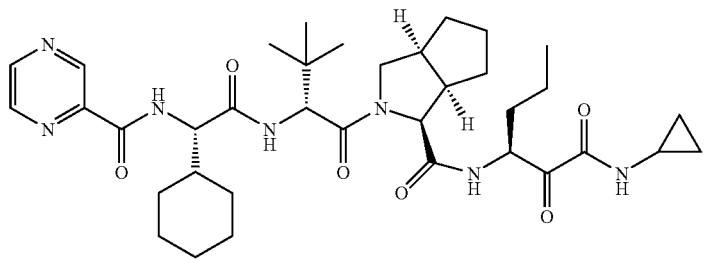 [SMILES: CCC[C@H](NC(=O)[C@@H]1[C@@H]2CCC[C@@H]2CN1C(=O)[C@H](NC(=O)[C@@H](NC(=O)c1cnccn1)C1CCCCC1)C(C)(C)C)C(=O)C(=O)NC1CC1]
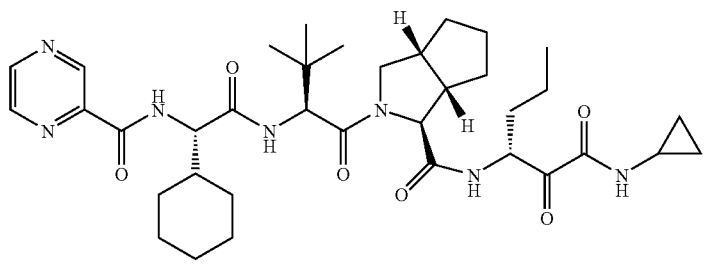 [SMILES: CCC[C@@H](NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1]
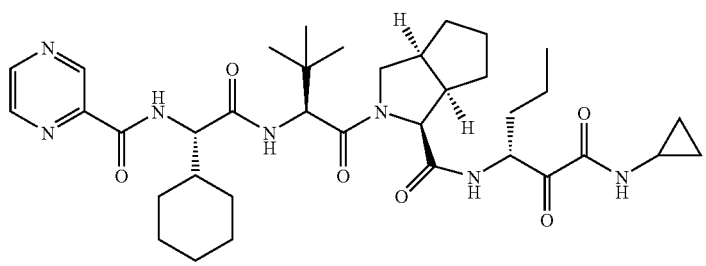 [SMILES: CCC[C@@H](NC(=O)[C@@H]1[C@@H]2CCC[C@@H]2CN1C(=O)[C@@H](NC(=O)[C@@H](NC(=O)c1cnccn1)C1CCCCC1)C(C)(C)C)C(=O)C(=O)NC1CC1]

TABLE 1-continued
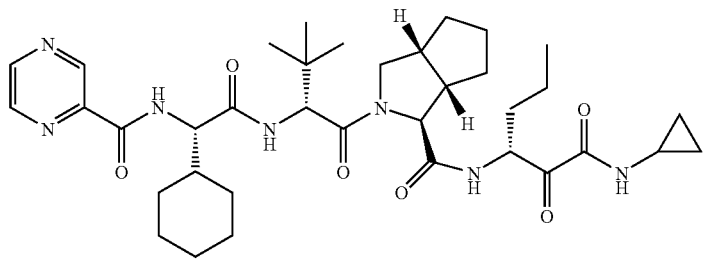 [SMILES: CCC[C@@H](NC(=O)[C@@H]1[C@H]2CCC[C@H]2CN1C(=O)[C@H](NC(=O)[C@@H](NC(=O)c1cnccn1)C1CCCCC1)C(C)(C)C)C(=O)C(=O)NC1CC1]
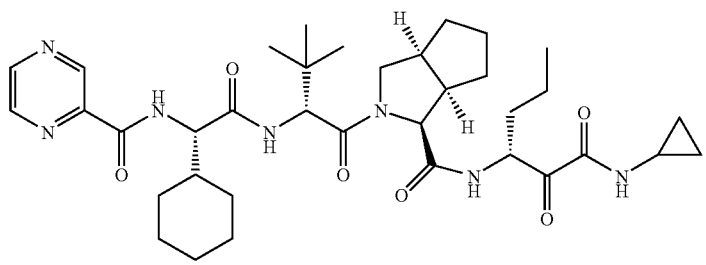 [SMILES: CCC[C@@H](NC(=O)[C@@H]1[C@@H]2CCC[C@@H]2CN1C(=O)[C@H](NC(=O)[C@@H](NC(=O)c1cnccn1)C1CCCCC1)C(C)(C)C)C(=O)C(=O)NC1CC1]
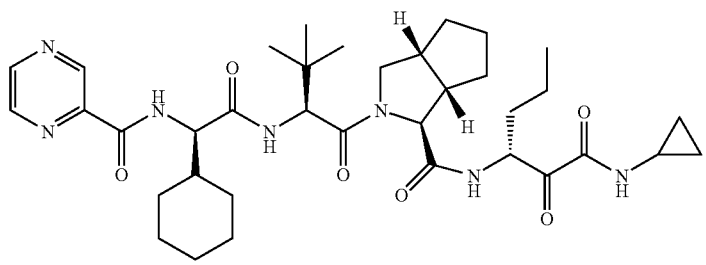 [SMILES: CCC[C@@H](NC(=O)[C@@H]1[C@H]2CCC[C@H]2CN1C(=O)[C@@H](NC(=O)[C@H](NC(=O)c1cnccn1)C1CCCCC1)C(C)(C)C)C(=O)C(=O)NC1CC1]
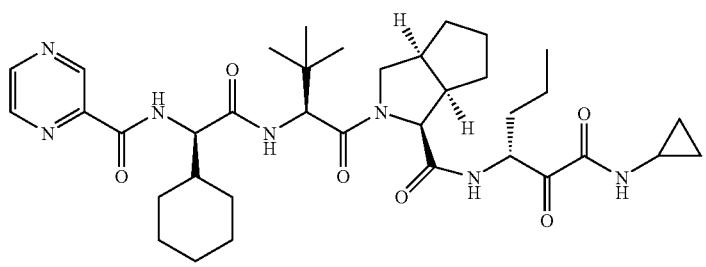 [SMILES: CCC[C@@H](NC(=O)[C@@H]1[C@@H]2CCC[C@@H]2CN1C(=O)[C@@H](NC(=O)[C@H](NC(=O)c1cnccn1)C1CCCCC1)C(C)(C)C)C(=O)C(=O)NC1CC1]
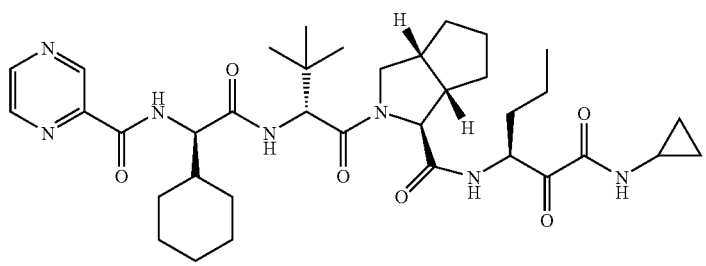 [SMILES: CCC[C@H](NC(=O)[C@@H]1[C@H]2CCC[C@H]2CN1C(=O)[C@H](NC(=O)[C@H](NC(=O)c1cnccn1)C1CCCCC1)C(C)(C)C)C(=O)C(=O)NC1CC1]
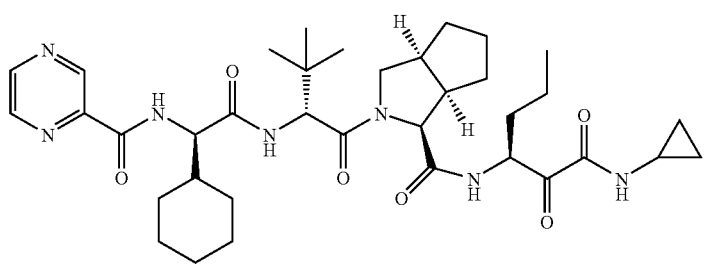 [SMILES: CCC[C@H](NC(=O)[C@@H]1[C@@H]2CCC[C@@H]2CN1C(=O)[C@H](NC(=O)[C@H](NC(=O)c1cnccn1)C1CCCCC1)C(C)(C)C)C(=O)C(=O)NC1CC1]

TABLE 1-continued
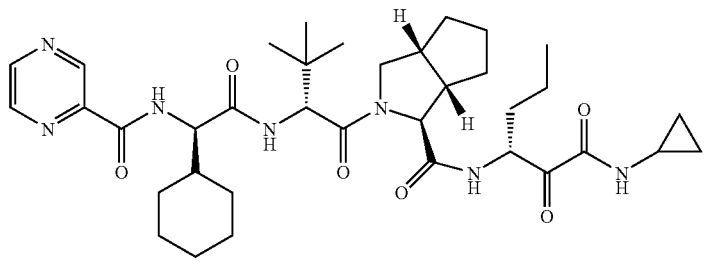 [SMILES: CCC[C@@H](NC(=O)[C@@H]1[C@H]2CCC[C@H]2CN1C(=O)[C@H](NC(=O)[C@H](NC(=O)c1cnccn1)C1CCCCC1)C(C)(C)C)C(=O)C(=O)NC1CC1]
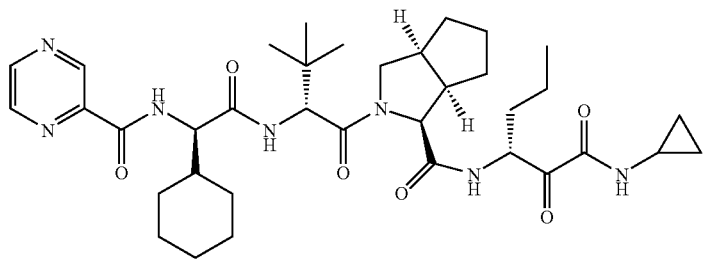 [SMILES: CCC[C@@H](NC(=O)[C@@H]1[C@@H]2CCC[C@@H]2CN1C(=O)[C@H](NC(=O)[C@H](NC(=O)c1cnccn1)C1CCCCC1)C(C)(C)C)C(=O)C(=O)NC1CC1]
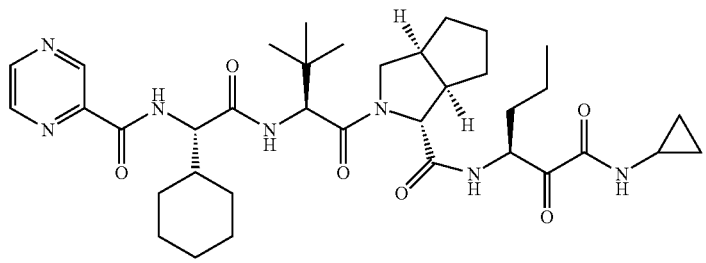 [SMILES: CCC[C@H](NC(=O)[C@H]1[C@@H]2CCC[C@@H]2CN1C(=O)[C@@H](NC(=O)[C@@H](NC(=O)c1cnccn1)C1CCCCC1)C(C)(C)C)C(=O)C(=O)NC1CC1]
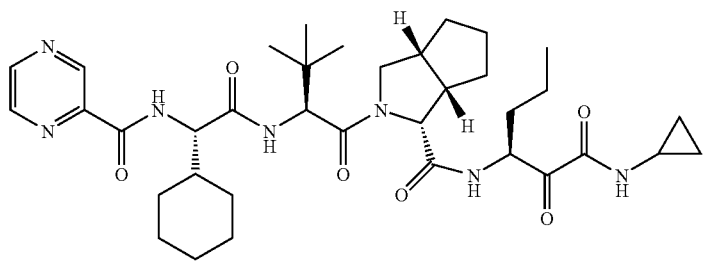 [SMILES: CCC[C@H](NC(=O)[C@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1]
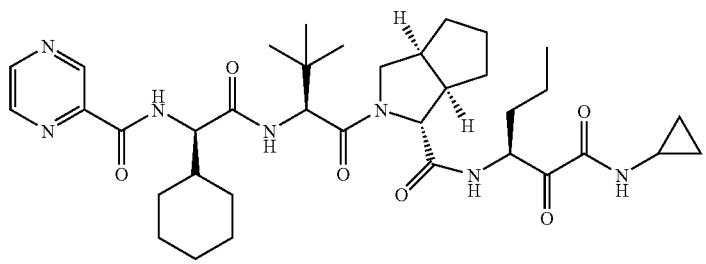 [SMILES: CCC[C@H](NC(=O)[C@H]1[C@@H]2CCC[C@@H]2CN1C(=O)[C@@H](NC(=O)[C@H](NC(=O)c1cnccn1)C1CCCCC1)C(C)(C)C)C(=O)C(=O)NC1CC1]
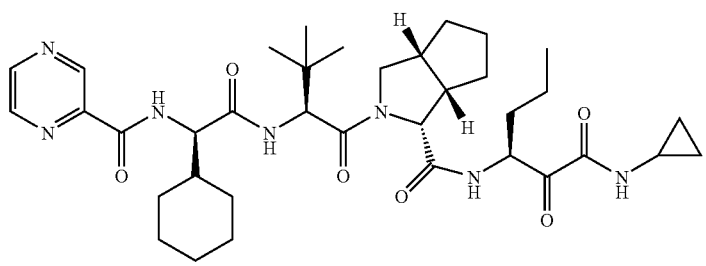 [SMILES: CCC[C@H](NC(=O)[C@H]1[C@H]2CCC[C@H]2CN1C(=O)[C@@H](NC(=O)[C@H](NC(=O)c1cnccn1)C1CCCCC1)C(C)(C)C)C(=O)C(=O)NC1CC1]

TABLE 1-continued
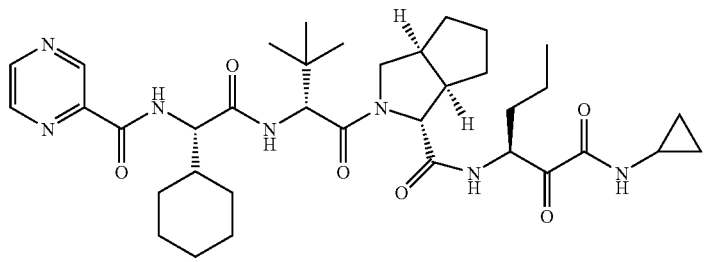 [SMILES: CCC[C@H](NC(=O)[C@H]1[C@@H]2CCC[C@@H]2CN1C(=O)[C@H](NC(=O)[C@@H](NC(=O)c1cnccn1)C1CCCCC1)C(C)(C)C)C(=O)C(=O)NC1CC1]
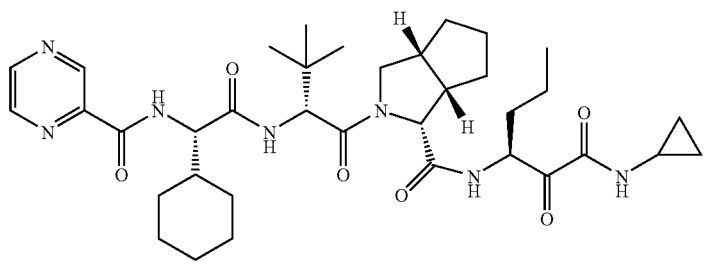 [SMILES: CCC[C@H](NC(=O)[C@H]1[C@H]2CCC[C@H]2CN1C(=O)[C@H](NC(=O)[C@@H](NC(=O)c1cnccn1)C1CCCCC1)C(C)(C)C)C(=O)C(=O)NC1CC1]
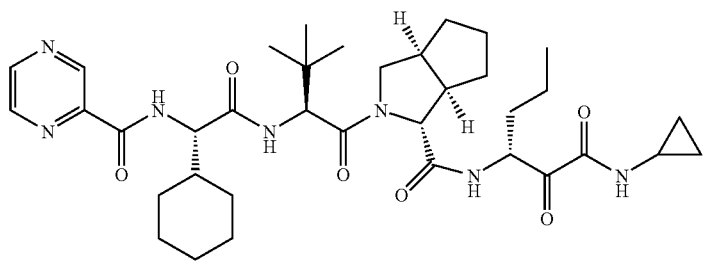 [SMILES: CCC[C@@H](NC(=O)[C@H]1[C@@H]2CCC[C@@H]2CN1C(=O)[C@@H](NC(=O)[C@@H](NC(=O)c1cnccn1)C1CCCCC1)C(C)(C)C)C(=O)C(=O)NC1CC1]
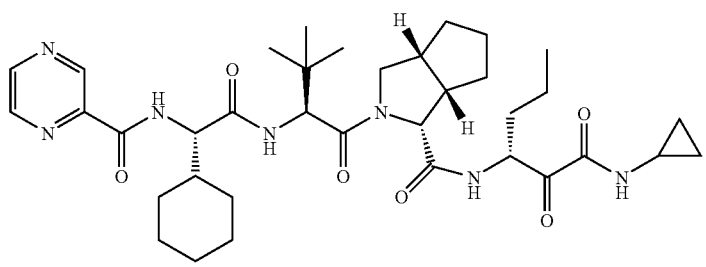 [SMILES: CCC[C@@H](NC(=O)[C@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1]
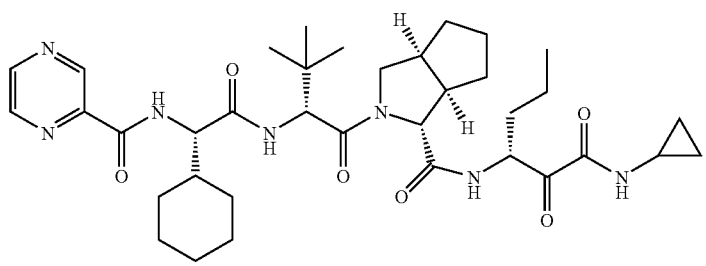 [SMILES: CCC[C@@H](NC(=O)[C@H]1[C@@H]2CCC[C@@H]2CN1C(=O)[C@H](NC(=O)[C@@H](NC(=O)c1cnccn1)C1CCCCC1)C(C)(C)C)C(=O)C(=O)NC1CC1]
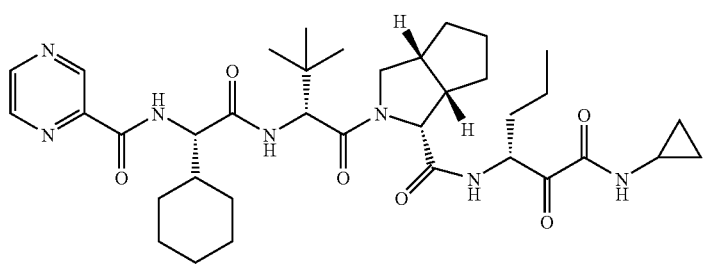 [SMILES: CCC[C@@H](NC(=O)[C@H]1[C@H]2CCC[C@H]2CN1C(=O)[C@H](NC(=O)[C@@H](NC(=O)c1cnccn1)C1CCCCC1)C(C)(C)C)C(=O)C(=O)NC1CC1]

TABLE 1-continued
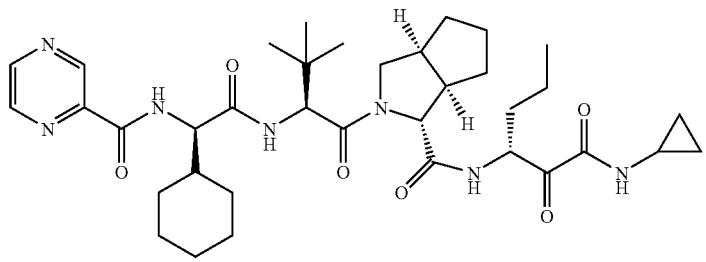 [SMILES: CCC[C@@H](NC(=O)[C@H]1[C@@H]2CCC[C@@H]2CN1C(=O)[C@@H](NC(=O)[C@H](NC(=O)c1cnccn1)C1CCCCC1)C(C)(C)C)C(=O)C(=O)NC1CC1]
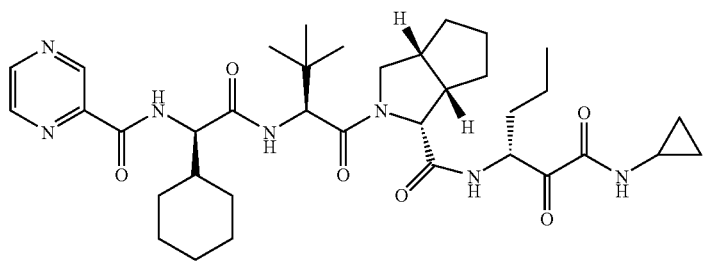 [SMILES: CCC[C@@H](NC(=O)[C@H]1[C@H]2CCC[C@H]2CN1C(=O)[C@@H](NC(=O)[C@H](NC(=O)c1cnccn1)C1CCCCC1)C(C)(C)C)C(=O)C(=O)NC1CC1]
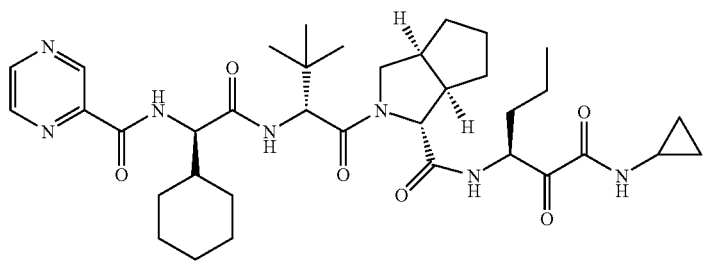 [SMILES: CCC[C@H](NC(=O)[C@H]1[C@@H]2CCC[C@@H]2CN1C(=O)[C@H](NC(=O)[C@H](NC(=O)c1cnccn1)C1CCCCC1)C(C)(C)C)C(=O)C(=O)NC1CC1]
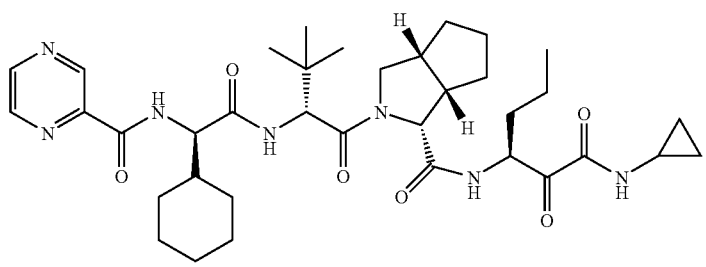 [SMILES: CCC[C@H](NC(=O)[C@H]1[C@H]2CCC[C@H]2CN1C(=O)[C@H](NC(=O)[C@H](NC(=O)c1cnccn1)C1CCCCC1)C(C)(C)C)C(=O)C(=O)NC1CC1]
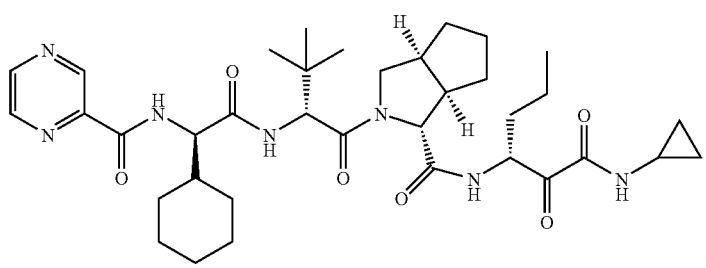 [SMILES: CCC[C@@H](NC(=O)[C@H]1[C@@H]2CCC[C@@H]2CN1C(=O)[C@H](NC(=O)[C@H](NC(=O)c1cnccn1)C1CCCCC1)C(C)(C)C)C(=O)C(=O)NC1CC1]
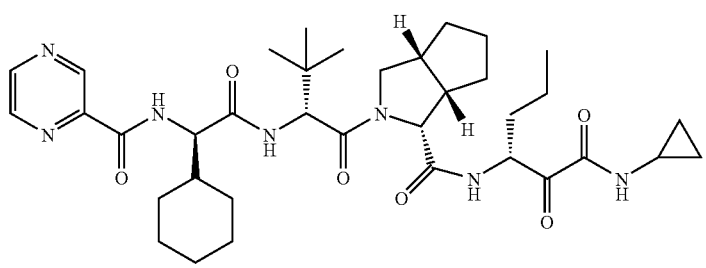 [SMILES: CCC[C@@H](NC(=O)[C@H]1[C@H]2CCC[C@H]2CN1C(=O)[C@H](NC(=O)[C@H](NC(=O)c1cnccn1)C1CCCCC1)C(C)(C)C)C(=O)C(=O)NC1CC1]

TABLE 1-continued
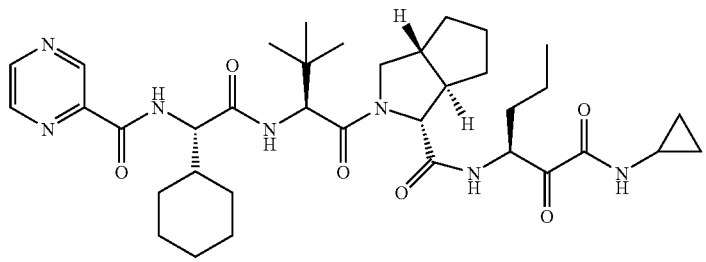 [SMILES: CCC[C@H](NC(=O)[C@H]1[C@@H]2CCC[C@H]2CN1C(=O)[C@@H](NC(=O)[C@@H](NC(=O)c1cnccn1)C1CCCCC1)C(C)(C)C)C(=O)C(=O)NC1CC1]
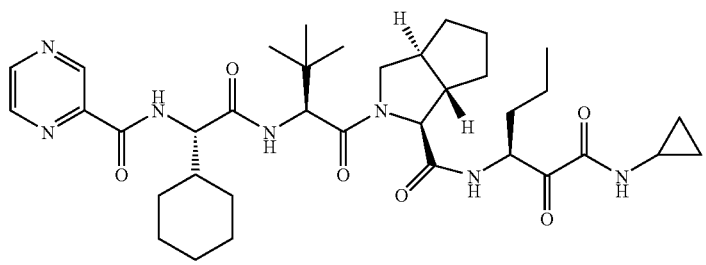 [SMILES: CCC[C@H](NC(=O)[C@@H]1[C@H]2CCC[C@@H]2CN1C(=O)[C@@H](NC(=O)[C@@H](NC(=O)c1cnccn1)C1CCCCC1)C(C)(C)C)C(=O)C(=O)NC1CC1]
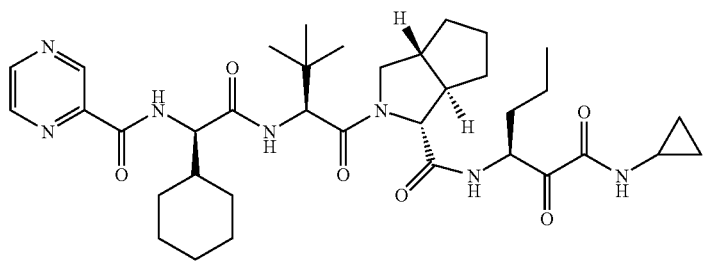 [SMILES: CCC[C@H](NC(=O)[C@H]1[C@@H]2CCC[C@H]2CN1C(=O)[C@@H](NC(=O)[C@H](NC(=O)c1cnccn1)C1CCCCC1)C(C)(C)C)C(=O)C(=O)NC1CC1]
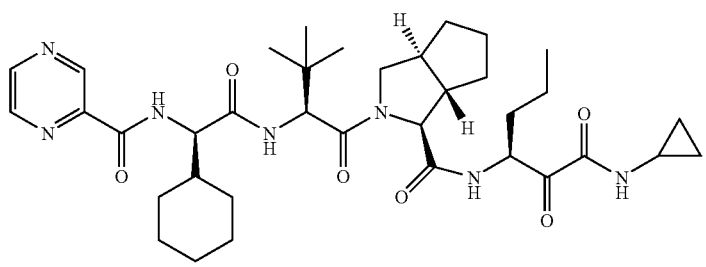 [SMILES: CCC[C@H](NC(=O)[C@@H]1[C@H]2CCC[C@@H]2CN1C(=O)[C@@H](NC(=O)[C@H](NC(=O)c1cnccn1)C1CCCCC1)C(C)(C)C)C(=O)C(=O)NC1CC1]
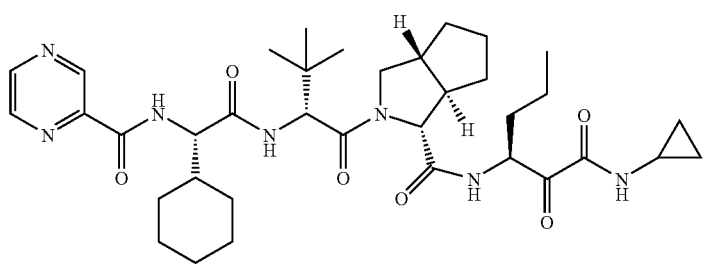 [SMILES: CCC[C@H](NC(=O)[C@H]1[C@@H]2CCC[C@H]2CN1C(=O)[C@H](NC(=O)[C@@H](NC(=O)c1cnccn1)C1CCCCC1)C(C)(C)C)C(=O)C(=O)NC1CC1]
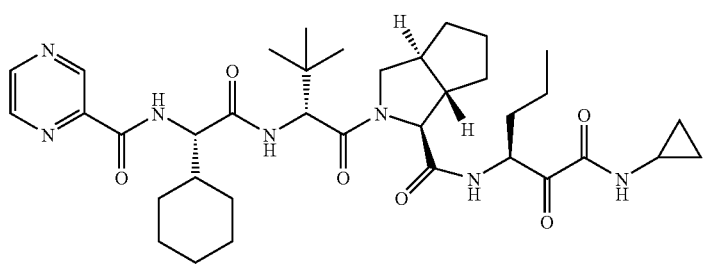 [SMILES: CCC[C@H](NC(=O)[C@@H]1[C@H]2CCC[C@@H]2CN1C(=O)[C@H](NC(=O)[C@@H](NC(=O)c1cnccn1)C1CCCCC1)C(C)(C)C)C(=O)C(=O)NC1CC1]

TABLE 1-continued
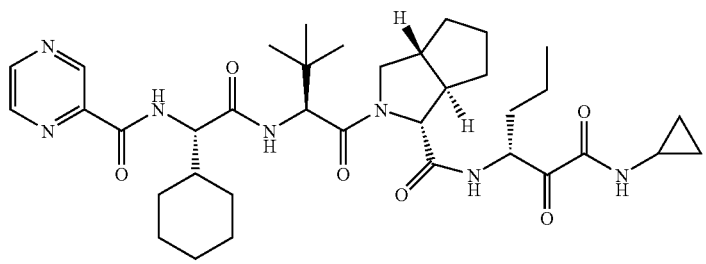 [SMILES: CCC[C@@H](NC(=O)[C@H]1[C@@H]2CCC[C@H]2CN1C(=O)[C@@H](NC(=O)[C@@H](NC(=O)c1cnccn1)C1CCCCC1)C(C)(C)C)C(=O)C(=O)NC1CC1]
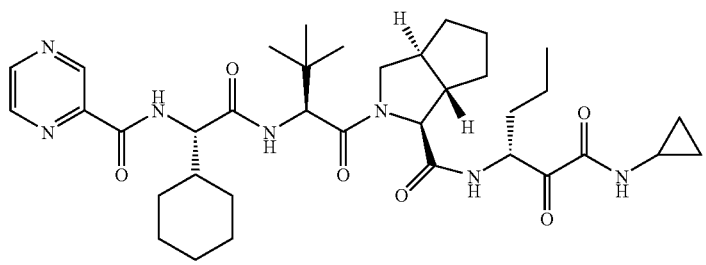 [SMILES: CCC[C@@H](NC(=O)[C@@H]1[C@H]2CCC[C@@H]2CN1C(=O)[C@@H](NC(=O)[C@@H](NC(=O)c1cnccn1)C1CCCCC1)C(C)(C)C)C(=O)C(=O)NC1CC1]
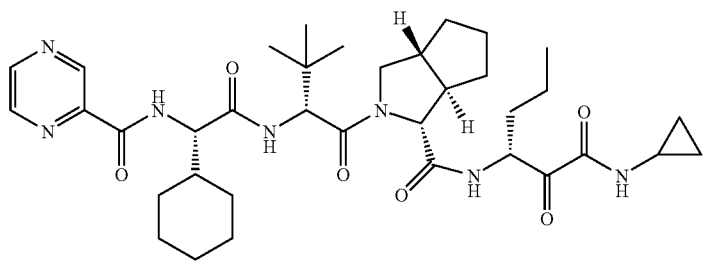 [SMILES: CCC[C@@H](NC(=O)[C@H]1[C@@H]2CCC[C@H]2CN1C(=O)[C@H](NC(=O)[C@@H](NC(=O)c1cnccn1)C1CCCCC1)C(C)(C)C)C(=O)C(=O)NC1CC1]
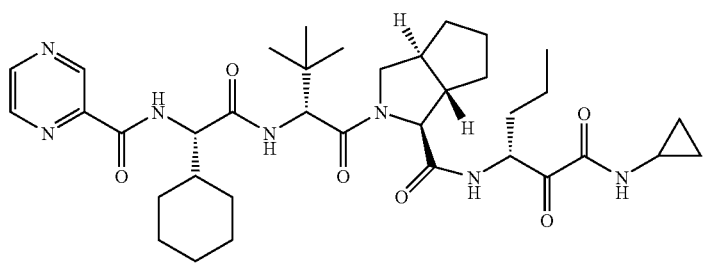 [SMILES: CCC[C@@H](NC(=O)[C@@H]1[C@H]2CCC[C@@H]2CN1C(=O)[C@H](NC(=O)[C@@H](NC(=O)c1cnccn1)C1CCCCC1)C(C)(C)C)C(=O)C(=O)NC1CC1]
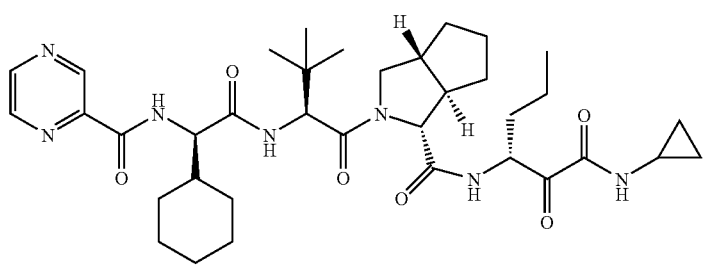 [SMILES: CCC[C@@H](NC(=O)[C@H]1[C@@H]2CCC[C@H]2CN1C(=O)[C@@H](NC(=O)[C@H](NC(=O)c1cnccn1)C1CCCCC1)C(C)(C)C)C(=O)C(=O)NC1CC1]
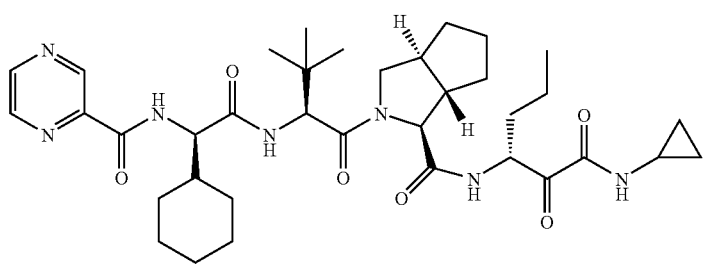 [SMILES: CCC[C@@H](NC(=O)[C@@H]1[C@H]2CCC[C@@H]2CN1C(=O)[C@@H](NC(=O)[C@H](NC(=O)c1cnccn1)C1CCCCC1)C(C)(C)C)C(=O)C(=O)NC1CC1]

TABLE 1-continued
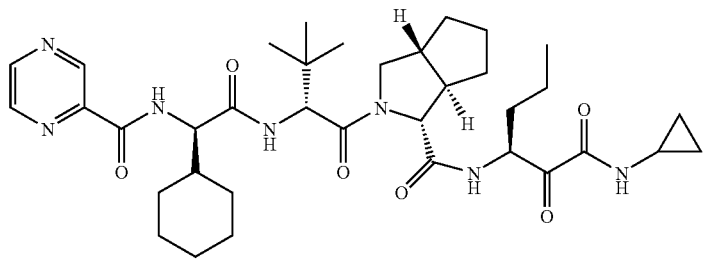 [SMILES: CCC[C@H](NC(=O)[C@H]1[C@@H]2CCC[C@H]2CN1C(=O)[C@H](NC(=O)[C@H](NC(=O)c1cnccn1)C1CCCCC1)C(C)(C)C)C(=O)C(=O)NC1CC1]
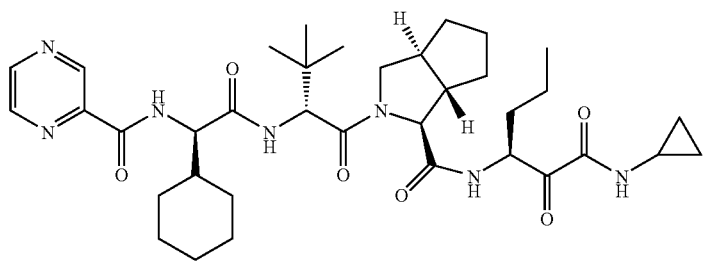 [SMILES: CCC[C@H](NC(=O)[C@@H]1[C@H]2CCC[C@@H]2CN1C(=O)[C@H](NC(=O)[C@H](NC(=O)c1cnccn1)C1CCCCC1)C(C)(C)C)C(=O)C(=O)NC1CC1]
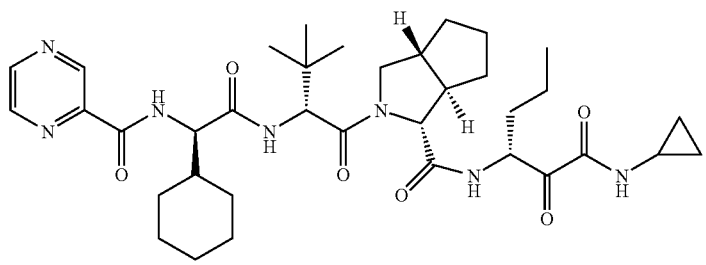 [SMILES: CCC[C@@H](NC(=O)[C@H]1[C@@H]2CCC[C@H]2CN1C(=O)[C@H](NC(=O)[C@H](NC(=O)c1cnccn1)C1CCCCC1)C(C)(C)C)C(=O)C(=O)NC1CC1]
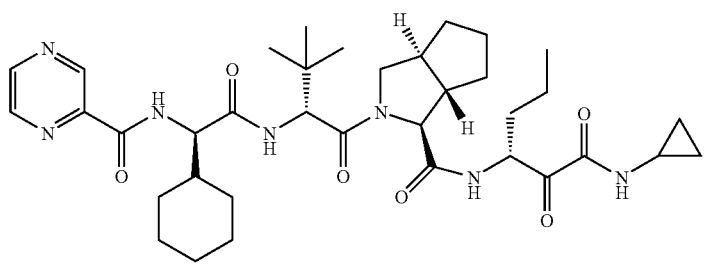 [SMILES: CCC[C@@H](NC(=O)[C@@H]1[C@H]2CCC[C@@H]2CN1C(=O)[C@H](NC(=O)[C@H](NC(=O)c1cnccn1)C1CCCCC1)C(C)(C)C)C(=O)C(=O)NC1CC1]
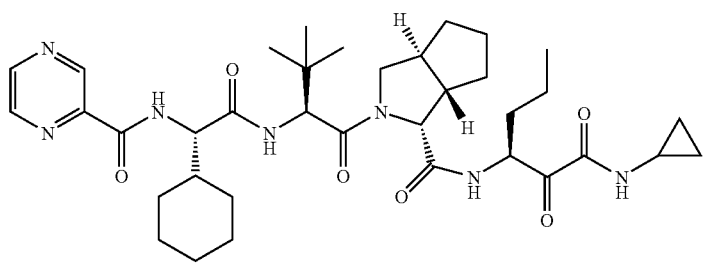 [SMILES: CCC[C@H](NC(=O)[C@H]1[C@H]2CCC[C@@H]2CN1C(=O)[C@@H](NC(=O)[C@@H](NC(=O)c1cnccn1)C1CCCCC1)C(C)(C)C)C(=O)C(=O)NC1CC1]
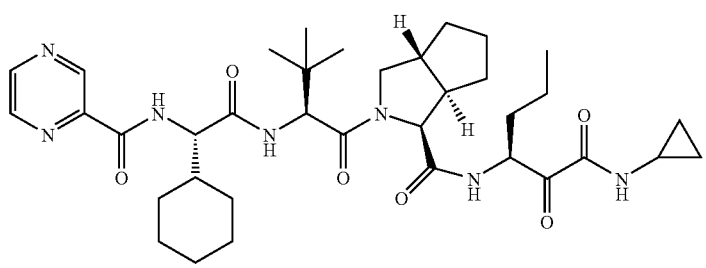 [SMILES: CCC[C@H](NC(=O)[C@@H]1[C@@H]2CCC[C@H]2CN1C(=O)[C@@H](NC(=O)[C@@H](NC(=O)c1cnccn1)C1CCCCC1)C(C)(C)C)C(=O)C(=O)NC1CC1]

TABLE 1-continued
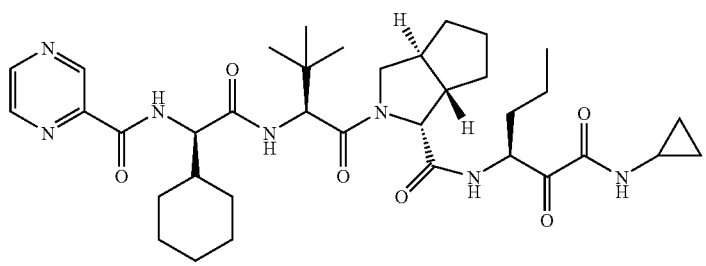 [SMILES: CCC[C@H](NC(=O)[C@H]1[C@H]2CCC[C@@H]2CN1C(=O)[C@@H](NC(=O)[C@H](NC(=O)c1cnccn1)C1CCCCC1)C(C)(C)C)C(=O)C(=O)NC1CC1]
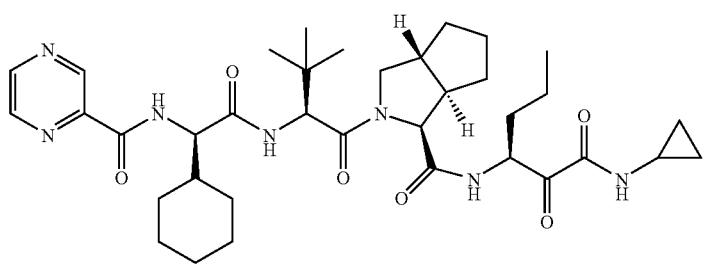 [SMILES: CCC[C@H](NC(=O)[C@@H]1[C@@H]2CCC[C@H]2CN1C(=O)[C@@H](NC(=O)[C@H](NC(=O)c1cnccn1)C1CCCCC1)C(C)(C)C)C(=O)C(=O)NC1CC1]
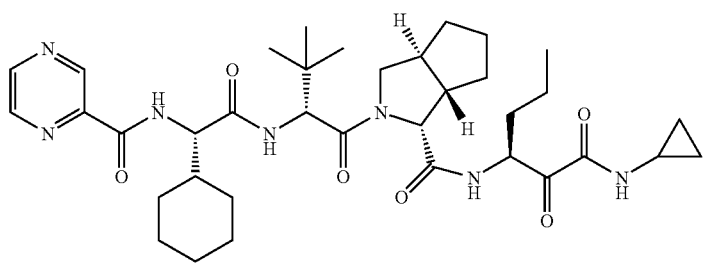 [SMILES: CCC[C@H](NC(=O)[C@H]1[C@H]2CCC[C@@H]2CN1C(=O)[C@H](NC(=O)[C@@H](NC(=O)c1cnccn1)C1CCCCC1)C(C)(C)C)C(=O)C(=O)NC1CC1]
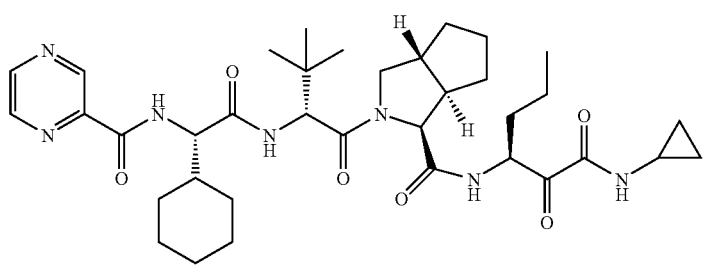 [SMILES: CCC[C@H](NC(=O)[C@@H]1[C@@H]2CCC[C@H]2CN1C(=O)[C@H](NC(=O)[C@@H](NC(=O)c1cnccn1)C1CCCCC1)C(C)(C)C)C(=O)C(=O)NC1CC1]
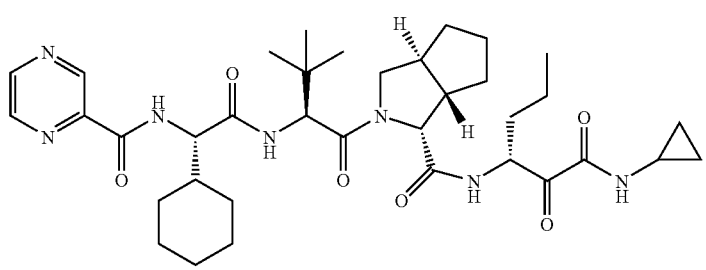 [SMILES: CCC[C@@H](NC(=O)[C@H]1[C@H]2CCC[C@@H]2CN1C(=O)[C@@H](NC(=O)[C@@H](NC(=O)c1cnccn1)C1CCCCC1)C(C)(C)C)C(=O)C(=O)NC1CC1]
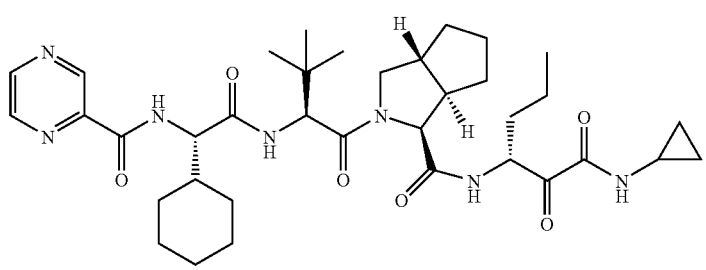 [SMILES: CCC[C@@H](NC(=O)[C@@H]1[C@@H]2CCC[C@H]2CN1C(=O)[C@@H](NC(=O)[C@@H](NC(=O)c1cnccn1)C1CCCCC1)C(C)(C)C)C(=O)C(=O)NC1CC1]

TABLE 1-continued
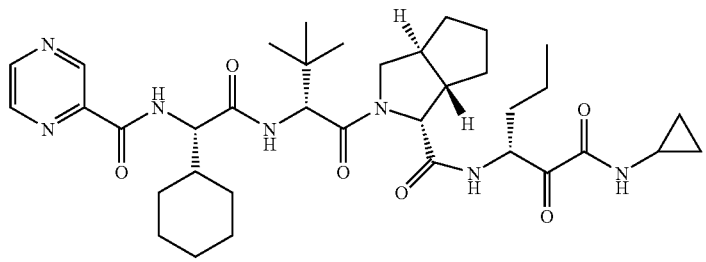 [SMILES: CCC[C@@H](NC(=O)[C@H]1[C@H]2CCC[C@@H]2CN1C(=O)[C@H](NC(=O)[C@@H](NC(=O)c1cnccn1)C1CCCCC1)C(C)(C)C)C(=O)C(=O)NC1CC1]
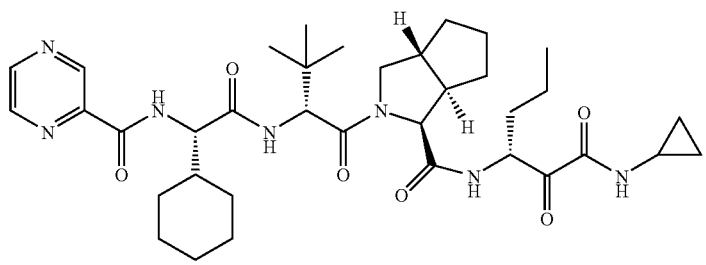 [SMILES: CCC[C@@H](NC(=O)[C@@H]1[C@@H]2CCC[C@H]2CN1C(=O)[C@H](NC(=O)[C@@H](NC(=O)c1cnccn1)C1CCCCC1)C(C)(C)C)C(=O)C(=O)NC1CC1]
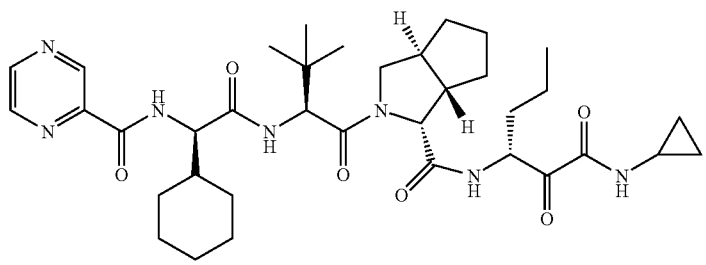 [SMILES: CCC[C@@H](NC(=O)[C@H]1[C@H]2CCC[C@@H]2CN1C(=O)[C@@H](NC(=O)[C@H](NC(=O)c1cnccn1)C1CCCCC1)C(C)(C)C)C(=O)C(=O)NC1CC1]
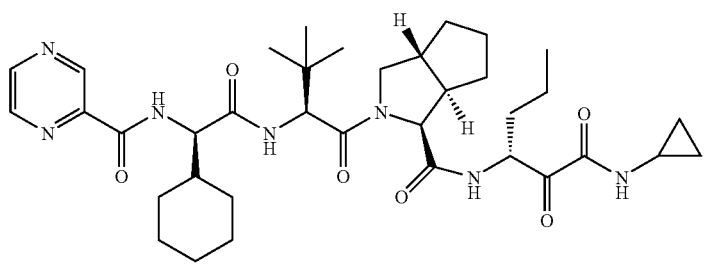 [SMILES: CCC[C@@H](NC(=O)[C@@H]1[C@@H]2CCC[C@H]2CN1C(=O)[C@@H](NC(=O)[C@H](NC(=O)c1cnccn1)C1CCCCC1)C(C)(C)C)C(=O)C(=O)NC1CC1]
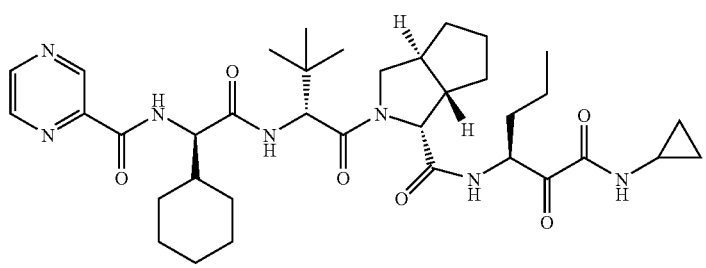 [SMILES: CCC[C@H](NC(=O)[C@H]1[C@H]2CCC[C@@H]2CN1C(=O)[C@H](NC(=O)[C@H](NC(=O)c1cnccn1)C1CCCCC1)C(C)(C)C)C(=O)C(=O)NC1CC1]
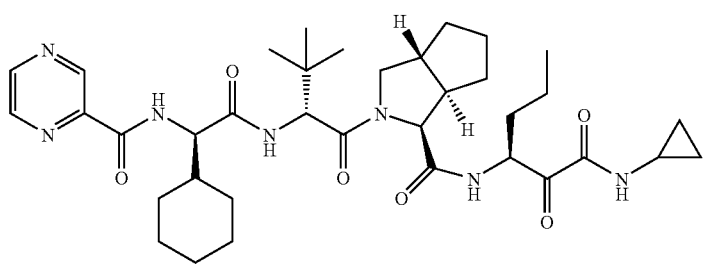 [SMILES: CCC[C@H](NC(=O)[C@@H]1[C@@H]2CCC[C@H]2CN1C(=O)[C@H](NC(=O)[C@H](NC(=O)c1cnccn1)C1CCCCC1)C(C)(C)C)C(=O)C(=O)NC1CC1]

TABLE 1-continued

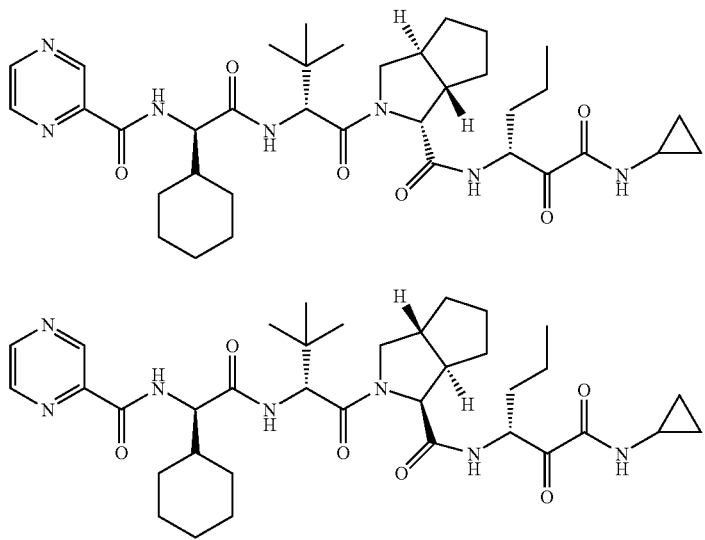

III. Examples

The following preparative examples are set forth in order that this invention be more fully understood. These examples are for the purpose of illustration only and are not to be construed as limiting the scope of the invention in any way.

Preparation 1:
3,7-dipropyl-3,7-diazabicyclo[3.3.1]nonane

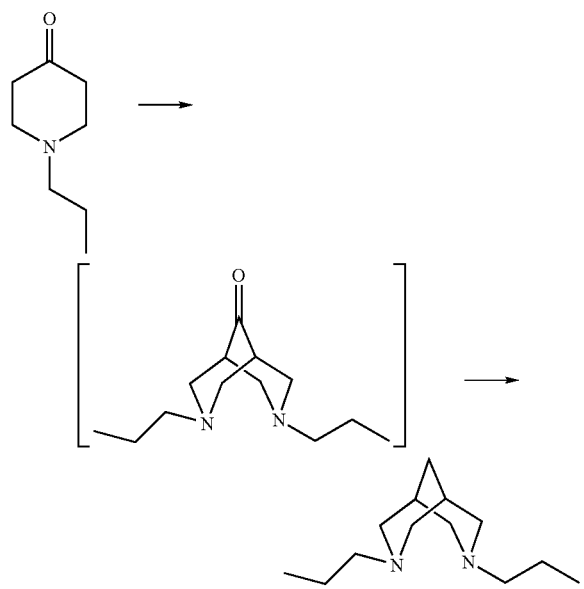

Method 1

To a three-neck 5 L flask equipped with a mechanical stirrer, thermocouple, condenser, and addition funnel, under a nitrogen atmosphere, was charged 1-propyl-4-piperidone (100 g, 0.71 mol), parafounaldehyde (50 g, 1.67 mol), and ethyl alcohol (2.0 L) with stirring. Acetic acid (90 mL, 1.56 mol) was charged and the mixture was warmed to 40° C. In a separate flask was dissolved propylamine (64 mL, 0.78 mol) in ethyl alcohol (500 mL). This solution was added to the above mixture over 7-8 hours. The mixture was stirred for an additional 1.5 hours at 40° C., then cooled to ambient temperature. The mixture was filtered through a pad of Celite®, and the Celite® was rinsed with ethyl alcohol (twice, 100 mL each). The solution was concentrated in vacuo and diethyleneglycol (1.0 L) was added. In a separate flask potassium hydroxide (160 g) was dissolved in water (190 mL). The solution was added to the diethyleneglycol mixture, with stirring, then the mixture was warmed to 85° C. Hydrazine monohydrate (96 mL) was added over 2 hours, and the resultant mixture was stirred at 85° C. for another 1 hour. With nitrogen sparging, the mixture was warmed to 160° C. bath temperature while collecting the distillate in a Dean-Stark trap. The lower aqueous phase was returned to the reaction flask while the upper product phase collected. The process was repeated until the product no longer distilled as an azeotrope with water. The pot temperature varied from 135 to 160° C. during the process. The collected upper-phase fractions were combined and dissolved in heptane (160 mL). The solution was washed with water (twice, 120 mL each), and the combined aqueous phases were extracted with heptane (twice, 100 mL each). The combined organic phases were concentrated to give the title compound.

$^1$H NMR (DMSO-$d_6$, 500 MHz): δ 2.60 (dd, J=10.88, 2.04 Hz, 4H), 2.23 (dd, J=10.88, 4.58 Hz, 4H), 2.12 (t, J=7.74 Hz, 4H), 1.91-1.84 (m, 2H), 1.44-1.35 (m, 6H), 0.85 (t, J=7.25 Hz, 6H)

Method 2

Under nitrogen atmosphere, acetic acid (260 mL, 4.67 mol) was added to a mixture of 1-propyl-4-piperidone (300 g, 2.12 mol), paraformaldehyde (150 g, 5.00 mol), and ethyl alcohol (6.00 L) in a four-neck 12 L flask equipped with a mechanical stirrer, a thermocouple, and a condenser. The heterogeneous mixture was warmed to 40° C. and a solution of propylamine (192 mL, 2.34 mol) in ethyl alcohol (1.50 L) was added over a period of 7.5 hours. The mixture was maintained at 40° C. for 1.5 hours after the addition was finished. The mixture was cooled to 22 to 25° C. and filtered. The collected solids were washed with ethyl alcohol (twice, 200 mL each) and the combined filtrates concentrated to about 1.0 L under vacuum distillation (90 mmHg, 50 to 55° C.). Diethyleneglycol (2.60 L) was added, followed by a solution of potassium hydroxide (477 g) in water (570 mL). The reaction mixture was heated to 85° C. and hydrazine monohydrate (279 mL) was added over 2 hours. Heating at 85° C. was continued for 1 hour after the addition was finished then the mixture was heated to 155° C. while collecting the distillate which formed two layers. The lower layer was returned periodically to the reaction mixture. Heating at 155-165° C. was continued until the distillation of the upper layer ceased. The upper product layer was diluted with heptane (480 mL) and washed with water (twice, 240 mL each) The combined aqueous phases were extracted with heptane (twice, 300 mL each). The combined heptane extracts were concentrated to provide the title compound as a straw colored liquid.

Preparation 2:
(S)-3-amino-N-cyclopropyl-2-hydroxyhexanamide
(18)

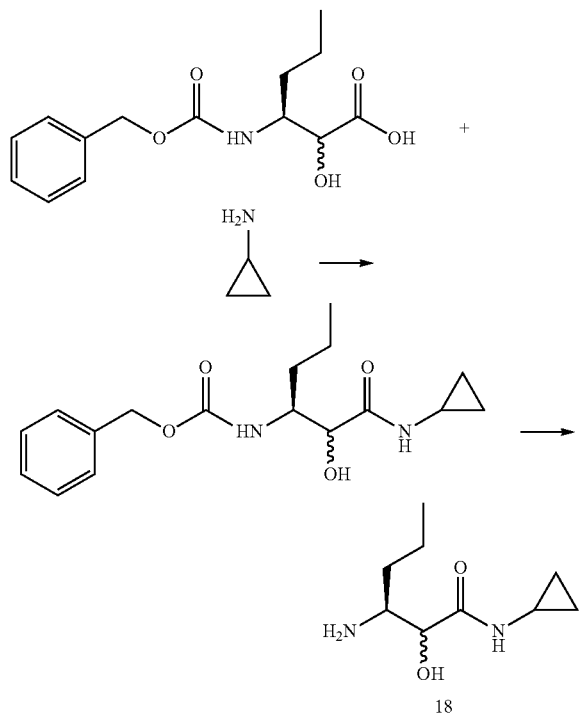

A 250 mL round bottomed flask equipped with an overhead stirrer, addition funnel, thermocouple, and nitrogen/hydrogen inlet was purged with nitrogen for several minutes. The protected amino-hydroxy acid (10.0 g, 0.035 mol) and N-hydroxysuccinimide (9.0 g, 0.078 mol, 2.2 molar eq.) were added to the flask followed by 105 mL of DMF. The mixture was agitated at 20±5° C. until a clear solution was obtained (approximately 15 minutes). The flask was cooled to −9.8° C. (ice/acetone bath). EDC.HCl (13.6 g, 0.071 mol, 2.0 molar eq.) was added to the flask in one portion. The contents of the flask were allowed to stir at −5±5° C. for 3 hours. The contents of the reaction flask were cooled to −10±3° C. and cyclopropylamine (4.89 g, 0.085 mol, 2.4 molar eq.) was added via an addition funnel while maintaining a temperature range of 5±3° C. The reaction mixture was allowed to stir at 5±5° C. for 60 minutes then slowly warmed to room temperature and stirred overnight. The reaction mixture was transferred to a larger round bottom flask and quenched with the addition of water (270 mL) at room temperature. The DMF/water layer was extracted with three portions of EtOAc (150 mL) at 35-40° C., the combined EtOAc extracts were washed with water (twice, 300 mL each), followed by 10% NaHCO$_3$ solution (300 mL), and finally water (300 mL). The EtOAc layer was concentrated at atmospheric pressure and heptane (100 mL) was added. Distillation at 80±5° C. was continued and additional heptane (50 mL) was added to crystallize the product from solution. The mixture was held at 85° C. for 2 hours, slowly cooled to room temperature, and held for 1 hour. The product was vacuum filtered and dried at 25 mmHg overnight at 30° C. to give a crude product (12.86 g). An 11.44 g portion of the crude product was placed in a 250 mL round bottom flask, 50 mL of MTBE was added, and the thick slurry was stirred for 3 hours at room temperature. The product was filtered and the cake washed with MTBE (50 mL). The dried product (6.4 g) was sampled for wt % assay (92.2 wt %) and HPLC A % (100 A %).

A 1.0 L Buchi hydrogenation vessel equipped with an overhead stirrer, ballast tank, thermocouple, and nitrogen/hydrogen inlet was purged with nitrogen for several minutes. The protected amino-hydroxy amide (49.9 g, 0.156 mol, prepared as described above), and 20% Pd(OH)$_2$ on carbon (2.85 g, 0.002 mol, 50% water by weight) were charged to the vessel followed by 700 mL of MeOH. The mixture was agitated at 40° C. until the starting material dissolved (approximately 15 minutes). The vessel and ballast tank were purged 2 times to 40 psig with nitrogen, vented to atmospheric pressure with nitrogen, and pressurized to 40 psig with hydrogen 2 times, venting to atmosphere each time. The ballast tank was finally pressurized to 400 psig and the vessel was pressurized to 30 psig via the ballast tank. The hydrogenation vessel was held at 40° C. and 30 psig hydrogen (by regulation via ballast tank) for 2 hours. The vessel was vented to atmospheric pressure with nitrogen and the slurry was sampled for HPLC analysis for residual starting material (1.8%; limit=0.5% both diastereomers). The vessel was re-purged and re-pressurized to 30 psig with hydrogen and held at 40° C. for additional 30 minutes. The vessel was vented to atmospheric pressure with nitrogen and a sample of the slurry was submitted for HPLC analysis for residual amino-amide (1.1%; limit=0.5% both diastereomers). The vessel was re-purged and re-pressurized with hydrogen and held at 40° C. for an additional 40 min. The vessel was vented to atmospheric pressure and held overnight under a nitrogen atmosphere.

A sample was submitted for HPLC analysis for residual protected amino-hydroxy amide (none detected; limit≦0.5% both diastereomers). A portion of the product crystallized out of solution during the overnight stir and an additional 300 mL of MeOH was added to dissolve the product. The slurry was warmed to 45° C. to assure dissolution, then filtered over a bed of Celite® at 45° C. The wet filter cake was rinsed with MeOH (250 mL) and the filtrate was distilled at atmospheric pressure to a volume of approximately 150 mL. Ethyl acetate (300 mL) was added and distillation was continued at atmospheric pressure, again to a volume of 150 mL. This procedure was repeated twice more. Heptane (150 mL) was added to the flask at 75° C. and the contents were cooled to room temperature and ultimately to 5° C. in an ice/water bath. The crystallized product was collected, the wet cake was washed with heptane (75 mL) and dried at 40° C. under reduced pressure overnight. The free amino-amide was isolated as an off-white solid (21.2 g, 0.114 mol, 73.1% yield) with an HPLC purity of 98.5 A % and a wt/wt assay of 94.2 wt %.

Example 1

N-t-butyloxycarbonyl-3-azabicyclo[3.3.0]octane (6)

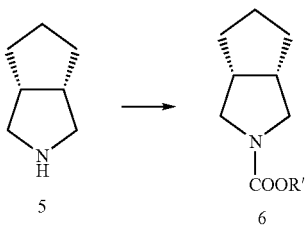

Method 1

To a 2 L 3-necked round-bottom flask under nitrogen fitted with a mechanical stirrer, a 500 mL addition funnel, and a thermometer was charged 3-azabicyclo[3.3.0]nonane hydrochloride (100 g, 0.677 mol), potassium carbonate (187 g, 1.35 mol), 1-butyl methyl ether (220 mL) and water (160 mL), with stirring. The mixture was cooled to 14-16° C. In a separate 500 mL Erlenmeyer flask was charged $Boc_2O$ (di-t-butyl dicarbonate) (145 g, 0.644 mol) and t-butyl methyl ether (190 mL). The mixture was stirred until complete dissolution was obtained. The solution was poured into the addition funnel and added to the above reaction mixture, keeping the reaction temperature below 25° C. Water (290 mL) was added to dissolve solids, and the mixture was stirred for 10-15 minutes. After separating the lower aqueous phase, the organic phase was washed with 5% aq. $NaHSO_4$ (twice, 145 mL each), then water (145 mL). The organic phase was concentrated and methyl t-butyl ether was added (1.3 L) to give a solution of the title compound in t-butyl methyl ether. See, e.g., R. Griot, *Helv. Chim. Acta.*, 42, 67 (1959).

Method 2

A solution of potassium carbonate (187 g, 1.35 mol) in water (160 mL) was added to a mixture of 3-azabicyclo[3.3.0]octane hydrochloride (100 g, 0.677 mol) and t-butyl methyl ether (220 mL), and the resultant mixture was cooled to 14-16° C. A solution of $Boc_2O$ (145 g, 0.644 mol) in t-butyl methyl ether (190 mL) was added while maintaining a temperature below 35° C. After the addition, the mixture was stirred for 1 hour then filtered. The solids were washed with MTBE (50 mL). The phases were separated and the organic phase washed with 5% aq. $NaHSO_4$ (twice, 145 mL each) and water (145 mL) and concentrated to 300 mL under vacuum. MTBE (300 mL) was added and the mixture concentrated to remove water to less than 550 ppm. The concentrate was diluted with MTBE (400 mL) to provide a solution of the title compound in MTBE.

Example 2 rac-2-butoxycarbonyl)octahydracyclpenta[c]pyrrole-1-carboxylic acid (7)

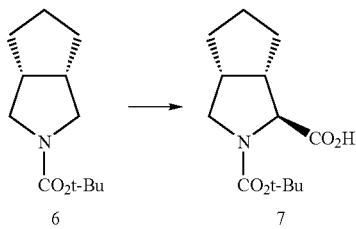 [SMILES: CC(C)(C)OC(=O)N1C[C@H]2CCC[C@H]2C1 ; CC(C)(C)OC(=O)N1C[C@@H]2CCC[C@@H]2[C@H]1C(=O)O]

Method 1

The solution from Example 1, Method 1, was charged to a 5 L 4-necked flask fitted with a mechanical stirrer, an addition funnel, a ReactIR probe, and a thermometer. 3,7-Dipropyl-3,7-diazabicyclo[3.3.1]nonane (183 g, 0.88 mol) was charged to the flask. Data collection was started on the ReactIR instrument, and the solution was cooled to −72 to −75° C. sec-Butyllithium (600 mL, 1.6 M in cyclohexane) was slowly added to the reaction mixture, keeping the reaction temperature below −69° C. The addition was monitored with the ReactIR instrument, and the addition was stopped after the absorbance at 1698 $cm^{-1}$ had disappeared and the absorbance at 1654 $cm^{-1}$ ceased to increase for three consecutive scans (2-minute intervals). The solution was agitated for 3 hours at −75 to −72° C. A 10% mixture of $CO_2$ in nitrogen was carefully sparged into the reaction mixture, keeping the reaction temperature below −70° C. The sparge was stopped after the absorbance for $CO_2$ appeared in the ReactIR spectrum (2350 $cm^{-1}$). The mixture was warmed to 0-5° C., and a solution of 30 wt % $NaHSO_4$ (1.4 L) was added. The mixture was warmed to 22-25° C. and stirred for 30 minutes. The aqueous phase was separated and the organic phase washed with water (700 mL). The aqueous phase was decanted and the organic phase concentrated to provide the title compound.

Method 2

A solution of 3,7-dipropyl-3,7-diazabicyclo[3.3.1]nonane (183 g, 0.87 mol) in MTBE (300 mL) was added to the solution of N-t-butyloxycarbonyl-3-azabicyclo[3.3.0]octane from Example 1, Method 2 in a flask fitted with a mechanical stirrer, an addition funnel, a ReactIR probe, and a thermometer and the mixture was cooled to −75 to 72° C. A solution of sec-butyllithium (510 mL, 1.6 M) was added, keeping the reaction temperature below −70° C., until the absorbance at 1698 $cm^{-1}$ had disappeared and the absorbance at 1654 $cm^{-1}$ ceased to increase. The solution was stirred for 3 hours at −75 to −72° C. The reaction mixture was sparged with 10% $CO_2$ in N2 keeping the reaction temperature below −70° C. The sparge was stopped when the absorbance for $CO_2$ appears in the ReactIR spectrum (2339 $cm^{-1}$). The mixture was warmed to 0-5° C. and a solution of 30 wt % $NaHSO_4$ (1.4 L) was added and the mixture was warmed to 22-25° C. then stirred 30 minutes. The phases were separated and the aqueous phase was checked to make sure the pH was lower than 3. The organic phase was washed with water (700 mL) then concentrated to 300 mL. Ethyl acetate (1.7 L) was added and the mixture concentrated to 300 mL twice to give a solution of the title compound in ethyl acetate.

Example 3

(S)-1,2,3,4-tetrahydronaphthalen-1-aminium (1S,3aR,6aS)-2-(t-butoxycarbonyl)octahydrocyclopenta[c]pyrrole-1-carboxylate (9a)

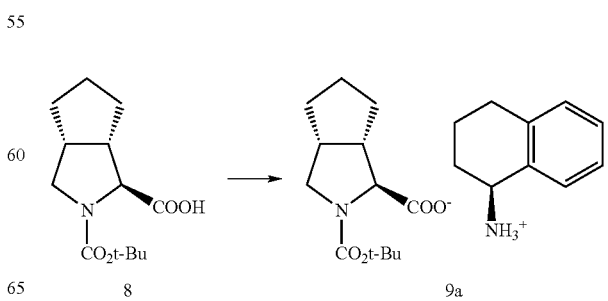

87

Method 1

Ethyl acetate (2.3 L) was added to the residue of Example 2, method 1, and the mixture filtered through a pad of Celite®. (S)-1,2,3,4-tetrahydro-1-naphthylamine (56.7 g, 0.385 mol) was added and the solution was stirred for 3-4 hours at 22-25° C. The mixture was filtered and the solids were rinsed with ethyl acetate (200 mL). The solids were dried at 20-30° C. under vacuum for 4 hours to give the title compound.

To a 3-necked RBF fitted with a temperature controller, a mechanical stirrer, a reflux condenser, and a nitrogen bubbler, was charged the (S)-1,2,3,4-tetrahydro-1-naphthylammonium salt (88.98 g, 0.22 mol), ethyl acetate (712 mL), and 2-propanol (666 mL). The mixture was warmed to 70-75° C. with stirring. The mixture was stirred for 15-30 minutes, then cooled to −5 to −10° C. over 1 hour. The resultant slurry was filtered and the solids were rinsed with cold ethyl acetate (180 mL) to give the title compound as a white solid.

Method 2

The ethyl acetate solution of racemic N-t-butyloxycarbonyl-3-azabicyclo[3.3.0]octane-2-carboxylic acid from Example 2, Method 2, was added to a solution of (S)-1,2,3,4-tetrahydro-1-naphthylamine (56.7 g, 0.385 mol) in ethyl acetate (300 mL). The mixture was stirred for 3-4 hours at 22-25° C., then filtered, and the solids washed with ethyl acetate (200 mL). The product was dried at 20-30° C. under vacuum for 4 hours to give the title compound.

A mixture of the salt as prepared above (89.0 g), ethyl acetate, and 2-propanol was warmed to 70-75° C. until complete dissolution. The mixture was cooled to −5 to −10° C. over two hours and stirred for 3-4 hours. The mixture was filtered and the product dried at 35-40° C. to give the title compound.

Example 4

(R)-1-phenylethanaminium (1S,3aR,6aS)-2-(t-butoxycarbonyl)octahydrocyclopenta[c]pyrrole-1-carboxylate (9b)

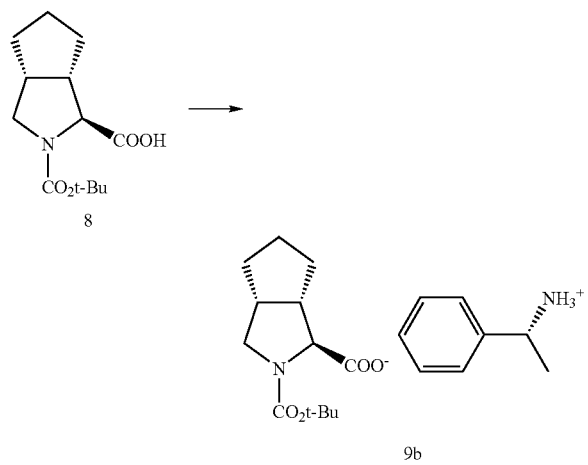

To a solution of racemic N-t-butyloxycarbonyl-3-azabicyclo[3.3.0]octane-2-carboxylic acid (4.66 g) in ethyl acetate (100 mL) was added (R)-α-methylbenzylamine (56.7 g) and the solution was stirred for 16 hr at 22-25° C. The mixture was filtered and the solids were rinsed with ethyl acetate. The solids were dried at 20-30° C. under vacuum for 4 hours to give the title compound.

Example 5

(1S,3aR,6aS)-t-butyl octahydrocyclopenta[c]pyrrole-1-carboxylate, t-butylester, oxalate

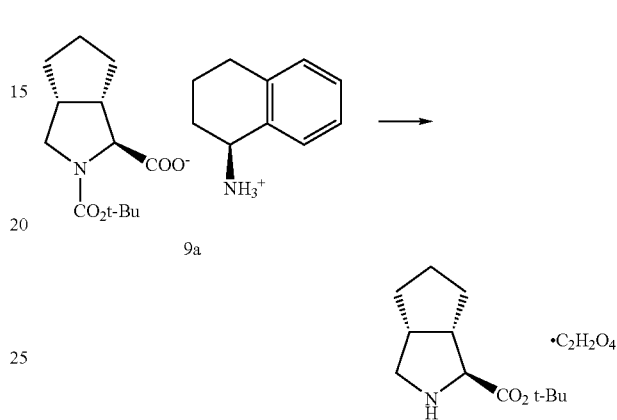

Method 1

A mixture of the (S)-1,2,3,4-tetrahydro-1-naphthylammonium salt prepared as in Example 3, Method 1 (81.7 g, 0.203 mol), t-butyl methyl ether (400 mL) and 5% NaHSO$_4$—H$_2$O (867 mL, 0.304 mol) was stirred for 30 minutes until all solids were dissolved. The organic phase was washed with water (334 mL) then concentrated to 259 mL. t-Butyl methyl ether (334 mL) was added and the solution was concentrated again to 259 mL. The addition-concentration process was repeated twice more. After the final concentration, t-BuOH (158 mL) and dimethylaminopyridine (5.04 g, 41.3 mmol) were added. A solution of Boc$_2$O (67.6 g, 0.31 mol) in t-butylmethyl ether (52.0 mL) was added. After stirring for 5 hours at ambient temperature, t-butyl methyl ether (158 mL) and 5% aqueous NaHSO$_4$—H$_2$O (260 mL) were added and the resultant mixture was stirred. The organic phase was washed with 5% aqueous NaCl (twice, 260 mL each). The organic phase was concentrated to 320 mL, and tetrahydrofuran (320 mL) was added. The organic phase was concentrated again to 320 mL, and tetrahydrofuran (320 mL) was added. After concentrating to 320 mL once more, methane sulfonic acid (80.1 g, 0.62 mol) was added and the solution was stirred at ambient temperature for 4.5 hours. The reaction mixture was added to a 30% aqueous solution of K$_2$CO$_3$ (571 mL) and stirred. The aqueous phase was extracted with isopropyl acetate (320 mL). The combined organic phases were concentrated to 320 mL, and isopropyl acetate (320 mL) was added. The organic solution was concentrated again to 320 mL. The organic phase was washed with water (320 mL). Isopropyl acetate (320 mL) was added to the organic phase and the solution was concentrated to 192 mL. Isopropyl acetate (320 mL) was added a second time, and the organic solution was concentrated to 192 mL. A solution of oxalic acid (24.1 g, 267 mmol) in isopropyl acetate (448 mL) was added to the organic solution over 2 hours. The mixture was stirred for 2-4 hours, and the slurry was filtered. The white solids were rinsed with isopropyl acetate (100 mL) and dried at 35-40° C. under vacuum to yield the title compound.

Method 2

A mixture of (S)-1,2,3,4-tetrahydro-1-naphthylammonium salt as prepared by the method of Example 3, Method 2 (148 g, 0.609 mol), t-butyl methyl ether (726 mL) and 5% NaHSO$_4$—H$_2$O (1.58 L, 0.913 mol) was stirred until all of the solids had dissolved. The phases were separated and the organic phase washed with water (726 mL). The organic phase was concentrated to about 400 mL. t-Butyl methyl ether (726 mL) was added and the mixture concentrated to 590 mL. The addition of t-butyl methyl ether and concentration was repeated to give a final volume of 350 mL. Dimethylaminopyridine (8.42 g, 68.9 mmol) and t-butyl alcohol (260 mL) were added, followed by addition of a solution of Boc$_2$O (112 g, 0.52 mol) in MTBE (88 mL) over 0.5 hour. The mixture was stirred for 5 hours at 22-25° C. A solution of 5% sodium bisulfate in water was added and the mixture stirred for 0.5 hour. The organic phase was washed with 5% sodium chloride (twice, 440 mL each) and concentrated to 270 mL, Tetrahydrofuran (540 mL) was added and the mixture concentrated to 270 mL; this procedure was repeated twice more to give a final volume of 270 mL. Methane sulfonic acid (67 mL) was added over 0.5 hour while maintaining a temperature of lower than 30° C. and the mixture stirred at 22-25° C. for 12 hours. The mixture was added to a 30% aqueous solution of potassium carbonate (478 mL) while maintaining a temperature of 22-25° C. The mixture was filtered, the phases separated and the aqueous phase extracted with isopropyl acetate (twice, 540 mL each). The organic phase was concentrated to 270 mL, then twice evaporated with isopropyl acetate (540 ml) to give a final volume of 540 mL. The organic phase was washed with water (twice, 540 mL), then twice evaporated with isopropyl acetate (320 mL) to give a final volume of 320 mL. Additional isopropyl acetate (429 mL) was added followed by addition of a solution of oxalic acid (40.4 g, 0.448 mol) in t-butylmethyl ether (321 mL) over 2 hours maintaining a temperature of 22-25° C. The mixture was stirred for 3 hours at 22-25° C. then filtered. The filter cake was washed with isopropyl acetate (100 mL) and the product dried at 35-40° C. under vacuum to give the title compound as a white solid.

Example 6

(1S,3aR,6aS)-t-butyl 2-((S)-2-(benzyloxycarbonylamino)-3,3-dimethylbutanoyl)octahydrocyclopenta[c]pyrrole-1-carboxylate (27)

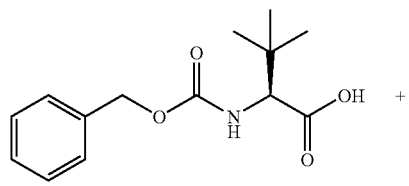

26

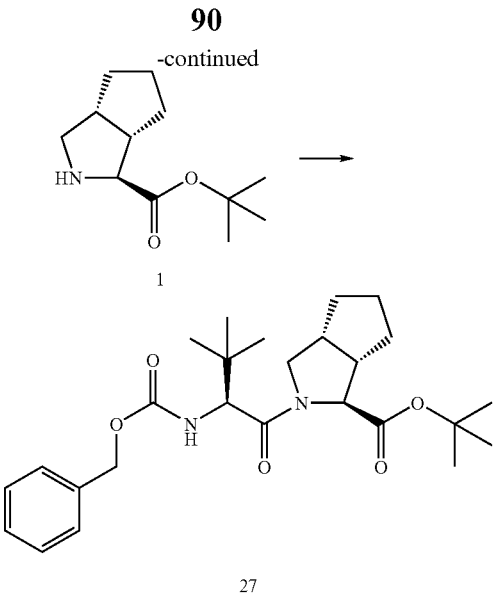

Method 1

A 3-L 3-neck round bottomed flask equipped with an overhead stirrer, condenser, thermocouple, and nitrogen outlet was purged with nitrogen for several minutes. In a separate flask, sulfuric acid (46.2 mL, 0.867 mol) was diluted with 442 mL of water. The solution was allowed to cool slightly. Cbz-L-tert-Leucine dicyclohexylamine salt (330.0 g, 0.739 mol) was charged to the reaction flask. t-Butyl methyl ether (1620 mL) was added to the reactor, and the mixture was stirred to suspend the salt. The acid solution prepared above was added to the reactor over about 10 minutes, keeping the temperature at 20±5° C. The mixture was stirred at room temperature for approximately 1 hour, then diluted slowly with water (455 mL). Agitation was stopped, and the layers were allowed to settle. The lower (aqueous) phase was withdrawn to provide 1100 mL colorless solution of pH 1. To the organic phase remaining in the flask was charged additional water (200 mL). The mixture was stirred at room temperature for approximately 1 hour. Agitation was stopped, and the layers were allowed to settle. The lower (aqueous) phase was withdrawn to provide 500 mL colorless solution of pH 2. The organic phase was heated to about 35° C., diluted with DMF (300 mL), and concentrated under reduced pressure to the point at which distillation slowed significantly, leaving a concentrate of about 500 mL. The concentrate was transferred without rinsing to a 1-L Schott bottle. The concentrate, a clear colorless solution, weighed 511.6 g. Based on solution assay analysis and the solution weight, the solution contained 187.2 g (0.706 mol) Cbz-L-tert-Leucine.

To a 5-L 4-neck round bottomed flask equipped with an overhead stirrer, thermocouple, addition funnel and nitrogen inlet were charged HOBT.H$_2$O (103.73 g, 0.678 mol, 1.20 molar eq.), EDC.HCl (129.48 g, 0.675 mol, 1.20 molar eq.) and DMF (480 mL). The slurry was cooled to 0-5° C. A 36.6 wt % solution of the acid of Cbz-L-tert-Leucine in DMF (491.3 g, 0.745 mol, 1.32 molar eq.) was added over 47 minutes to the reaction mixture while keeping the temperature at 0-5° C. The reaction mixture was stirred for 1 hour and 27 minutes. A solution of 3-azabicyclo(3.3.0)octane-2-carboxylic acid t-butyl ester in isopropyl acetate (28.8 wt %, 414.3 g, 0.564 mol) was added over 53 minutes while keeping the reaction temperature at 0-5.1° C. The reaction mixture was warmed to 20±5° C. over about 1 hour. 4-Methylmorpholine (34.29 g, 0.339 mol, 0.60 molar eq.) was added over 5 minutes. The reaction mixture was agitated for 16 hours then isopropyl acetate (980 mL) was added to the reaction solution. A solution of histamine.2HCl (41.58 g, 0.226 mol, 0.40 molar eq.) in water (53.02 g) was added to the reaction mixture within 4 minutes, followed by 4-methylmorpholine (45.69 g, 0.45 mol, 0.80 molar eq.). The reaction mixture was sampled after 3.5 hours. Water (758 mL) was added, the mixture stirred for about 20 minutes, then allowed to settle for 11 minutes. The phases were separated. The aqueous phase was extracted with isopropyl acetate (716 mL) and the organic phases were combined. 1N aq. HCl was prepared by adding 37 wt % hydrochloric acid (128.3 mL) to water (1435 ml). The organic phase was washed for about 20 minutes with the 1N hydrochloric acid. A 10 wt % aq. $K_2CO_3$ solution was prepared by dissolving $K_2CO_3$ (171 g, 1.23 mol, 2.19 molar eq.) in water (1540 mL). The organic phase was washed with the 10 wt % aq. $K_2CO_3$ solution for about 20 minutes. The final clear, very slightly yellow organic solution, weighing 1862.1 g, was sampled and submitted for solution assay. Based on the solution assay and the weight of the solution, the solution contained 238.3 g (0.520 mol) of product of the title compound.

$^1$H NMR (DMSO-$d_6$, 500 MHz): δ 7.37 ppm (5H, s), 7.25-7.33 ppm (1H, m), 5.03 ppm (2H, s), 4.17 ppm (1H, d), 3.98 ppm (1H, d), 3.67-3.75 ppm (2H, m), 2.62-2.74 ppm (1H, m), 2.48-2.56 ppm (1H, m), 1.72-1.89 ppm (2H, m), 1.60-1.69 ppm (1H, m), 1.45-1.58 ppm (2H, m), 1.38 ppm (9H, s), 1.36-1.42 ppm (1H, m), 0.97 ppm (9H, s).

Method 2

A solution of potassium carbonate (73.3 g) in water (220 mL) was added to a suspension of (1S,2S,5R) 3-azabicyclo [3.3.0]octane-2-carboxylic, t-butylester, oxalate (80.0 g,) in isopropyl acetate (400 mL) while maintaining a temperature of about 20° C. The mixture was stirred for 0.5 hour, the phases separated and the organic phase washed with 25% w/w aqueous potassium carbonate (80 mL) to give a solution of the free base. In a separate flask, aqueous sulfuric acid (400 mL, 0.863 M) was added to a suspension of Cbz-t-leucine dicyclohexylamine salt (118.4 g) in t-butylmethyl ether (640 mL) while maintaining a temperature of about 20° C. The mixture was stirred for 0.5 hour, the phases separated and the organic phase washed with water (200 mL). The phase were separated and N-methylmorpholine (80 mL) was added to the organic phase which was concentrated under reduced pressure at 40° C. to 80 mL to give the free acid as a solution in N-methyl morpholine. This solution was added to a mixture of EDC. HCl (50.8 g) HOBt hydrate (40.6 g) in N-methyl-morpholine (280 mL) at 0-10° C. The mixture was stirred for 1 hour at about 5° C. The solution of 3-azabicyclo[3.3.0] octane-2-carboxylic, t-butylester from above was added at 0-20° C. followed by N-methylmorpholine (32 mL). The mixture was stirred for 6 hour then diluted with isopropyl acetate (600 mL) followed by 1N HCl (400 mL). After stirring 0.5 hour, the phases were separated and the organic phase washed with 25% w/w aqueous potassium carbonate (400 mL) and water (80 mL). The mixture was stirred for about 1 hour and the phases separated to give a solution of the title compound in isopropyl acetate.

Method 3

(1S,2S,5R) 3-azabicyclo[3.3.0]octane-2-carboxylic, t-bu-tylester, oxalate (1.0 eq.) was suspended in isopropyl acetate (6 vol.) and a solution of potassium carbonate (3.0 eq.) in water (3.5 vol.) was added at 20-25° C. The mixture was stirred for 3 hours then the phases separated. The organic phase was washed with water (2 vol.).

Cbz-t-leucine dicyclohexylamine salt (1.05 eq.) was suspended in isopropyl acetate (6 vol.) and sulfuric acid (1.3 eq.) in water (5 vol.) was added at 20-25° C. The mixture was stirred for 30 minutes, the phases separated, and the organic phase washed twice with water (2.5 vol each).

The two solutions from above were combined and then cooled to 0-5° C. HOBt hydrate (1.1 eq.) and EDC (1.1 eq.) were suspended in the mixture and the mixture stirred for 6 hours. The mixture was washed with water (5 vol.) and the resulting organic phase treated with L-lysine (1 eq.) and N-methylmorpholine (NMM) (2 eq.) at 20-25° C. to destroy excess activated ester. The mixture was then washed with 5% potassium carbonate (5 vol.), 1N hydrochloric acid (5 vol.), 5% potassium carbonate (5 vol.) and twice with water (5 vol. each) to give a solution of the title compound in isopropyl acetate.

Example 7

(1S,3aR,6aS)-t-butyl 2-((S)-2-amino-3,3-dimeth-ylbutanoyl)-octahydrocyclopenta[c]pyrrole-1-car-boxylate (28)

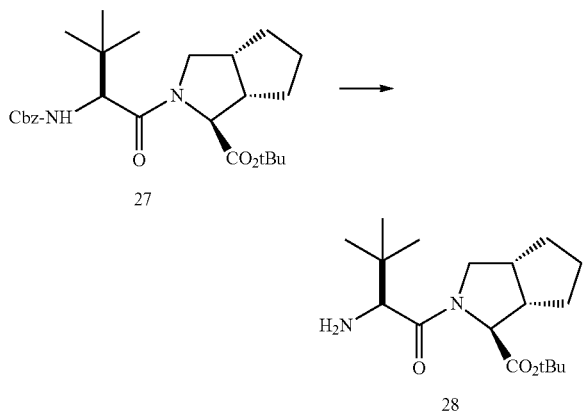

Method 1

A 1 L Buchi hydrogenator was purged with nitrogen three times. A 307.8 g portion of a 12.8 wt % solution of (1S,3aR, 6aS)-t-butyl 2-((S)-2-(benzyloxycarbonylamino)-3,3-dim-ethylbutanoyl)octahydrocyclopenta[c]pyrrole-1-carboxylate (as prepared by the method of Example 6, Method 1) in isopropyl acetate (39.39 g, 0.086 mol) was charged to the reactor. Isopropyl acetate (100 mL) was added to the reactor. A slurry of 50% water and wet 20% Pd(OH)$_2$/carbon (3.97 g) in isopropyl acetate (168 mL) was prepared and charged to the reactor and agitation was started. The reactor was pres-surized to 30 psig with nitrogen gas and vented down to atmospheric pressure. This was repeated twice. The reactor was pressurized to 30 psig with hydrogen and vented down to atmospheric pressure. This was repeated twice. The reactor was pressurized to 30 psig with hydrogen and stirred at ambi-ent temperature for 1 hour. The mixture was filtered using a Buchner funnel with a Whatman #1 filter paper to remove catalyst. The filter cake was washed with isopropyl acetate (80 mL). The procedure was repeated twice more using 617 g and 290.6 g of the 12.8 wt % solution of the starting Cbz compound. The material from the three hydrogenations were combined and distilled under reduced pressure (28" Hg). The resultant solution (468.68 g) was assayed for the title com-pound.

$^1$H NMR (DMSO-$d_6$, 500 MHz): δ 3.96 ppm (1H, d), 3.67 ppm (1H, dd), 3.53 ppm (1H, dd), 3.19 ppm (1H, s), 2.66-2.75 ppm (1H, m), 2.49-2.53 ppm (1H, m), 1.75-1.92 ppm (2H, m), 1.66-1.74 ppm (1H, m), 1.48-1.60 ppm (4H, m), 1.38 ppm (9H, s), 1.36-1.42 ppm (1H, m), 0.91 ppm (9H, s)

Method 2

The solution of the Cbz derivative 27 from Example 6, Method 2, was added to 20% Pd(OH)$_2$/water (50%, 12.2 g) in a hydrogenation apparatus. The apparatus was pressurized to 30 psi with hydrogen then stirred for 2 hr at about 20° C. The mixture was filtered to remove the catalyst, the filter cake washed with isopropyl acetate (160 mL). The combined filtrates were evaporated with about 4 volumes of heptane at 40° C. 2 to 3 times to remove the isopropyl acetate. The resultant slurry was cooled to 0° C., filtered and the product dried under vacuum to give the title compound.

Method 3

A solution of (1S,3aR,6aS)-t-butyl 2*(S)-2-amino-3,3-dimethylbutanoyl)-octahydrocyclopenta[c]pyrrole-1-carboxylate in isopropyl acetate from Example 6, Method 3, was added to 20% Pd(OH)$_2$ (2 wt % loading, 50% wet) and the mixture was hydrogenated at 2 bar and 20-25° C. for 2 hours. The catalyst was removed by filtration and washed with isopropyl acetate (2 vol.). The filtrate was concentrated to 10 vol. under reduced pressure at 40° C. to give a solution of the title compound in isopropyl acetate.

Example 8

(1S,3aR,6aS)-t-butyl 2-((S)-2-((S)-2-(benzyloxycarbonylamino)-2-cyclohexylacetamido)-3,3-dimethylbutanoyl)octahydrocyclopenta[c]pyrrole-1-carboxylate (30)

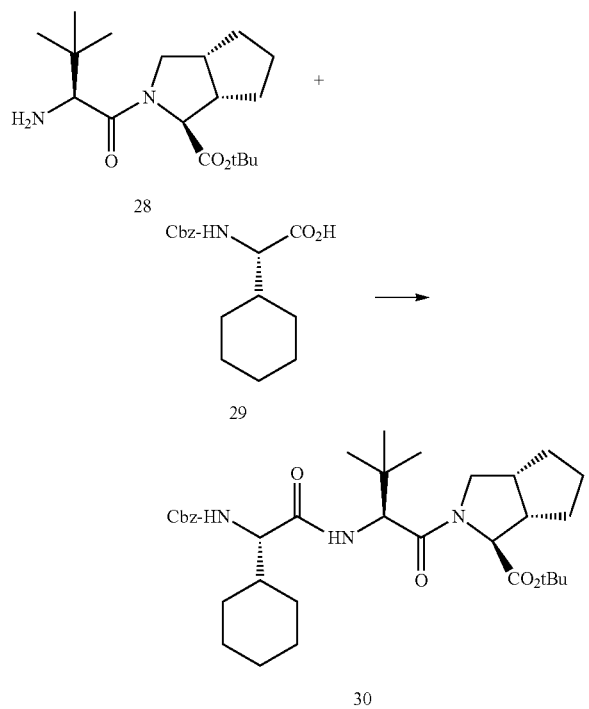

Method 1

To a 3 L 3-neck round bottomed flask equipped with an overhead stirrer, thermocouple, addition funnel, nitrogen outlet and ice/water bath was charged HOBt.H$_2$O (51.74 g; 0.338 mol, 1.05 molar eq.), EDC.HCl (64.8 g; 0.338 mol, 1.05 molar eq.) followed by DMF (197.1 g, 208.8 mL) and agitation was started. The slurry was cooled to 0-5° C., then a solution of the acid 29 (98.45 g; 0.338 mol, 1.05 molar eq.) in DMF (172.4 g; 182.9 mL) was prepared and charged to the addition funnel. This was added over about 30 minutes to the batch, maintaining the temperature at 0-5° C. Once addition was complete the reaction mixture was agitated at 0-5° C. for 2 hours. The solution of the amine 28 in isopropyl acetate (450 g solution; containing 104.4 g of acid 29, 0.322 mol) was charged to an addition funnel and added drop wise over 1 hour maintaining the temperature at 0-5° C. Sample analysis indicated incomplete reaction and additional EDC hydrochloride (3.89 g) was added. After 3 hours, analysis of a sample showed 1.8% amine 28 remained. A slurry of HOBT.H$_2$O (2.59 g; 0.0169 mol), and EDC.HCl (3.24 g; 0.0169 mol) was prepared in DMF (10.44 mL) and cooled to 0-5. A solution of acid 29 (4.92 g; 0.169 mol) in DMF (10.44 mL) was prepared and added to the slurry of EDC.HCl and HOBT in DMF over 30 minutes, maintaining the reaction temperature at 0-5° C. The mixture was stirred for 1 hour at 0-5° C. then added to the original mixture maintaining 0-5° C. The mixture was stirred for 14 hours at about 25° C. A solution of histamine.2HCl (11.84 g; 0.064 mol) in water (8.9 mL) was prepared and added to the reaction mixture over 5-10 minutes. A charge of 4-methylmorpholine (13.01 g; 0.129 mol) was added to the batch over about 10 minutes, maintaining the batch temperature at 20±5° C. The reaction mixture was diluted with isopropyl acetate (443 mL), followed by water (585 mL). A solution of potassium carbonate (57.8 g) in water (585 mL) was added and the mixture was stirred for 0.5 hour. The layers were separated the aqueous layer was extracted twice with isopropyl acetate (twice, 235 mL each). The combined organic phases were washed with 18% aqueous HCl in water (585 mL), then NaHCO$_3$ (43.25 g) in water (585 mL). The layers were separated to give a light yellow solution of product 30 in isopropyl acetate weighing 1159.3 g (1275 mL) containing 16.0 w/w % 30 in isopropyl acetate.

$^1$H NMR (DMSO-d$_6$, 500 MHz): δ 7.74 (1H, d), 7.36 (5H, m), 7.34-7.26 (1H, m), 5.01 (2H, s), 4.51 (1H, d), 4.02 (1H, t), 3.96 (1H, d), 3.73 (1H, m), 3.66 (1H, m), 3.68 (1H, m), 2.53 (1H, m), 1.86-1.76 (2H, m), 1.70-1.30 (10H, m), 1.39 (9H, s), 1.15-0.85 (5H, m), 0.96 (9H, s).

Method 2

A solution of Cbz acid 29 (59.62 g) in N-methylpyrrolidone (126 mL) was added to a suspension of EDC.HCL (39.23 g) HOBt hydrate (31.34 g) in N-methylpyrrolidone (221 mL) while maintaining a temperature of about 0° C. After the addition, the mixture was stirred for 1.5 hours at about 0° C. A solution of the amine 28 (63.24 g, as prepared in Example 7, Method 2) in isopropyl acetate (632 mL) was added to the mixture maintaining a temperature of about 0° C. After the addition the mixture was allowed to warm to room temperature and stirred for 5 hours. A solution of potassium carbonate (20.17 g) in water (316 mL) was added while maintaining a temperature of about 20° C. The mixture was vigorously stirred for 0.5 hour. The phases were separated and the organic phase vigorously stirred with potassium carbonate (105.3 g) in water (316 mL). The organic phase was separated and washed with 1N HCl (316 mL), and then water (158 mL) to give a 12.7% w/w solution of the title compound 30 in isopropyl acetate.

Method 3

To a solution of (1S,3aR,6aS)-t-butyl 2-((S)-2-amino-3,3-dimethylbutanoyl)-octahydrocyclopenta[c]pyrrole-1-carboxylate (1 eq) in isopropyl acetate (10 vol) was added NMP (5 vol) followed by EDC (1.15 eq), HOBT hydrate (1.0 eq) and (S)-2-(benzyloxycarbonylamino)-2-cyclohexylacetic acid (29, 1.05 eq) and the suspension was stirred at 20-25° C. for 4 hr. The mixture was washed with 5% potassium carbonate (5 vol). A mixture of glycine (1 eq), NMM (2 eq) and water (1 vol) was added and the mixture stirred for 4 hr. The mixture was then washed with 5% potassium carbonate (5 vol), 1N hydrochloric acid (5 vol), 5% potassium carbonate (5 vol) and twice with water (5 vol each) to give a solution of the title compound in isopropyl acetate.

Example 9

(1S,3aR,6aS)-tert-butyl 2-((S)-2-((S)-2-amino-2-cyclohexylacetamido)-3,3-dimethylbutanoyl)octahydrocyclopenta[e]pyrrole-1-carboxylate (31)

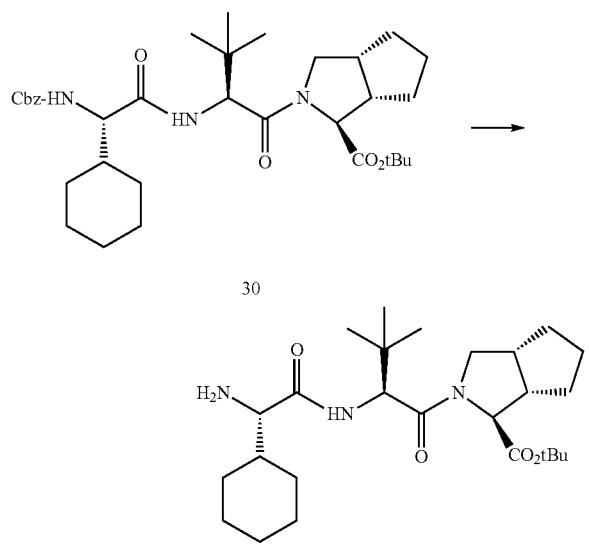

Method 1

A 60-gallon Hastelloy hydrogenating reactor was charged with a solution of the Cbz peptide 30 (15.1 kg) in isopropyl acetate (109 kg). This solution was reduced under vacuum at 50° C. to 68 L. The mixture was then cooled to 25±5° C. and MeOH (15.4 kg) added. This mixture was drained into a container and the reactor was dried. To the dried reactor was charged Pd(OH)$_2$/C (20%, 1.51 kg). The solution containing the Cbz peptide 30 was added to the reactor and blanketed with hydrogen (30 psi). The reaction was stirred at 20±5° C. and at 150-220 rpm for 2 hours. After completion, a slurry of activated carbon (0.97 kg) in isopropyl acetate (6.8 kg) was added batch and the mixture stirred for 15 minutes. The mixture was filtered over Celite® (2.0 kg) via Sparkler filter and through a 0.1-um cartridge filter. The reactor was rinsed with isopropyl acetate (33.0 kg) and the rinse was combined with the reaction mixture. The system was rinsed additionally with a mixture of isopropyl acetate (25.6 kg) and MeOH (5.73 kg). The combined organics were reduced under vacuum at 65° C. to 30 L. The solution was cooled to 20-30° C. and heptane added (30.8 kg). Distillation was instituted again and the mixture reduced to 30 L. This procedure was repeated for a total of 4 heptane additions (as above) and solvent reductions (as above). The mixture was cooled to 0-5° C. and the product filtered and washed with heptane (12.6 kg). The wet solid (14.0 kg) was dried under vacuum at 15-20° C. to constant weight to give the title compound.

$^1$H NMR (DMSO-d$_6$, 500 MHz): δ 7.97 (1H, d), 4.49 (1H, d), 3.96 (1H, d), 3.76 (1H, m), 3.67 (1H, m), 3.05 (1H, d), 2.70 (1H, m), 2.53 (1H, m), 1.87-1.77 (2H, m), 1.7-1.3 (10H, m), 1.39 (9H, s), 1.2-0.85 (5H, m), 0.96 (9H, s).

Method 2

The solution of compound 30 from Example 8, Method 1, was added to 50% wet 20 wt % Pd(OH)$_2$ on carbon (3.16 g) in a pressure reactor. The reactor was pressurized at 30 psi with hydrogen and the mixture stirred for about 1 hour. The catalyst was filtered, the filter washed with isopropyl acetate and the combined organics distilled to about 65 mL. The mixture was evaporated with heptane (316 mL) several times until analysis indicates <0.5% isopropyl acetate. The resultant slurry is diluted to about 320 mL then warmed to reflux. The solution was slowly cooled to about 5° C., the suspension stirred for 1 hour then filtered. The filter cake was washed with about 65 mL of heptane and the product dried under vacuum at 30° C. to give the title compound as a white solid.

Method 3

The solution of (1S,3aR,6aS)-t-butyl 2-((S)-2-((S)-2-(benzyloxycarbonylamino)-2-cyclohexylacetamido)-3,3-dimethylbutanoyl)octahydrocyclopenta[c]pyrrole-1-carboxylate in isopropyl acetate from Example 9, Method 3, was added to 20% Pd(OH)$_2$ (2 wt % loading, 50% wet) and the mixture hydrogenated at 2 bar and 20-25° C. for 2 hour. The catalyst was removed by filtration and washed with isopropyl acetate (1 vol.). The solvent was exchanged by distillation twice with heptane (8.6 vol.) at reflux. The mixture was cooled to 78° C. over 1 hour, then to 22° C. over 2 hours. After 1 hour at 22° C. the suspension was filtered and the cake washed with heptane (3.2 vol.) and the product dried under vacuum at 30° C. with a nitrogen purge to give the title compound.

Example 10

(1S,3aR,6aS)-t-butyl 2-((S)-2-((S)-2-cyclohexyl-2-(pyrazine-2-carboxamido)acetamido)-3,3-dimethylbutanoyl)octahydrocyclopenta[c]pyrrole-1-carboxylate (33)

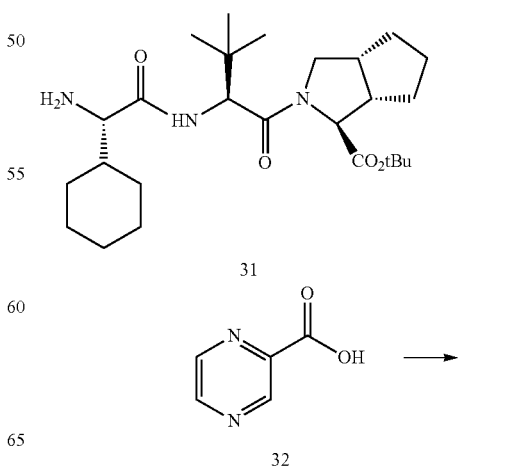

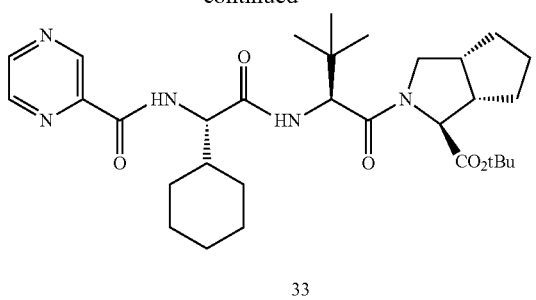

33

Method 1

To a 100 mL round bottomed flask was added pyrazine-2-carboxylic acid 32 (1.6070 g, 12.95 mmol) and DMF (4 mL). The slurry was stirred at 20-25° C. Meanwhile, a solution of CDI was prepared by combining CDI (2.1012 g, 12.96 mmol, 1 molar eq.) and DMF (8.80 g, 9.3 mL) in a 25 mL flask. Mild heating (30° C.) aided in dissolution. The CDI solution was cooled to 20-25° C. and added to the slurry of pyrazine-2-carboxylic acid. Stirring was continued for 1.5 hours to assure complete activation of the acid as carbon dioxide was produced as a byproduct. Meanwhile, the amine 31 (5.0002 g, 10.78 mmol) was dissolved in DMF (14.15 g, 15 mL) with mild warming to 30° C. aided in the dissolution of the material. This solution was cooled to 20-25° C. The activated pyrazine solution was also cooled to about 15° C. The solution of compound 31 was added to the activated pyrazine carboxylic acid while maintaining the temperature at 30° C. for about 1 hour. The solution was allowed to cool to 20-25° C. then added to a solution of potassium carbonate (0.25 g) in water (100 mL) at 0° C. The mixture was filtered and washed with water (four times, 50 mL each). The filter cake was dried under vacuum beginning at 20-25° C. and warmed to 30° C. after 24 hours until the cake was constant weight to give the title compound.

$^1$H NMR (DMSO-$d_6$, 500 MHz): δ 9.19 ppm (1H, d, J=1.3 Hz), 8.90 ppm (1H, d, J=2.5 Hz), 8.76 ppm (1H, dd, J=2.4 Hz, 1.5 Hz), 8.50 ppm (1H, d, J=9.2 Hz), 8.22 ppm (1H, d, J=9.0 Hz), 4.68 ppm (1H, dd, J=9.1 Hz, 6.6 Hz), 4.53 ppm (1H, d, J=9.0 Hz), 3.96 ppm (1H, d, J=4.2 Hz), 3.73 ppm (1H, dd, J=10.5 Hz, 7.5 Hz), 3.68 ppm (1H, dd, J=10.6 ppm, 3.4 ppm), 2.68-2.74 ppm (1H, m), 2.52-2.58 ppm (1H, m), 1.70-1.88 ppm (3H, m), 1.51-1.69 ppm (7H, m), 1.31-1.44 ppm (2H, m), 1.39 ppm (9H, s), 1.00-1.19 ppm (4H, m), 0.97 ppm (9H, s), 0.91-0.97 ppm (1H, m).

Method 2

Oxalyl chloride (11.29 mL) was added to a solution of pyrazine-2-carboxylic acid 32 and N-methylmorpholine (59.28 mL) in methylene chloride (150 mL) at about 30° C. The mixture was stirred for 0.5 hour, then a solution of the amine 31 (50.0 g) in methylene chloride (150 mL) was added at about 30° C. After 0.5 hour, the mixture was washed with water (250 mL). The aqueous phase was extracted with methylene chloride (100 mL) to give a solution of the title compound in methylene chloride which was used directly in the next step (Example 11, Method 2).

Example 11

(1S)-2-((S)-2-((S)-2-cyclohexyl-2-(pyrazine-2-carboxamido)acetamido)-3,3-dimethylbutanoyl)octahydrocyclopenta[c]pyrrole-1-carboxylic acid (34)

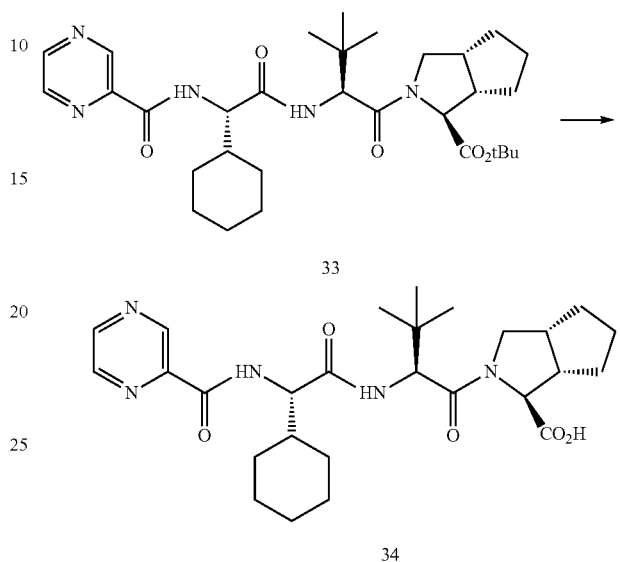

Method 1

Concentrated HCl (150 g, 0.015 mol, 1.2 molar eq.) was slowly added at 0° C. to a stirred solution of the pyrazinyl peptide 33 (50.0 g) in formic acid (100.0 g). After 3.3 hours, the reaction mixture was diluted with 166.5 g of ice water. Methylene chloride (100 mL) was added and the reaction was stirred for 10 minutes to dissolve the product. The phases were separated and the aqueous layer extracted with methylene chloride (100 mL). The combined organic phases were washed with water (75 mL) then concentrated to about ⅓ volume at 50° C., 1 atm. Toluene (100 mL) was added at room temperature and the homogeneous solution was evaporated under vacuum at ≦56° C. to about ⅓ volume. The mixture was cooled to 20-25° C. as a precipitate formed. Heptane (75 mL) was slowly added and the slurry stirred for 10-15 minutes. The slurry was filtered and the filter cake was washed with heptane (50 mL). The solids were dried under vacuum at 20-25° C. to give compound 34. $^1$H NMR (500 MHz, DMSO-$d_6$) 0.88-1.20 (m, 5H), 0.99 (s, 9H), 1.31-1.91 (m, 12H), 2.52 (m, 1H), 2.61 (m, 1H), 3.70 (m, 2H), 4.09 (d, J=4.2 Hz, 1H), 4.57 (d, J=9.0 Hz, 1H), 4.72 (dd, J=9.1, 6.6 Hz, 1H), 8.28 (d, J=9.0 Hz, 1H), 8.52 (d, J=9.2 Hz, 1H), 8.77 (dd, J=2.4, 1.5 Hz, 1H), 8.91 (d, J=2.5 Hz, 1H), 9.22 (d, J=1.3 Hz, 1H), 12.55 (br s, 1H).

Method 2

The methylene chloride solution of the starting compound 33 from Example 10, Method 2, was cooled to 0-5° C. then concentrated HCl (200 mL) was added while maintaining a temperature of <10° C. The mixture was stirred for 3 hours, then diluted with water (200 mL) while maintaining a temperature of <10° C. The phases were separated and the aqueous phase extracted with methylene chloride (100 mL). The combined organic phases were washed with water (100 mL) and the aqueous wash phase extracted with methylene chloride. The combined organic extracts were refluxed under an inverse Dean-Stark trap to azeotrope water. The mixture was concentrated by distillation to a minimum volume then diluted with toluene (500 mL) then concentrated by distillation at atmospheric pressure to 250 mL. The mixture was slowly cooled to 20° C. over about 6 hours. The resultant slurry was filtered, the filter cake washed with toluene (100 mL) then dried at about 45° C. in a vacuum oven to provide the title compound as a pale yellow powder containing about 17% toluene.

Example 12

(1S,3aR,6aS)-2-((S)-2-((S)-2-cyclohexyl-2-(pyrazine-2-carboxamido)acetamido)-3,3-dimethylbutanoyl)-N-((3S)-1-(cyclopropylamino)-2-hydroxy-1-oxohexan-3-yl)octahydrocyclopenta[c]pyrrole-1-carboxamide (35)

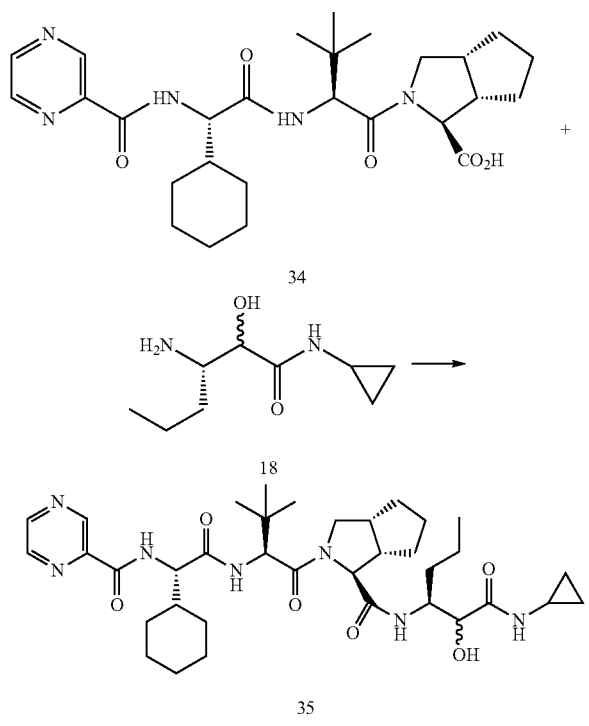

Method 1

A 500 mL 3-neck round bottomed flask equipped with an overhead stirrer, condenser, thermocouple, and nitrogen outlet was purged with nitrogen for several minutes. The peptide-acid 34 (25.0 g, 0.049 mol), EDC-HCl (10.35 g, 0.054 mol, 1.1 molar eq.), and HOBt-H₂O (8.27 g, 0.054 mol, 1.1 molar eq.) were charged to the flask followed by 175 mL of methylene chloride. The mixture was stirred at room temperature for 1 hour then added over 20 minutes to a suspension of hydroxyamide-amine 18 (11.1 g, 0.054 mol, 1.1 molar eq.) in methylene chloride (75 mL) while maintaining a temperature below 10° C. Upon complete addition, N-methylmorpholine (5.94 mL, 0.054 mol, 1.1 molar eq.) was added in 2 portions. The mixture was allowed to warm to room temperature and stirred for 3 hours. The reaction was quenched by the addition of NaHCO₃ (8.0 g) in 200 mL of water. The phases were separated and the organic layer washed with water (175 mL), 0.5 N aq. HCl (200 mL), water (three times, 200 mL each) and saturated NaCl (200 mL) to give a 16% by weight methylene chloride solution of the title compound 35.

Method 2

N-methylmorpholine (38.19 mL, 347.3 mmol) was added to a mixture of the peptide-acid 34 (100.0 g, 89.2 wt %, 173.7 mmol), HOBt hydrate (26.79 g, 87.6 wt %, 173.7 mmol), EDCI (36.62 g, 191.04 mmol), and the hydroxyamide-amine 18 in methylene chloride over 30 minutes while maintaining a temperature of 0-5° C. After the addition, the mixture was warmed to 20° C. and stirred for 5 hours. The mixture was then diluted with water (500 mL) and stirred for about 0.5 hour. The phases were separated and the organic phase washed with 1N HCl (500 mL), 5 wt % aqueous sodium bicarbonate (500 mL) to give a solution of the title compound in methylene chloride, 98.5% AUC purity, 95% solution yield.

Method 3

Peptide acid 34 (1.00 eq.), EDCI (1.10 eq.), HOBt hydrate (1.00 eq.), and hydroxyamine 18.HCl (1.05 eq.) were suspended in CH₂Cl₂ (5 vol.) and the mixture was cooled to 0-5° C. NMM (2.0 eq) was added over 30-60 minutes while maintaining the reaction temperature below 5° C. The reaction mixture was warmed to 20-25° C. over 30 minutes and stirred for additional 5 hours. The reaction was washed with water (5 vol.), 1N HCl (5 vol), and 5 wt % aqueous NaHCO₃ (5 vol.) to provide a solution of the title compound in CH₂Cl₂.

Example 13

(1S,3aR,6aS)-2-((S)-2-((S)-2-cyclohexyl-2-(pyrazine-2-carboxamido)acetamido)-3,3-dimethylbutanoyl)-N—((S)-1-(cyclopropylamino)-1,2-dioxohexan-3-yl)octahydrocyclopenta[e]pyrrole-1-carboxamide (4)

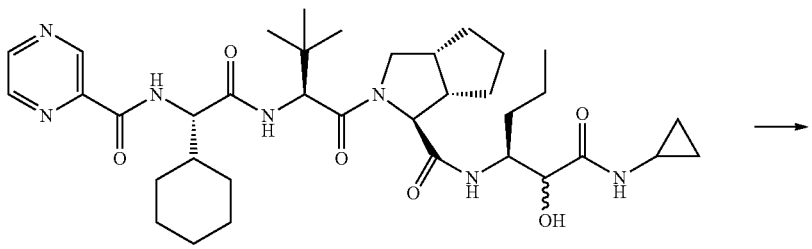

-continued

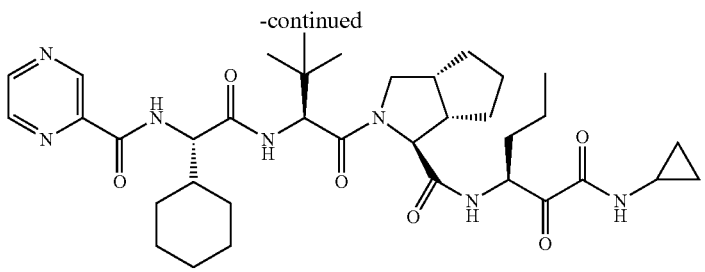

4

Method 1

A 500 mL 3-neck round bottomed flask equipped with an overhead stirrer, condenser, thermocouple, and nitrogen outlet was purged with nitrogen for several minutes. A methylene chloride solution of the hydroxyamide peptide amide 35 (128.64 g, 16-17 wt %, 20.6 g and 30 mmol of 35) in methylene chloride was added to the reaction flask, followed by the addition of 15% w/w aq. NaBr (13 mL) and 7.5% w/w aq. NaHCO$_3$ (52 mL). The solution was cooled to 5±3° C. in an ice bath. TEMPO (0.7 g) dissolved in methylene chloride (3 mL) was added to the reaction mixture. In a separate Erlenmeyer flask, 10-13% NaOCl solution (23.25 mL, titer=108 mg/mL, 2.51 g, 33.7 mmol, 1.12 molar eq.) was diluted with water (70 mL). The NaOCl solution was charged to the reaction mixture via addition funnel at a rate that maintained the temperature below 8° C. The reaction mixture was allowed to stir at 5±3° C. for 1 hour. The layers were separated and the organic layer was quenched with 10% (w/w) aq. Na$_2$SO$_3$ (100 mL) and washed with water (100 mL). The organic phase was reduced to dryness at reduced pressure and the solid triturated with ethyl acetate (100 mL) and filtered on a Buchner funnel to give the title compound.

Method 2

TEMPO (1.09 g, 6.95 mmol) was added to the methylene chloride solution of 35 from Example 12, Method 2, followed by a solution of sodium bicarbonate (21.89 g, 260.5 mmol) in water (400 mL) and the mixture cooled to 0-5° C. A solution of sodium hypochlorite (122.17 g, 11.64 wt %, 191.04 mmol) was added over 2 hours while maintaining a temperature of 0-5° C. The mixture was stirred for 1 hour at 0-5° C., then the phases separated. The organic phase was washed with water (500 mL), 1 wt % aqueous sodium bisulfite (500 mL) and water (500 mL), then polish filtered. The mixture was distilled at 38-42° C., 710 mm Hg, to a volume of about 320 mL. Ethyl acetate (44 mL) was added followed immediately by 1.5 g of seed crystals of 4 and the mixture was stirred for 15 minutes at 38-42° C. Ethyl acetate (800 mL) was added over 3 hours while maintaining a temperature of 38-42° C. The mixture was then distilled at 38-42° C., 200-250 mm Hg, to a volume of about 400 mL. Additional ethyl acetate (200 mL) was added over 0.5 hour. The resultant slurry was cooled over 1 hour to 20-25° C. and stirred an additional hour at the same temperature. The mixture was filtered and the filter cake washed with ethyl acetate (twice, 300 mL each) and dried under vacuum with a nitrogen bleed at 45-55° C. to give the title compound 4 as a white solid.

Method 3

TEMPO (0.06 eq) was added to the CH$_2$Cl$_2$ solution of 35 from Example 12, method 3, and the solution was stirred at 20-25° C. until all TEMPO dissolved. To this solution was added a solution of NaHCO$_3$ (1.5 eq.) in water (4 vol.). The resulting biphasic mixture was cooled to 0-5° C. While maintaining the reaction temperature at 0-5° C., a 10-13 wt % NaOCl solution (1.10 eq.) was added over 2-3 hours and the mixture stirred for additional one hour. The layers were separated and the organic layer was washed at 0-5° C. with H$_2$O (5 vol.), 1 wt % Na$_2$SO$_3$ (5 vol.), and H$_2$O (5 vol.). Glacial acetic acid (0.12 eq.) was added to the solution of compound 4 in CH$_2$Cl$_2$ to stabilize compound 4.

Example 14

Recrystallization of Compound of Formula 4

The solution of Compound 4 from Example 13, Method 3, was filtered through Celite, and the filtrate solution was reduced to 3.1-3.3 volumes by vacuum distillation at lower than 20° C. After distillation, the solution was brought to 38-42° C. before EtOAc (0.80 vol.) was added, followed by the addition of Compound 4 seed (1.5 wt % relative to 34, Example 12). The resulting mixture was stirred for 15 minutes at 38-42° C. EtOAc (8 vol.) was added over 3 hours to this mixture while maintaining a temperature of 38-42° C. The total volume of the slurry was then reduced to 3.9-4.1 volumes by vacuum distillation at 38-42° C. To this mixture was added EtOAc (2 vol.) over 30 minutes while maintaining the batch temperature at 38-42° C. The resulting slurry was then cooled to 20-25° C. over 1 hour and stirred at 20-25° C. for additional 1 hour. The slurry was filtered. The filter cake was washed with EtOAc (twice, 3 vol. each) and dried under vacuum with a nitrogen bleed at 45-55° C. for 6 hours.

To the dried filter cake was added 2.2-2.4 volumes of CH$_2$Cl$_2$ to a total volume of 3.1-3.3 volumes. The mixture was brought to 38-42° C. to give a homogeneous solution. EtOAc (0.80 vol) was added, followed by the addition of Compound 4 seed (1.5 wt % relative to 34, Example 12). The resulting mixture was stirred for 15 minutes at 38-42° C. EtOAc (8 vol.) was added over 3 hours to this mixture while maintaining a temperature of 38-42° C. The total volume of the slurry was then reduced to 3.9-4.1 volumes by vacuum distillation at 38-42° C. EtOAc (2 vol.) was added over 30 minutes to this mixture while maintaining the batch temperature at 38-42° C. The resulting slurry was then cooled to 20-25° C. over 1 hour and stirred at 20-25° C. for additional one hour. The slurry was filtered and the filter cake was washed with EtOAc (twice, 3 vol. each) and dried under vacuum with a nitrogen bleed at 45-55° C. for 12 hour to give purified Compound 4. $^1$H NMR (500 MHz, CDCl$_3$) 0.78 (m, 2H), 0.87 (m, 2H), 0.91 (s, 9H), 0.91 (t [obscured], 3H), 0.98 (m, 4H), 1.08 (m, 1H), 1.20 (m, 4H), 1.29 (m, 1H), 1.40 (m, 1H), 1.42 (m, 2H), 1.46 (m, 1H), 1.48 (m, 1H), 1.60 (m, 1H), 1.70 (m, 1H), 1.79 (m, 1H), 1.83 (m, 2H), 1.88 (m, 1H), 1.94 (m, 1H), 2.67 (m, 1H), 2.89 (bs, 1H), 2.96 (bs, 1H), 3.63 (d, 1H), 3.99 (d, 1H), 4.70 (s, 1H), 4.82 (d, 1H), 4.89 (t, 1H), 5.65

(bs, 1H), 7.74 (bs, 1H), 8.00 (bs, 1H), 8.06 (bs, 1H), 8.29 (bs, 1H), 8.60 (s, 1H), 8.77 (s, 1H), 9.42 (s, 1H).

Example 15

(1S,3aR,6aS)-2-((S)-2-((S)-2-cyclohexyl-2-(pyrazine-2-carboxamido)acetamido)-3,3-dimethylbutanoyl)-N—((S)-1-(cyclopropylamino)-1,2-dioxohexan-3-yl)octahydrocyclopenta[c]pyrrole-1-carboxamide (4)

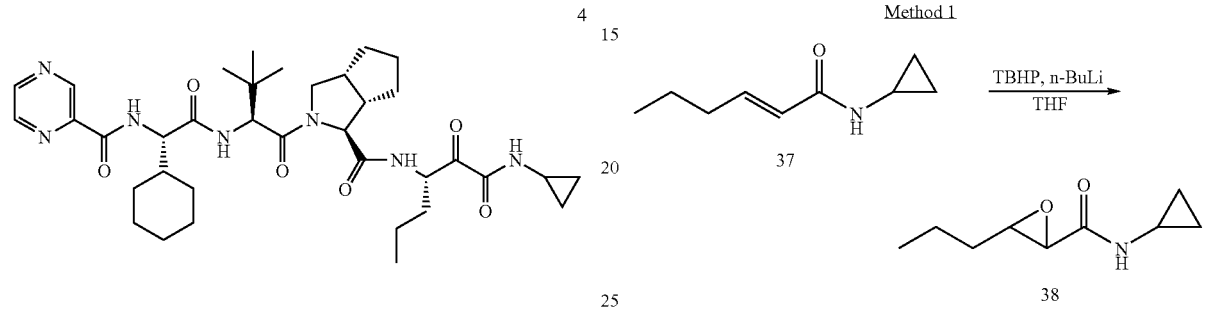

Step a: Trans-N-cyclopropyl-2-hexenamide (37)

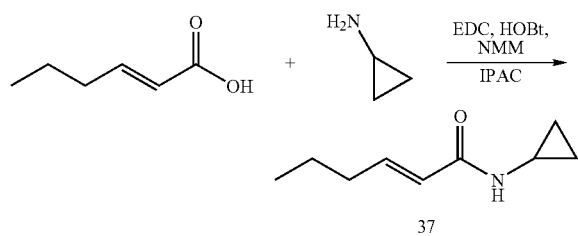

A flask equipped with an overhead stirred, thermometer and addition funnel was placed under a nitrogen atmosphere then charged with (E)-hex-2-enoic acid (89.8 g, 787 mmol), EDCI (158.3 g, 826 mmol), HOBt (112.0 g, 826 mmol) and IPAc (890 mL) then cooled to 0±5° C. The addition funnel was charged with NMM (99.1 mL, 1.6 mol) which was then added to the reaction mixture maintaining the temperature at 0±5° C. The mixture was stirred for 30 minutes then cyclopropylamine (60.0 mL, 866 mmol) was added and the reaction allowed to warm to 25±5° C. over 16 hours. The reaction mixture was washed by adding hydrochloric acid (500 mL, 1.0 N) and the mixture stirred vigorously for 30 minutes then allowed to sit for 30 minutes; the layers were separated and the washing procedure repeated. Sodium hydroxide (500 mL, 1.0 N) was added and then the mixture stirred vigorously for 30 minutes then allowed to sit for 30 minutes; the layers were separated and base wash procedure repeated. Water (500 mL) was added and then the mixture stirred vigorously for 30 minutes then allowed to sit for 30 minutes; the layers were separated and the wash procedure repeated. The combined organic phases were concentrated under reduced pressure to ⅓ original volume then IPAc (600 mL) was added; this was repeated two times when a white precipitate formed. The slurry was then concentrated under atmospheric pressure to ⅔ original volume then cooled to 50±5° C. N-heptane (890 mL) was slowly added while the reaction was cooled to −5±5° C. and held at this temperature for 4 hours. The solid was filtered, washed with cold n-heptane (2×250 mL) and dried to provide compound 37 as a fine white solid. ¹H NMR (500 MHz, d₆-DMSO) 7.89 (s, 1H), 6.58 (dt, J=15.2, 7.0 Hz, 1H), 5.80 (dt, J=15.2, 1.3 Hz, 1H), 2.70-2.65 (m, 1H), 2.12-2.06 (m, 2H), 1.44-1.37 (m, 2H), 0.88 (t, J=7.3 Hz, 3H), 0.64-0.60 (m, 2H), 0.42-0.38 (m, 2H).

Step b: N-cyclopropyl-3-propyloxirane-2-carboxamide (38) or (2S,3R)-N-cyclopropyl-3-propyloxirane-2-carboxamide (39)

Method 1

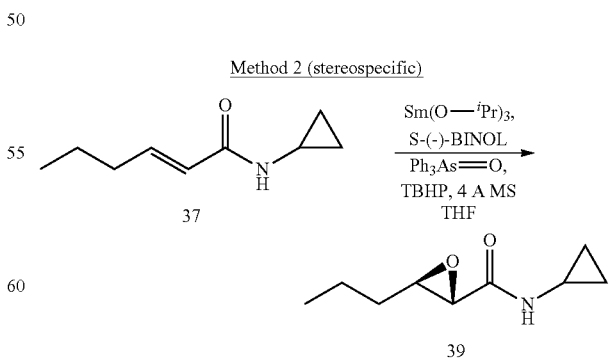

A flask equipped with an overhead stirrer, thermometer and addition funnel was placed under a nitrogen atmosphere then charged with tert-butyl hydrogen peroxide (TBHP; 95 mL, 5.5 M, 522 mmol) and tetrahydrofuran (THF; 200 mL). The reaction was cooled to −20±5° C. and n-butyl lithium (n-BuLi; 235 mL, 2.5 M, 587 mmol) was charged to the addition funnel and slowly added, keeping the reaction temperature below −5±5° C. Upon completion of addition, the reaction was warmed to 0±5° C. and compound 37 (19.80 g, 130 mmol) in THF (20 mL) was added maintaining the temperature at 0±5° C. after which the temperature was increased to 25±5° C. and the reaction stirred for 12 hours. After this time IPAc (200 mL) and saturated aqueous sodium hydrosulfite (200 mL) were added and the reaction stirred for 60 min. The layers were separated and the aqueous layer extracted with IPAc (twice, 75 mL each). The combined organic phases were dried over sodium sulfate (Na₂SO₄), filtered and concentrated under reduced pressure to provide the title compound. ¹H NMR (500 MHz, DMSO-d6): 0.43 (m, 2H), 0.59 (m, 2H), 0.91 (t, J=7 Hz, 3H), 1.32-1.59 (m, 4H), 2.62 (m, 1H), 2.96 (m, 1H), 3.10 (d, J=2 Hz, 1H), 7.99 (br s, 1H).

Method 2 (stereospecific)

A flask equipped with a stir bar, thermometer and addition funnel was placed under a nitrogen atmosphere then charged with samarium (III) isopropoxide (Sm(O-i-Pr)₃, 430 mg, 1.3 mmol), triphenyl arsine oxide (Ph₃As=O; 420 mg, 1.3 mmol), S-(–)1,1'-bi-2-naphthol ((S)-BINOL), 370 mg, 1.3 mmol), 4 Å molecular sieves (13 g) and THF (20 mL) then stirred for 30 min at 25±5° C. Tert-butyl hydroperoxide (2.8 mL, 5.5 M, 16 mmol) was then added. The mixture stirred for 30 minutes at 25±5° C., and compound 37 (2.0 g, 13 mmol) in THF (2.0 mL) was then added. The reaction was stirred for 14 hours after which time the reaction had reached 95% completion as determined by HPLC. The reaction mixture was diluted with ethyl acetate (100 mL) and quenched by addition of 10% citric acid solution (50 mL). The organic phase was separated and filtered through Celite. Distillation of solvent at reduced pressure afforded compound 39 as a pale yellow oil. The ¹H NMR of the product was essentially identical to that of the racemic compound 38.

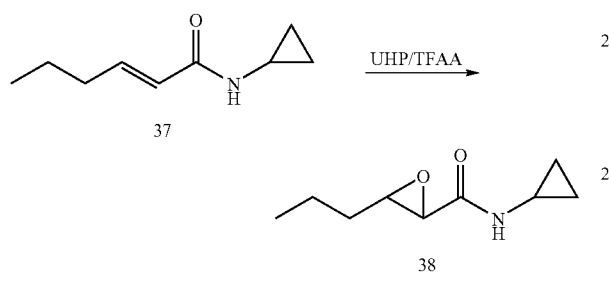

To a three-neck 250 mL round bottom flask equipped with mechanical stirrer and containing compound 37 (10.0 g, 65.3 mmol) and urea hydrogen peroxide (UHP) (25.0 g, 4.0 eq.) in CH₂Cl₂ (100 mL, 10 vol) at 0° C., was added trifluoroacetic anhydride (41.1 g, 27.2 mL, 3.0 eq.). The reaction mixture was heated to 35±5° C. and stirred for 2 hours. After cooling the reaction mixture down to room temperature, another aliquot of trifluoroacetic anhydride (13.7 g, 9.0 mL, 1.0 eq.) was added. The reaction mixture was heated again to 35±5° C. and stirred for another 3 hours. The reaction mixture was then again cooled to 0° C. and quenched by adding saturated NaHCO₃ (5 vol.) slowly and stirring for 30 minutes. The organic layer was separated, and the aqueous layer was extracted with CH₂Cl₂ (50 mL, 5 vol). The combined organic layer was dried and evaporated to afford the crude product, N-cyclopropyl-3-propyloxirane-2-carboxamide (38), as a pale yellow oil. The crude product was used for the next step without further purification.

Step c:
3-Azido-N-cyclopropyl-2-hydroxyhexanamide (40)

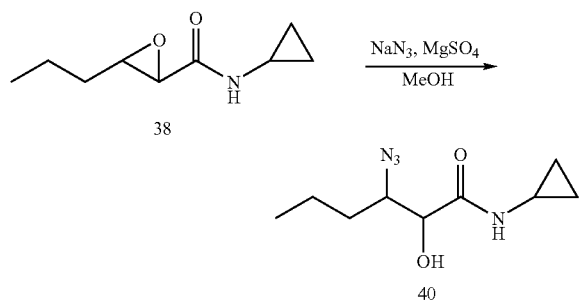

A flask equipped with an overhead stirrer, thermometer and reflux condenser was placed under a nitrogen atmosphere then charged with compound 38 (20.0 g, 118 mmol), sodium azide (NaN₃; 31.0 g, 473 mmol), magnesium sulfate (MgSO₄; 14.0 g, 118 mmol) and methanol (MeOH; 200 mL). The mixture was heated to 65±5° C. for 2 hours then cooled to 25±5 ° C. and filtered through a pad of Celite 545. The solvent was removed under reduced pressure resulting in a thick oil which was taken up in IPAc (250 mL) then washed with water (3×250 mL). The organic phase was dried over sodium sulfate (Na₂SO₄), filtered and concentrated under reduced pressure to provide compound 40 as a white solid. ¹H NMR (500 MHz, d₆-DMSO) 7.87 (s, 1H), 5.97 (d, J=6.0, 1H), 4.02 (dt, J=6.0, 3.8 Hz, 1H), 2.70-2.65 (m, 1H), 1.60-1.20 (m, 4H), 0.88 (t, J=7.0 Hz, 3H), 0.63-0.58 (m, 2H), 0.51-0.46 (m, 2H).

Step d:
3-Amino-N-cyclopropyl-2-hydroxyhexanamide (41)

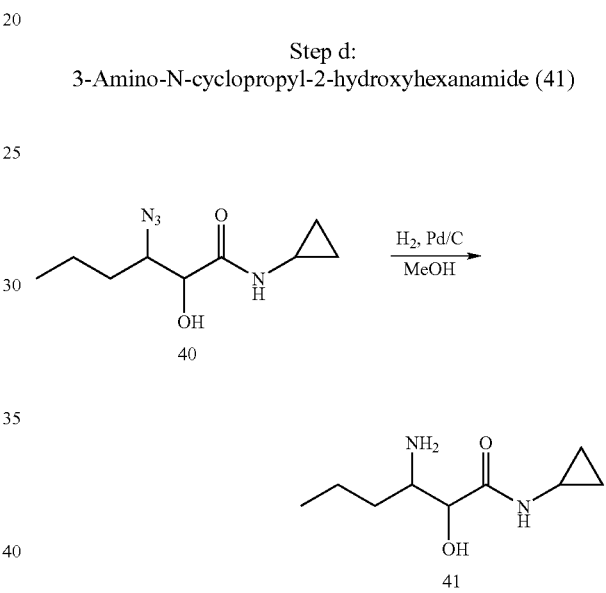

Compound 40 (15.1 g, 71.3 mmol), Pd/C (1.5 g, 5 wt %, 50% wet) and MeOH (150 mL) was charged to a pressure vessel then purged with nitrogen gas for 5 min. The vessel was sealed, pressurized to 1 bar with nitrogen gas then released three times. The same was repeated with hydrogen gas. After the third purge with hydrogen the vessel was charged with 3 hydrogen at a pressure of 3 bars. The reaction was agitated and a temperature of 25±5° C. was maintained for 14 hours after which time the reaction mixture was filtered through a pad of Celite 545 and the solvent removed to provide crude compound 41 (8.48 g) as a yellow solid. To this material was added acetonitrile (ACN; 150 mL) and the reaction heated to reflux at which time all of the solids dissolved. The mixture was then cooled to 25±5° C. and the white needles formed were collected, washed with cold ACN and dried to provide purified compound 41. ¹H NMR (500 MHz, d₆-DMSO): 8.05 (br s, 3H), 4.20 (d, J=3.2, 1H), 3.42-3.34 (m, 1H), 2.71-2.65 (m, 1H), 1.51-1.20 (m, 4H), 1.17 (d, J=6.5 Hz, 1H), 0.83 (t, J=7.6 Hz, 3H), 0.64-0.60 (m, 2H), 0.54-0.49 (m, 2H).

Step e:
3-Amino-N-cyclopropyl-2-hydroxyhexanamide, deoxycholic acid salt (42)

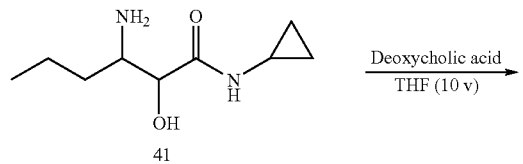

To a three-neck 250 mL round bottom flask equipped with mechanical stirrer and containing the racemic 3-amino-N-cyclopropyl-2-hydroxyhexanamide, 41 (10.0 g, 53.69 mmole), in THF (100 mL) was charged deoxycholic acid (15.8 g, 40.27 mmol, 0.75 eq.). The reaction mixture was stirred at a temperature of 65±5° C. for 2 hours. The resulting homogeneous mixture was allowed to cool to temperatures between 22 and 25° C. over an hour, and was then maintained at this temperature range for an additional 4 hours. The precipitated solids were collected by filtration, washed with THF (10 mL), dried overnight to give 12.2 g of 3-amino-N-cyclopropyl-2-hydroxyhexanamide deoxycholic acid salt, 42, as a white solid.

Step f:
3-Amino-N-cyclopropyl-2-hydroxyhexanamide, hydrochloric acid salt (43)

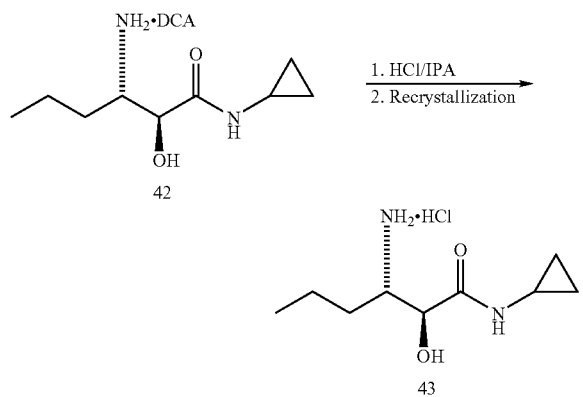

To a three-neck 250 mL round bottom flask equipped with mechanical stirrer and containing the mixture of the deoxycholic salt (42) in 2-propanol (62 mL) was added a 5-6 N HCl solution in isopropyl alcohol (66 mL, 3 eq.) with stirring. The resulting solution was heated at 75±5° C. for an hour and allowed to cool to temperatures between 22 and 25° C. over 1 hour, and was then maintained at this temperature range for an additional 4 hours. The precipitated solids were collected by filtration, washed with 2-propanol (12 mL, 1 vol.), dried overnight to give 7.2 g of the hydrochloric acid salt, 43, as a white solid.

Step g: (1S,3aR,6aS)-2-((S)-2-((S)-2-cyclohexyl-2-(pyrazine-2-carboxamido)acetamido)-3,3-dimethylbutanoyl)-N-((2S,3S)-1-(cyclopropylamino)-2-hydroxy-1-oxohexan-3-yl)octahydrocyclopenta[c]pyrrole-1-carboxamide (36)

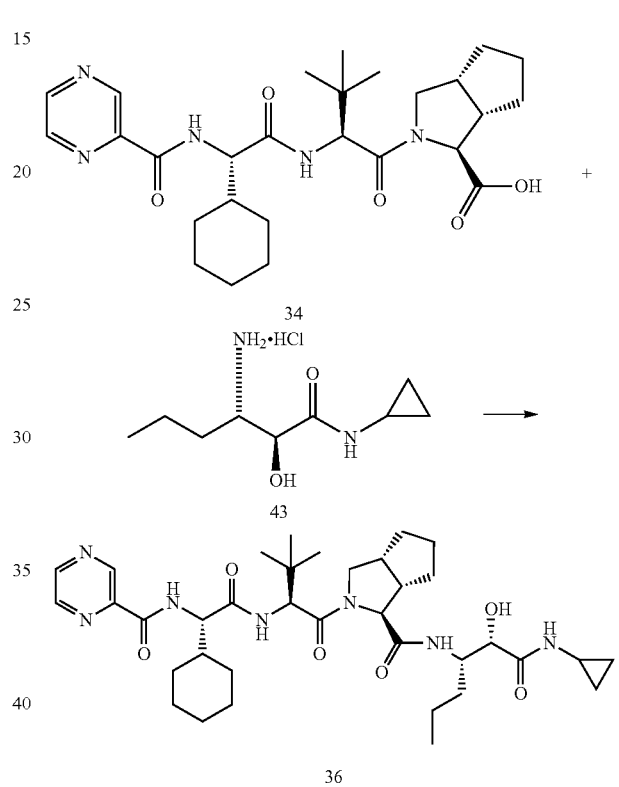

CH$_2$Cl$_2$ (6 vol) is charged into a vessel and cooled to 0-5° C. Carboxylic acid 34 (1.00 eq), HOBt active (1.10 eq), EDCI (1.10 eq), and amine-hydrochloric acid salt 43 (1.10 eq) are charged to the same vessel in this particular order. NMM (2.0 eq) is added over 30-60 minutes while maintaining the reaction temperature below 5° C. The reaction mixture is warmed to 20-25° C. over 30 minutes and stirred for an additional 12 hours. The reaction is washed with water (5 vol), 1N HCl (5 vol), and 5 wt % aqueous NaHCO$_3$ (5 vol) to yield a solution of chiral hydroxy-peptide, 36, in CH$_2$Cl$_2$. $^1$H NMR (500 MHz, DMSO-d6). 0.47 (m, 2H), 0.58 (m, 2H), 0.78 (t, J=7.2 Hz, 3H), 0.80-1.83 (m, 21H), 0.94 (s, 9H), 2.58 (m, 1H), 2.65 (m, 1H), 2.70 (m, 1H), 3.64 (dd, J=3.2, 10.6 Hz, 1H), 3.77 (dd, J=7.8. 10.2 Hz, 1H), 3.80 (dd, J=4.0, 5.8 Hz 1H), 4.04 (m, 1H), 4.26 (d, J=3.0 Hz, 1H), 4.56 (d, J=9.2 Hz, 1H), 4.69 (dd, J=6.4, 9.0 Hz, 1H), 5.56 (d, J=5.8 Hz, 1H), 7.58 (d, J=9.1 Hz, 1H), 7.69 (d, J=4.6 Hz, 1H), 8.23 (d, J=9.2 Hz, 1H), 8.51 (d, J=9.1 Hz, 1H), 8.77 (dd, J=1.5, 2.4 Hz, 1H), 8.91 (d, J=2.5 Hz, 1H), 9.19 (d, J=1.4 Hz, 1H).

Step h: (1S,3aR,6aS)-2-((S)-2-((S)-2-cyclohexyl-2-(pyrazine-2-carboxamido)acetamido)-3,3-dimethylbutanoyl)-N—((S)-1-(cyclopropylamino)-1,2-dioxohexan-3-yl)octahydrocyclopenta[c]pyrrole-1-carboxamide (4)

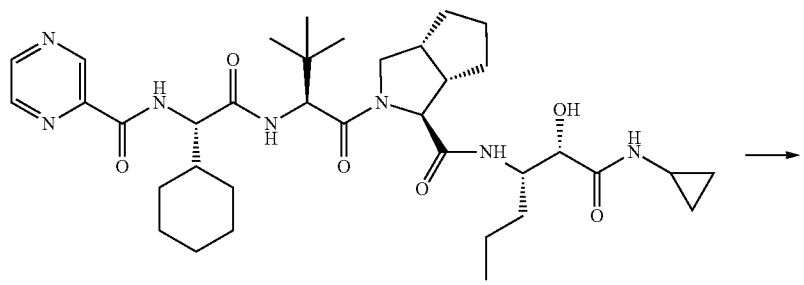

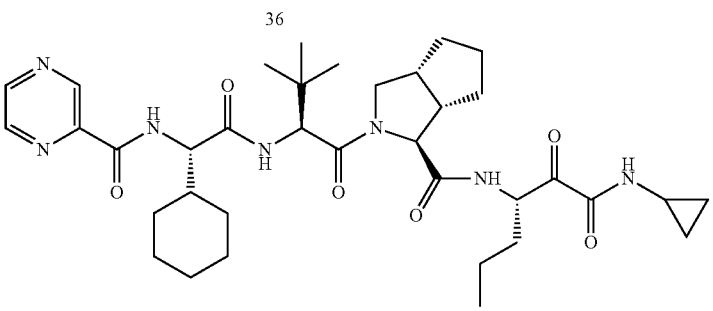

4

The final $CH_2Cl_2$ solution containing chiral hydroxy-peptide 36 from step g of this example is added to a solution of $NaHCO_3$ (1.5 eq) in water (4 vol) at 20-25° C. TEMPO (0.06 eq) is added to the mixture. The resulting biphasic mixture is cooled to 0-5° C. While maintaining the reaction temperature at 0-5° C., a 10-18 wt % NaOCl solution (1.10 eq) is added over 2-3 hours and stirred for an additional 1 hour. The layers are separated and the organic layer is washed at 0-5° C. with an aqueous 5 wt % NaCl solution (5 vol), an aqueous 1 wt % $Na_2SO_3$ and an aqueous 5 wt % NaCl solution (5 vol). Glacial acetic acid (0.12 eq) is added, and the resulting solution of compound 4 in $CH_2Cl_2$ is carried on to the next step.

Step i: Double Recrystallization of (1S,3aR,6aS)-2-((S)-2-((S)-2-cyclohexyl-2-(pyrazine-2-carboxamido)acetamido)-3,3-dimethylbutanoyl)-N—((S)-1-(cyclopropylamino)-1,2-dioxohexan-3-yl)octahydrocyclopenta[c]pyrrole-1-carboxamide (4)

The organic layer from step h of this example is reduced to 3.1-3.3 volumes by vacuum distillation at a temperature less than or equal to 20° C. After distillation, the solution is brought to 38-42° C. EtOAc (0.80 vol) is added followed by the addition of seed crystals of compound 4 (1.5 wt % relative to carboxylic acid 34 charged in step g of this example). The resulting mixture is stirred for 15 minutes at 38-42° C. EtOAc (8 vol) is added over 3 hours to this mixture while maintaining a temperature of 38-42° C. The total volume of the slurry is then reduced to 3.9-4.1 volumes by vacuum distillation at 30-40° C. EtOAc (2 vol) is added over 30 minutes to this mixture while maintaining the batch temperature at 38-42° C. The resulting slurry is then cooled to 20-25° C. over 1 hour and stirred at 20-25° C. for an additional 1 hour. The slurry is filtered. The filter cake is washed with EtOAc (2×3 vol) and dried under vacuum with a nitrogen bleed at 45-55° C. for 5 hours.

The filter cake is cooled to ambient temperature and transferred into a flask where it is dissolved in $CH_2Cl_2$ (3.7 vol). The solution of compound 4 in $CH_2Cl_2$ is filtered and then transferred into the reactor. The flask is washed $CH_2Cl_2$ (1.3 vol), the wash is filtered, and then transferred to the batch. The organic layer is reduced to 3.6-3.8 volumes by vacuum distillation at less than or equal to 20° C. After distillation, the solution is brought to 38-42° C. EtOAc (0.93 vol) is added followed by the addition of seed crystals of compound 4 (1.73 wt % relative to carboxylic acid 34 charged in step g of this example). The resulting mixture is stirred for 15 minutes at 38-42° C. EtOAc (9.4 vol) is added over 3 hours to this mixture while maintaining a temperature of 38-42° C. The total volume of the slurry is then reduced to 4.5-4.7 volumes by vacuum distillation at 30-40° C. EtOAc (2.3 vol) is added over 30 minutes to this mixture while maintaining the batch temperature at 38-42° C. The resulting slurry is then cooled to 20-25° C. over 1 hour and stirred at 20-25° C. for an additional 1 hour. The slurry is filtered. The filter cake is washed with EtOAc (2×3.5 vol) and dried under vacuum with a nitrogen bleed at 45-55° C. for 8 hours. NMR data: see Example 14.

Example 16

(1S,3aR,6aS)-2-((S)-2-((S)-2-cyclohexyl-2-(pyrazine-2-carboxamido)acetamido)-3,3-dimethylbutanoyl)-N—((S)-1-(cyclopropylamino)-1,2-dioxohexan-3-yl)octahydrocyclopenta[c]pyrrole-1-carboxamide (4)

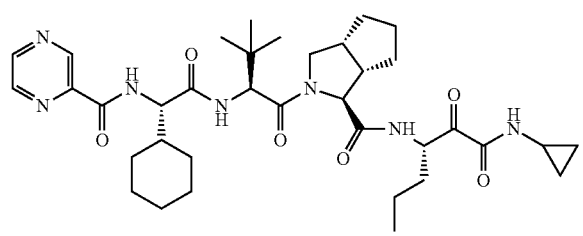

Step a: Preparation of (2R,3S)-3-amino-N-cyclopropyl-2-hydroxyhexanamide (44)

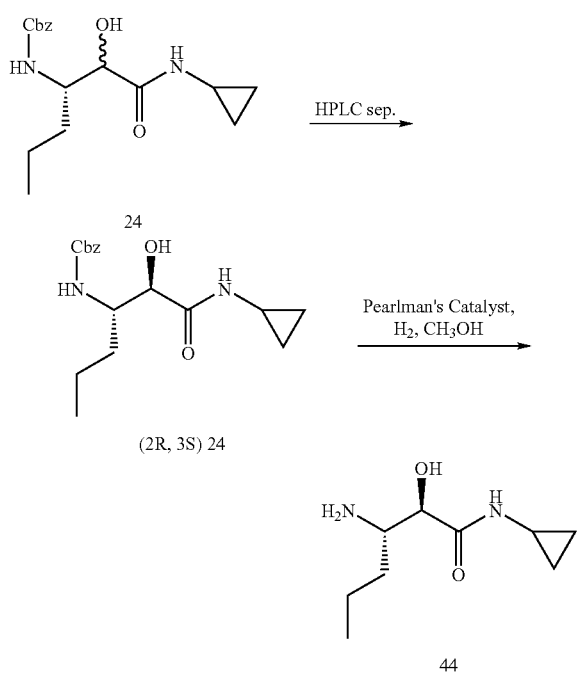

Racemic compound 24, synthesized using the method shown in Scheme IV, was chromatographically separated into its (2S,3S) and (2R,3S) diastereomers via HPLC. The (2R,3S) diastereomer of compound 24 (35.5 g) was dissolved in methanol (355 mL), and palladium hydroxide on carbon ("Pearlman's catalyst, 2.13 g) was added. The system was flushed with nitrogen after which hydrogen was bubbled through for 2 hours. The solution was filtered followed by distillation of solvent. Ethyl acetate (250 mL) was twice added and the mixture again distilled to minimum volume. Ethyl acetate was again added and the solution was concentrated to about 100 mL. Heptane (100 mL) was added and the resulting slurry was stirred at 0° C. for 30 minutes. Compound 44 was collected by filtration, washed with cold heptane, and dried overnight at 40° C. $^1$H NMR [(2R,3S) 24] (500 MHz, DMSO-d6): 0.43 (m, 2H), 0.57 (m, 2H), 0.86 (t, J=7.2 Hz, 3H), 1.12-1.55 (m, 4H), 3.76 (m, 1H), 3.82 (m, 1H), 5.00 (m, 2H), 5.35 (d, J=6.2 Hz, 1H), 6.58 (br d, J=6.2 Hz, 1H), 7.23-7.40 (m, 5H), 7.74 (br d, J=4.8 Hz, 1H). $^1$H NMR [44] (500 MHz, DMSO-d6): 0.47 (m, 2H), 0.59 (m, 2H), 0.86 (t, J=7.1 Hz, 3H), 1.10-1.45 (m, 4H), 2.65 (m, 1H), 2.79 (m, 1H), 3.63 (d, J=3.4 Hz, 1H), 7.72 (br d, J=3.8 Hz, 1H).

Step b: (1S,3aR,6aS)-2-((S)-2-((S)-2-cyclohexyl-2-(pyrazine-2-carboxamido)acetamido)-3,3-dimethylbutanoyl)-N-((2R,3S)-1-(cyclopropylamino)-2-hydroxy-1-oxohexan-3-yl)octahydrocyclopenta[c]pyrrole-1-carboxamide (45)

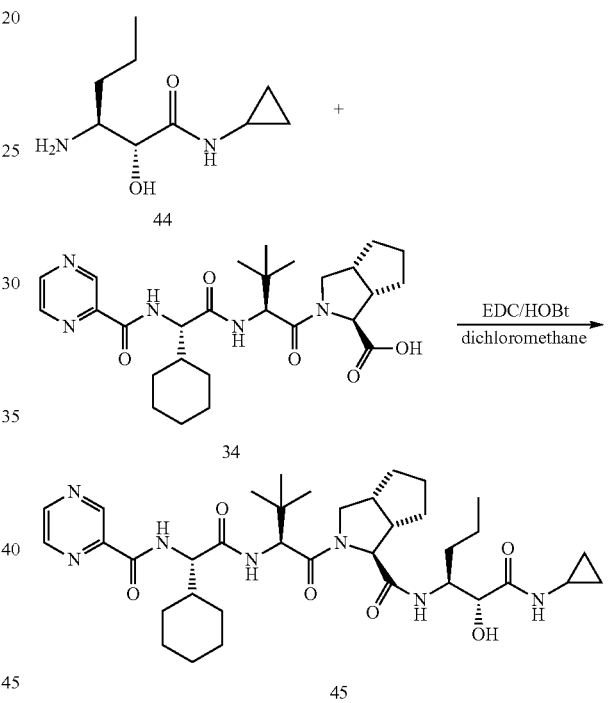

Compound 44 (4.0 g, 7.8 mmol) was dissolved in dichloromethane (35 mL) and the solution was cooled to 10° C. and 1-hydroxybenzotriazole hydrate (1.36 g, 8.9 mmol) was charged. After stirring for 30 minutes, the temperature was further reduced to 0° C. N-(3-dimethylaminopropyl)-N'-ethylcarbodiimide hydrochloride (1.72 g, 9.0 mmol) was added and stirring was continued for 1 hour. Compound 34 (1.77 g, 9.5 mmol) was added and stirring was continued at 0° C. for 30 minutes. The mixture was allowed to warm to room temperature and stirred overnight. The mixture was then sequentially washed with aqueous sodium bicarbonate, dilute hydrochloric acid, and brine. The organic phase was dried over magnesium sulfate, filtered and concentrated. The residue was dissolved in ethyl acetate and re-concentrated 3 times, and then dissolved in ~4 volumes and cooled to 0° C. Heptane was added drop-wise until the solids began to thicken, and then the rate of addition was accelerated until a total of 50 mL of heptane was added. After stirring 30 minutes at 0° C., the product was collected by filtration. After drying at 40° C. overnight, compound 45 was isolated as white solid. $^1$H NMR (500 MHz, DMSO-d6) 0.43 (m, 2H), 0.57 (m, 2H), 0.82 (t, J=7.2 Hz, 3H), 0.8-1.8 (m, 21H), 0.93 (s, 9H), 2.58 (m, 1H), 2.65 (m, 1H), 2.63 (dd, J=3.2 Hz, 10.6, 1H), 3.73 (dd, J=7.7, 10.4 Hz, 1H), 3.81 (dd, J=2.7, 5.9 Hz, 1H), 3.98 (m, 1H), 4.20 (d, J=3.0 Hz, 1H), 4.54 (d, J=9.3 Hz, 1H), 4.68 (dd, J=6.4, 9.1 Hz, 1H), 5.50 (d, J=5.8 Hz, 1H), 7.32 (d, J=9.2 Hz, 1H), 7.59 (d, J=4.3 Hz, 1H), 8.21 (d, J=9.2 Hz, 1H), 8.50 (d, J=9.2 Hz, 1H), 8.76 (dd J=1.6, 2.3 Hz, 1H), 8.90 (d, J=2.4 Hz, 1H), 9.19 (d, J=1.5 Hz, 1H).

Step c: (1S,3aR,6aS)-2-((S)-2-((S)-2-cyclohexyl-2-(pyrazine-2-carboxamido)acetamido)-3,3-dimethylbutanoyl)-N-(S)-1-(cyclopropylamino)-1,2-dioxohexan-3-yl)octahydrocyclopenta[c]pyrrole-1-carboxamide (4)

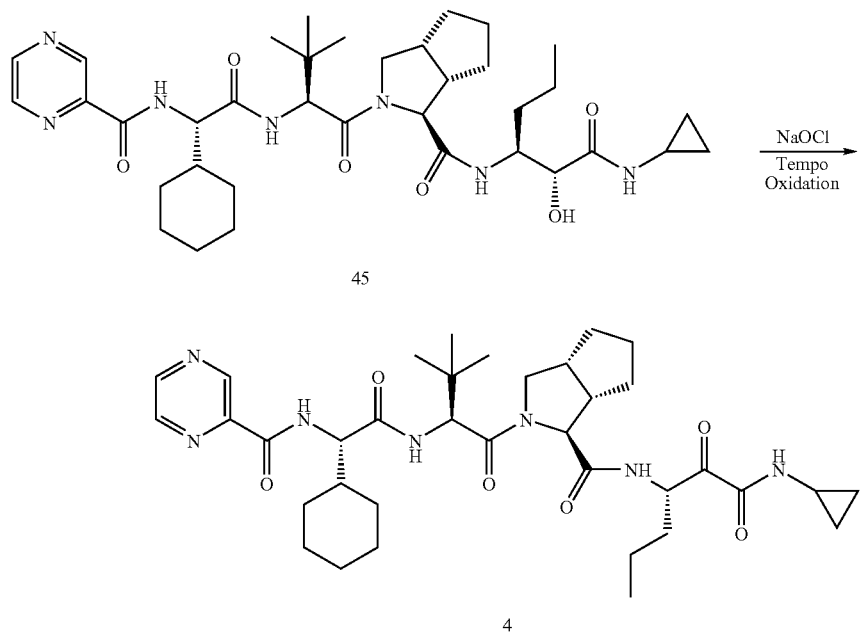

Compound 45 (2.0 g, 2.9 mmol) was dissolved in dichloromethane (14 mL), and to this solution was added a solution of sodium bromide (144 mg) in water (1.0 mL) followed by a solution of sodium bicarbonate (300 mg) in water (4.0 mL). The mixture was cooled to 0° C., whereupon TEMPO (53 mg, 0.34 mmol) was added. Commercial bleach solution containing sodium hypochlorite (3.3 mL) further diluted with water (9.6 mL) was added drop-wise over the course of 10 minutes. The mixture was stirred 1.5 hours at 5° C. after which the organic layer was separated and washed with 10% aqueous sodium sulfite (8 mL) then brine. The resulting solution was dried over magnesium sulfate, filtered, and then concentrated to dryness. After crystallization from dichloromethane/ethyl acetate, compound 4 showed spectroscopic properties identical to those reported in Example 14.

What is claimed is:

1. A process for preparing a racemic mixture of cis- and trans-octahydrocyclopenta[c]pyrrole-1-carboxylic acids of Formula 7

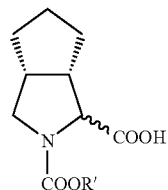

comprising the step of carboxylation of an azabicyclooctane of Formula 6,

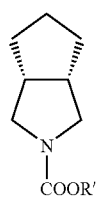

wherein R' is $C_{1-5}$ alkyl.

2. The process of claim 1, wherein the carboxylation step includes forming a 2-anion of the compound of Formula 6

6 in the presence of a complexing agent, and treating the 2-anion with carbon dioxide to produce a racemic mixture of trans-/cis-octahydrocyclopenta[c]pyrrole-1-carboxylic acids of Formula 7

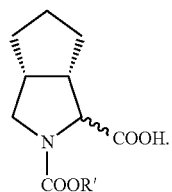

7

3. The process of claim 2, wherein the 2-anion is prepared by treating the compound of Formula 6 with a strong lithium base in the presence of a complexing agent and an aprotic solvent.

4. The process of claim 3, wherein the base is sec-butyl lithium.

5. The process of claim 4, wherein the complexing agent is tetramethylethylenediamine, tetraethylethylenediamine, tetramethyl-1,2-cyclohexyldiamine, sparteine, or 3,7-dipropyl-3,7-diazabicyclo[3.3.1]nonane.

6. The process of claim 2, wherein the complexing agent is tetramethylethylenediamine, tetraethylethylenediamine, tetramethyl-1,2-cyclohexyldiamine, or 3,7-dipropyl-3,7-diazabicyclo[3.3.1]nonane.

7. The process of claim 2, wherein the trans-/cis-ratio is 1 to 1.

8. The process of claim 2, wherein the trans-/cis-ratio is 60 to 40.

9. The process of claim 2, wherein the trans-/cis-ratio is 80 to 20.

10. The process of claim 2, wherein the trans-/cis-ratio is 90 to 10.

11. The process of claim 2, wherein the trans-/cis-ratio is greater than 98 to 2.

12. The process of claim 2, wherein the complexing agent is D-sparteine.

13. The process of claim 3, wherein the lithium base is sec-butyl lithium and the complexing agent is 3,7-dipropyl-3,7-diazabicyclo[3.3.1]nonane to give a mixture of racemic trans-/cis-N-alkoxycarbonyl-octahydrocyclopenta[c]pyrrole-1-carboxylic acids of Formula 7, in which the trans-/cis-ratio is greater than 90 to 10.

14. The process of claim 13, wherein the trans-N-alkoxycarbonyl-octahydrocyclopenta[c]pyrrole-1-carboxylic acid is trans-N-t-butoxycarbonyl-octahydrocyclopenta[c]pyrrole-1-carboxylic acid.

15. A process for preparing a compound of Formula 4

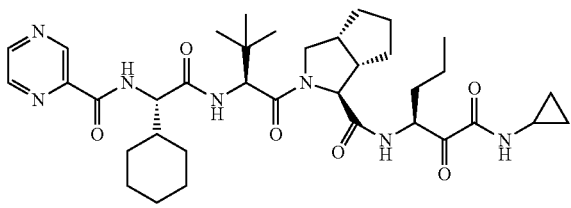

4 comprising the steps of:
i) providing an N-alkoxycarbonyl-3-azabicyclo[3.3.0]octane;
ii) forming a 2-anion of the N-alkoxycarbonyl-3-azabicyclo[3.3.0]octane in the presence of a chelating agent;
iii) treating the anion of step ii) with carbon dioxide to produce a cis-/trans-mixture of N-alkoxycarbonyl-octahydrocyclopenta[c]pyrrole-1-carboxylic acids;
iv) treating the mixture of step iii) with a strong base to produce an essentially pure trans-N-alkoxycarbonyl-octahydrocyclopenta[c]pyrrole-1-carboxylic acid;
v) forming a salt with an optically active amine;
vi) crystallizing the salt;
vii) esterifying the acid provided in step vi);
viii) removing the N-alkoxycarbonyl group to produce (1S, 3aR,6aS)-t-butyl-octahydrocyclopenta[c]pyrrole-1-carboxylate, t-butyl ester;
ix) reacting the bicyclic aminoester of step viii) with a protected amino acid of Formula 26,

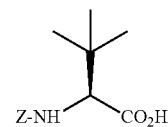

26 wherein Z is an amine protecting group, in the presence of a coupling reagent, to produce an amide-ester of Formula 27;

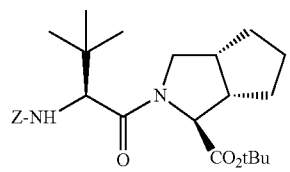

27 x) removing the protecting group Z from the amide-ester of step ix) to produce the amino compound of Formula 28;

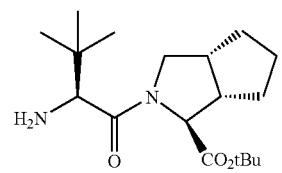

28 xi) reacting the amino compound of Formula 28 with a protected amino acid of Formula 29

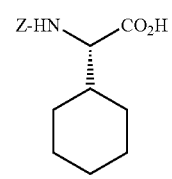

29 in the presence of a coupling reagent to produce a tripeptide of Formula 30;

30

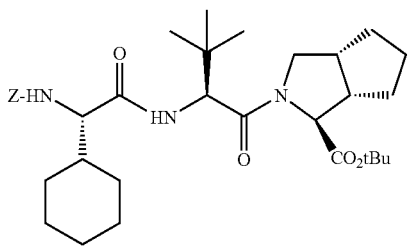

xii) removing the protecting group Z in the tripeptide of Formula 30 to produce a free amino-tripeptide of Formula 31;

31

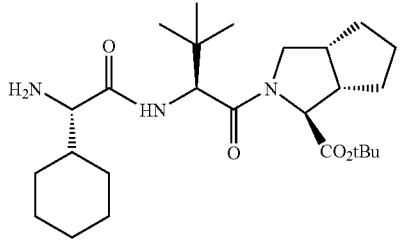

xiii) reacting the amino-tripeptide of Formula 31 with pyrazine-2-carboxylic acid in the presence of a coupling reagent to produce an amide-tripeptide ester of Formula 33;

33

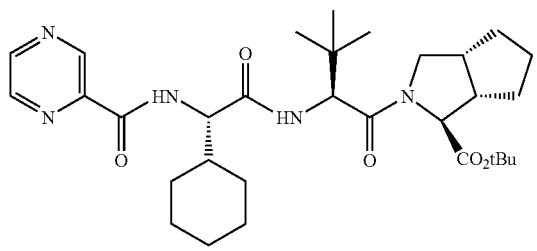

xiv) hydrolyzing the ester of the amide-tripeptide ester of Formula 33 to produce an amide-tripeptide acid of Formula 34;

34

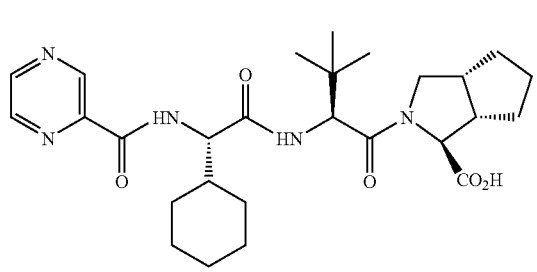

xv) reacting the amide-tripeptide acid of Formula 34 with an aminohydroxy-amide of Formula 18

18

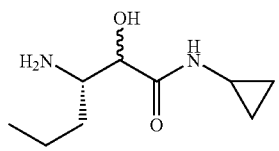

in the presence of a coupling reagent to produce a hydroxy-tetrapeptide of Formula 35; and

35

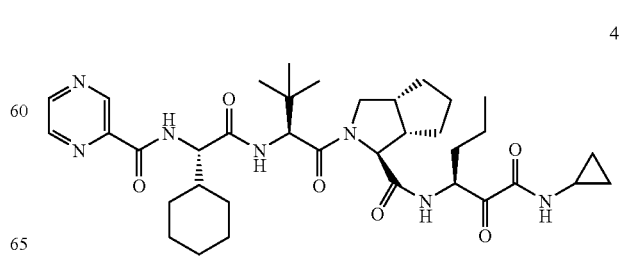

xvi) oxidizing the hydroxy group of Formula 35 to produce the compound of Formula 4

4

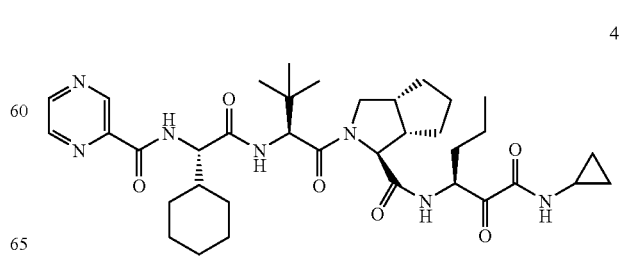

16. The process of claim 15, wherein the oxidizing reagent used in step xvi) is sodium hypochlorite and the oxidation is carried out in the presence of 2,2,6,6-tetramethylpiperidinyloxy free radical (TEMPO).

17. The process of claim 15, wherein the oxidizing reagent used in step xvi) is 1,1-dihydro-1,1,1-triacetoxy-1,2-benzoiodooxol-3(1H)-one.

18. The process of claim 15, further comprising dissolving the compound of Formula 4 in an organic solvent to obtain a solution of the compound of Formula 4, and then adding an acid to the solution.

19. The process of claim 18, wherein the organic solvent is methylene chloride, and the acid is acetic acid.

20. The process of claim 18, further comprising concentrating the solution of the compound of Formula 4 to obtain the compound in a solid form.

21. A process of purifying the compound of Formula 4, comprising:

4

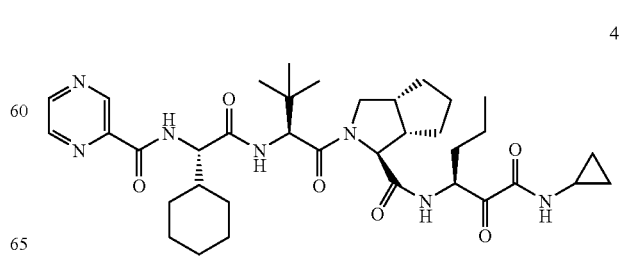

i) dissolving the compound of Formula 4 in an organic solvent to obtain a solution of the compound of Formula 4,
ii) adding an acid to the solution of the compound of Formula 4, and
iii) concentrating the solution of the compound of Formula 4 to obtain the compound in a solid form.

22. The process of claim 21, wherein the organic solvent is methylene chloride, and the acid is acetic acid.

23. A process of preparing a compound of Formula 8

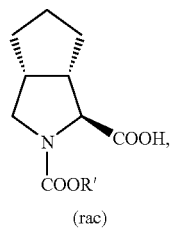

8

(rac)

comprising carboxylating an azabicyclooctane of Formula 6

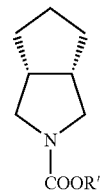

6 to give a racemic mixture of cis and trans octahydrocyclopenta[c]pyrrol-1-carboxylic acids of Formula 7

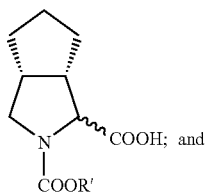

7 equilibrating a trans-/cis-mixture of the compounds of Formula 7 in the presence of a suitable base to produce a predominantly trans-cis racemic acid of Formula 8, wherein the trans-/cis-ratio in the compound of Formula 8 is greater than 80 to 20 and R' is $C_{1-5}$ alkyl.

24. The process of claim 23, further comprising equilibrating trans-/cis-mixture of the compounds of Formula 7 in the presence of a suitable base to produce a predominantly trans-cis racemic acid of Formula 8 wherein the trans-/cis-ratio is greater than 90 to 10.

25. The process of claim 23, further comprising equilibrating trans-/cis-mixture of Formula 7 in the presence of a suitable base to produce a predominantly trans-cis racemic acid of Formula 8 wherein the trans-/cis-ratio is greater than 98 to 2.

26. The process of claim 25, wherein the base is lithium hexamethyldisilazide, lithium di-isopropylamide, or lithium 2,2,6,6-tetramethylpiperidide.

27. The process of claim 26, wherein the base is lithium hexamethyldisilazide.

28. A process of preparing a (1S,2S,3R) trans-N-alkoxycarbonyl-octahydrocyclopenta[c]pyrrole-1-carboxylic acid comprising carboxylating an azabicyclooctane of Formula 6

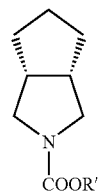

6 to give a racemic mixture of cis and trans octahydrocyclopenta[c]pyrrol-1-carboxylic acids of Formula 7

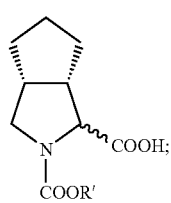

7 equilibrating a trans-/cis-mixture of the compounds of Formula 7 in the presence of a suitable base to produce a predominantly trans-cis racemic acid of Formula 8

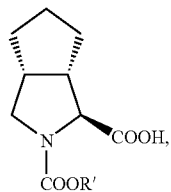

8 wherein the trans-/cis-ratio in the compound of Formula 8 is greater than 80 to 20; and resolving the racemic trans-N-alkoxycarbonyl-octahydrocyclopenta[c]pyrrole-1-carboxylic acid mixture, wherein R' is $C_{1-5}$ alkyl.

29. The process of claim 28, wherein the resolution comprises the steps of:
i) forming a salt with an optically active base; and
ii) crystallizing the salt formed by step i) to provide an optically active salt of Formula 9

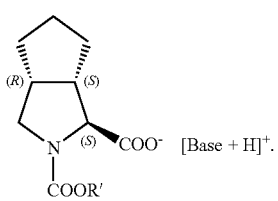

9

30. The process of claim 29, wherein the optically active base is (R) α-aminoethylbenzene.

31. The process of claim 29, wherein the optically active base is (S) 1,2,3,4-tetrahydro-1-naphthylamine.

32. A process preparing a compound of Formula 1 comprising carboxylating an azabicyclooctane of Formula 6

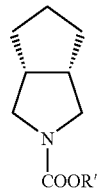

6 to give a racemic mixture of cis and trans octahydrocyclopenta[c]pyrrol-1-carboxylic acids of Formula 7

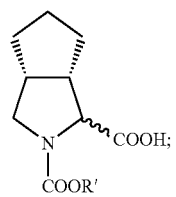

7 equilibrating a trans-/cis-mixture of the compounds of Formula 7 in the presence of a suitable base to produce a predominantly trans-cis racemic acid of Formula 8

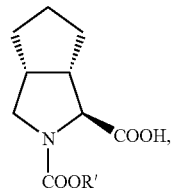

8 wherein the trans-/cis-ratio in the compound of Formula 8 is greater than 80 to 20; forming a salt with an optically active base; crystallizing the salt formed by the previous step to provide an optically active salt of Formula 9

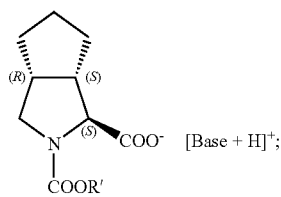

9 esterifying the carboxylic acid of Formula 9 with a compound containing the $R_3$ group; and removing the —COOR' protecting group to produce a compound of Formula 1

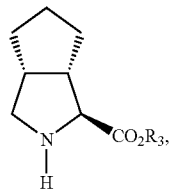

1 wherein R' is $C_{1-5}$ alkyl and $R_3$ is an optionally substituted alkyl or aralkyl.

33. The process of claim 32, wherein $R_3$ is t-butyl.

34. A process for preparing a compound of Formula 4

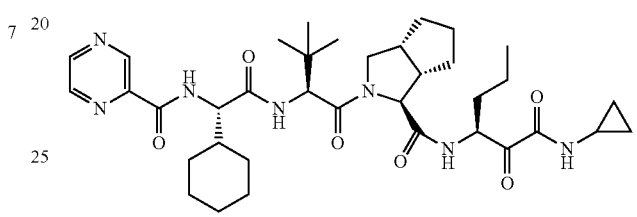

4 comprising the steps of:
i) providing a compound of Formula 7 which was made by the process described in claim 30;
ii) forming a salt with an optically active amine;
iii) crystallizing the salt;
iv) esterifying the acid provided in step iii);
v) removing the N-alkoxycarbonyl group to produce (1S, 3aR,6aS)-t-butyl-octahydrocyclopenta[c]pyrrole-1-carboxylate, t-butyl ester;
vi) reacting the bicyclic aminoester of step v) with a protected amino acid of Formula 26,

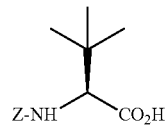

26 wherein Z is an amine protecting group, in the presence of a coupling reagent, to produce an amide-ester of Formula 27;

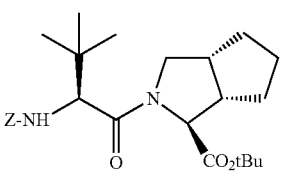

27 vii) removing the protecting group Z from the amide-ester of step vi) to produce the amino compound of Formula 28;

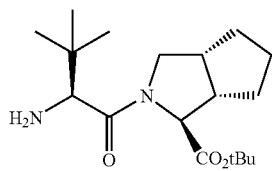
28 viii) reacting the amino compound of Formula 28 with a protected amino acid of Formula 29

29 in the presence of a coupling reagent to produce a tripeptide of Formula 30;

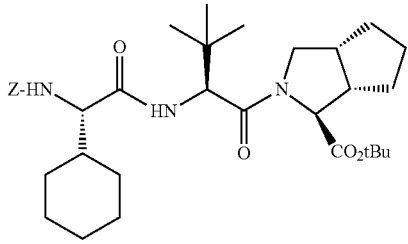
30 ix) removing the protecting group Z in the tripeptide of Formula 30 to produce a free amino-tripeptide of Formula 31;

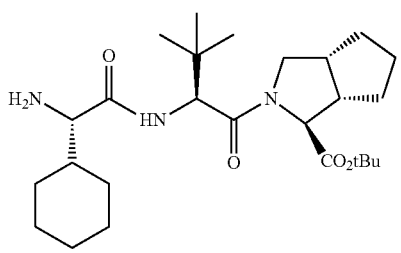
31 x) reacting the amino-tripeptide of Formula 31 with pyrazine-2-carboxylic acid in the presence of a coupling reagent to produce an amide-tripeptide ester of Formula 33;

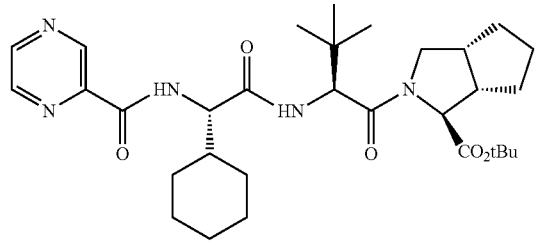
33 xi) hydrolyzing the ester of the amide-tripeptide ester of Formula 33 to produce an amide-tripeptide acid of Formula 34;

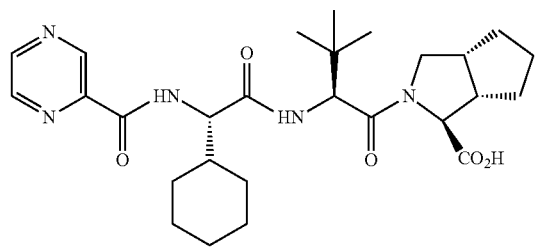
34 xii) reacting the amide-tripeptide acid of Formula 34 with an aminohydroxy-amide of Formula 18

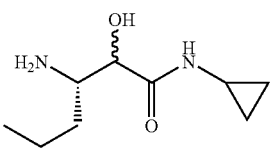
18 in the presence of a coupling reagent to produce a hydroxy-tetrapeptide of Formula 35; and

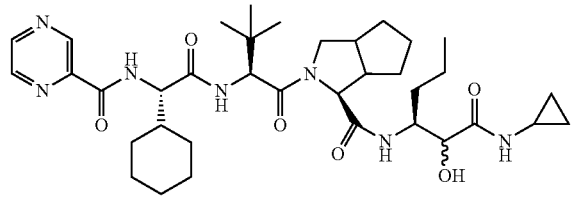
35 xiii) oxidizing the hydroxy group of Formula 35 to produce the compound of Formula 4

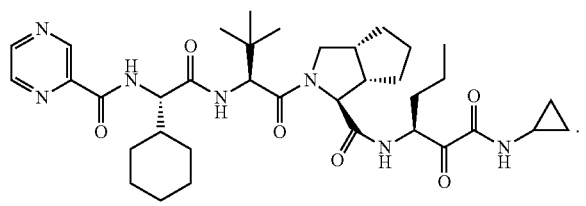

35. A process for preparing a compound of Formula 4

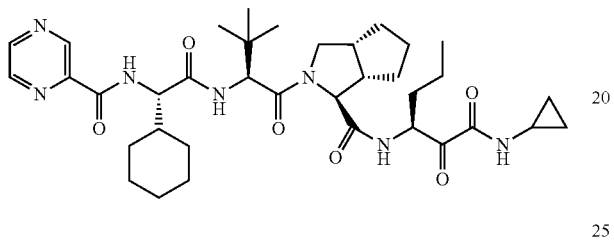

comprising the steps of:
i) providing an N-alkoxycarbonyl-3-azabicyclo[3.3.0]octane;
ii) forming a 2-anion of the N-alkoxycarbonyl-3-azabicyclo[3.3.0]octane in the presence of a chelating agent;
iii) treating the anion of step ii) with carbon dioxide to produce a cis-/trans-mixture of N-alkoxycarbonyl-octahydrocyclopenta[c]pyrrole-1-carboxylic acids;
iv) treating the mixture of step iii) with a strong base to produce an essentially pure trans-N-alkoxycarbonyl-octahydrocyclopenta[c]pyrrole-1-carboxylic acid;
v) forming a salt with an optically active amine;
vi) crystallizing the salt;
vii) esterifying the acid provided in step vi);
viii) removing the N-alkoxycarbonyl group to produce (1S,3aR,6aS)-t-butyl-octahydrocyclopenta[c]pyrrole-1-carboxylate, t-butyl ester;
ix) reacting the bicyclic aminoester of step viii) with a protected amino acid of Formula 26,

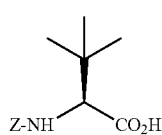

wherein Z is an amine protecting group, in the presence of a coupling reagent, to produce an amide-ester of Formula 27;

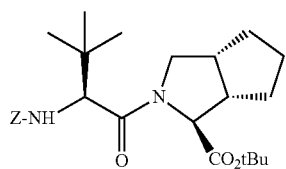

x) removing the protecting group Z from the amide-ester of step ix) to produce the amino compound of Formula 28;

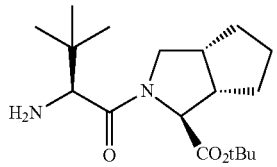

xi) reacting the amino compound of Formula 28 with a protected amino acid of Formula 29

in the presence of a coupling reagent to produce a tripeptide of Formula 30;

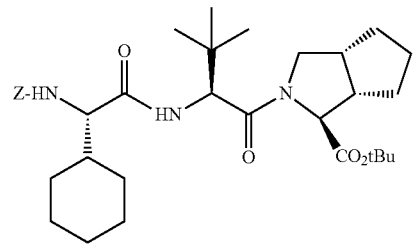

xii) removing the protecting group Z in the tripeptide of Formula 30 to produce a free amino-tripeptide of Formula 31;

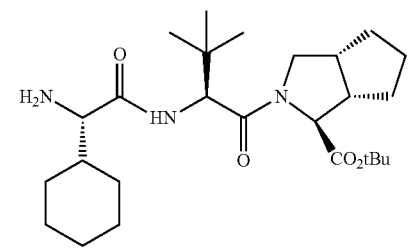

xiii) reacting the amino-tripeptide of Formula 31 with pyrazine-2-carboxylic acid in the presence of a coupling reagent to produce an amide-tripeptide ester of Formula 33;

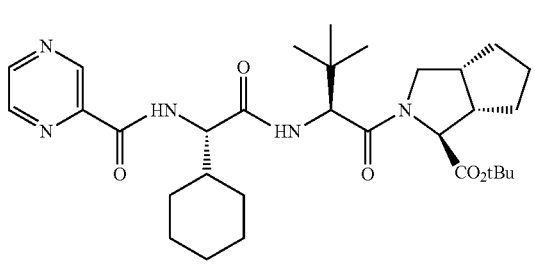

xiv) hydrolyzing the ester of the amide-tripeptide ester of Formula 33 to produce an amide-tripeptide acid of Formula 34;

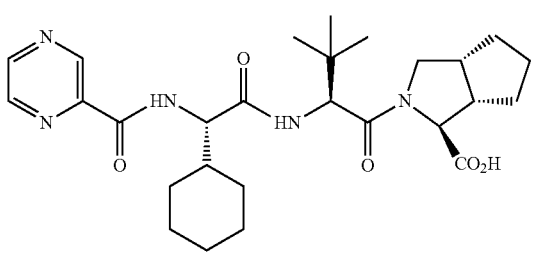

xv) reacting the amide-tripeptide acid of Formula 34 with an aminohydroxy-amide of Formula 44

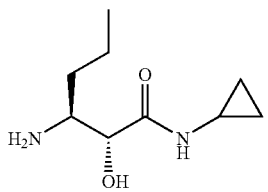

in the presence of a coupling reagent to produce a hydroxy-tetrapeptide of Formula 45; and

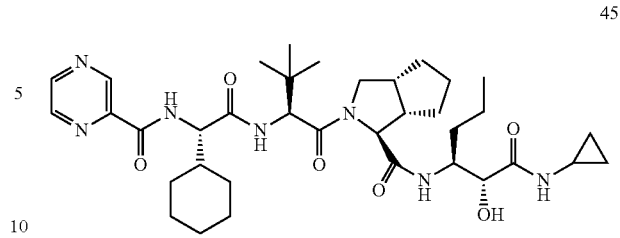

xvi) oxidizing the hydroxy group of Formula 45 to produce the compound of Formula 4

36. The process of claim 34 or 35, wherein the oxidizing reagent used in step xvi) is sodium hypochlorite and the oxidation is carried out in the presence of 2,2,6,6-tetramethylpiperidinyloxy free radical (TEMPO).

37. The process of claim 34 or 35, wherein the oxidizing reagent used in step xvi) is 1,1-dihydro-1,1,1-triacetoxy-1,2-benzoiodooxol-3(1H)-one.

38. The process of claim 34 or 35, further comprising dissolving the compound of Formula 4 in an organic solvent to obtain a solution of the compound of Formula 4, and then adding an acid to the solution.

39. The process of claim 38, wherein the organic solvent is methylene chloride, and the acid is acetic acid.

40. The process of claim 38, further comprising concentrating the solution of the compound of Formula 4 to obtain the compound in a solid form.

* * * * *